US010542961B2

(12) United States Patent
Barsimantov et al.

(10) Patent No.: US 10,542,961 B2
(45) Date of Patent: Jan. 28, 2020

(54) SYSTEM AND METHOD FOR INFRASONIC CARDIAC MONITORING

(71) Applicant: The Research Foundation for The State University of New York, Binghamton, NY (US)

(72) Inventors: Ohad Barsimantov, Staten Island, NY (US); Kenneth McLeod, Vestal, NY (US); J. David Schaffer, Vestal, NY (US)

(73) Assignee: The Research Foundation for the State University of New York, Binghamton, NY (US)

( * ) Notice: Subject to any disclaimer, the term of this patent is extended or adjusted under 35 U.S.C. 154(b) by 279 days.

(21) Appl. No.: 15/182,087

(22) Filed: Jun. 14, 2016

(65) Prior Publication Data

US 2016/0361041 A1    Dec. 15, 2016

Related U.S. Application Data

(60) Provisional application No. 62/175,686, filed on Jun. 15, 2015.

(51) Int. Cl.
*A61B 8/02* (2006.01)
*A61B 8/06* (2006.01)
*A61B 8/08* (2006.01)
*A61B 8/00* (2006.01)

(52) U.S. Cl.
CPC ............ *A61B 8/065* (2013.01); *A61B 8/5223* (2013.01); *A61B 8/02* (2013.01); *A61B 8/565* (2013.01)

(58) Field of Classification Search
CPC .. A61B 8/02; A61B 8/06; A61B 8/065; A61B 5/029; A61B 5/0295
See application file for complete search history.

(56) References Cited

U.S. PATENT DOCUMENTS

| | | |
|---|---|---|
| 4,036,215 A | 7/1977 | Doll |
| 4,195,643 A | 4/1980 | Pratt, Jr. |
| 4,519,395 A | 5/1985 | Hrushesky |
| 4,657,025 A | 4/1987 | Orlando |
| 4,679,569 A | 7/1987 | Lee |
| 4,681,098 A | 7/1987 | Lee |
| 4,738,264 A | 4/1988 | Orlando |
| 4,802,486 A | 2/1989 | Goodman et al. |
| 4,817,610 A | 4/1989 | Lee |

(Continued)

*Primary Examiner* — George R Evanisko
(74) *Attorney, Agent, or Firm* — Tully Rinckey PLLC; Steve M. Hoffberg

(57) ABSTRACT

Cardiac Output (CO) has traditionally been difficult, dangerous, and expensive to obtain. Surrogate measures such as pulse rate and blood pressure have therefore been used to permit an estimate of CO. MEMS technology, evolutionary computation, and time-frequency signal analysis techniques provide a technology to non-invasively estimate CO, based on precordial (chest wall) motions. The technology detects a ventricular contraction time point, and stroke volume, from chest wall motion measurements. As CO is the product of heart rate and stroke volume, these algorithms permit continuous, beat to beat CO assessment. Nontraditional Wavelet analysis can be used to extract features from chest acceleration. A learning tool is preferable to define the packets which best correlate to contraction time and stroke volume.

25 Claims, 11 Drawing Sheets

(56) References Cited

U.S. PATENT DOCUMENTS

| | | |
|---|---|---|
| 4,836,215 A | 6/1989 | Lee |
| 4,838,275 A | 6/1989 | Lee |
| 4,848,350 A | 7/1989 | Lee |
| 4,884,578 A | 12/1989 | Morgenstern |
| 4,889,123 A | 12/1989 | Lee |
| 4,889,130 A | 12/1989 | Lee |
| 4,893,633 A | 1/1990 | Lee |
| 4,895,155 A | 1/1990 | Lee |
| 4,911,167 A | 3/1990 | Corenman et al. |
| 4,926,866 A | 5/1990 | Lee |
| 4,928,692 A | 5/1990 | Goodman et al. |
| 4,934,372 A | 6/1990 | Corenman et al. |
| 5,197,490 A | 3/1993 | Steiner et al. |
| 5,270,529 A | 12/1993 | Shudo |
| 5,333,649 A | 8/1994 | Shimokawa et al. |
| 5,334,444 A | 8/1994 | Bhoori et al. |
| 5,445,162 A | 8/1995 | Ives |
| RE35,122 E | 12/1995 | Corenman et al. |
| 5,507,785 A | 4/1996 | Deno |
| 5,602,964 A | 2/1997 | Barrett |
| 5,649,065 A | 7/1997 | Lo et al. |
| 5,718,720 A | 2/1998 | Prutchi et al. |
| 5,745,382 A | 4/1998 | Vilim et al. |
| 5,782,884 A | 7/1998 | Stotts et al. |
| 5,815,198 A | 9/1998 | Vachtsevanos et al. |
| 5,815,608 A | 9/1998 | Lange et al. |
| 5,845,266 A | 12/1998 | Lupien et al. |
| 5,847,952 A | 12/1998 | Samad |
| 5,940,825 A | 8/1999 | Castelli et al. |
| 5,963,929 A | 10/1999 | Lo |
| 5,964,720 A | 10/1999 | Pelz |
| 5,978,788 A | 11/1999 | Castelli et al. |
| 5,995,868 A | 11/1999 | Dorfmeister et al. |
| 6,012,046 A | 1/2000 | Lupien et al. |
| 6,022,322 A | 2/2000 | Prutchi |
| 6,050,950 A | 4/2000 | Mohler |
| 6,053,872 A | 4/2000 | Mohler |
| 6,091,791 A | 7/2000 | Matsumoto et al. |
| 6,091,841 A | 7/2000 | Rogers et al. |
| 6,098,051 A | 8/2000 | Lupien et al. |
| 6,115,488 A | 9/2000 | Rogers et al. |
| 6,121,969 A | 9/2000 | Jain et al. |
| 6,128,346 A | 10/2000 | Suarez et al. |
| 6,137,898 A | 10/2000 | Broussard et al. |
| 6,152,879 A | 11/2000 | Mohler |
| 6,154,705 A | 11/2000 | McCormack et al. |
| 6,155,976 A | 12/2000 | Sackner et al. |
| 6,167,146 A | 12/2000 | Rogers et al. |
| 6,167,155 A | 12/2000 | Kostrzewski et al. |
| 6,171,263 B1 | 1/2001 | Sullivan |
| 6,179,783 B1 | 1/2001 | Mohler |
| 6,205,236 B1 | 3/2001 | Rogers et al. |
| 6,272,479 B1 | 8/2001 | Farry et al. |
| 6,334,219 B1 | 12/2001 | Hill et al. |
| 6,361,501 B1 * | 3/2002 | Amano .............. A61B 5/02028 600/485 |
| 6,363,350 B1 | 3/2002 | Lafe |
| 6,370,424 B1 | 4/2002 | Prutchi |
| 6,370,481 B1 | 4/2002 | Gamble |
| 6,377,306 B1 | 4/2002 | Johnson et al. |
| 6,389,157 B2 | 5/2002 | Rogers et al. |
| 6,397,136 B1 | 5/2002 | Breed et al. |
| 6,400,996 B1 | 6/2002 | Hoffberg et al. |
| 6,434,583 B1 | 8/2002 | Dapper et al. |
| 6,445,988 B1 | 9/2002 | Breed et al. |
| 6,452,870 B1 | 9/2002 | Breed et al. |
| 6,459,973 B1 | 10/2002 | Breed et al. |
| 6,477,406 B1 | 11/2002 | Turcott |
| 6,478,744 B2 | 11/2002 | Mohler |
| 6,510,406 B1 | 1/2003 | Marchisio |
| 6,529,809 B1 | 3/2003 | Breed et al. |
| 6,535,644 B1 | 3/2003 | Kurapati |
| 6,535,754 B2 | 3/2003 | Fishbein et al. |
| 6,547,743 B2 | 4/2003 | Brydon |
| 6,549,804 B1 | 4/2003 | Osorio et al. |
| 6,551,252 B2 | 4/2003 | Sackner et al. |
| 6,556,699 B2 | 4/2003 | Rogers et al. |
| 6,560,542 B1 | 5/2003 | Mandell et al. |
| 6,601,051 B1 | 7/2003 | Lo et al. |
| 6,640,145 B2 | 10/2003 | Hoffberg et al. |
| 6,647,289 B2 | 11/2003 | Prutchi |
| 6,650,766 B1 | 11/2003 | Rogers et al. |
| 6,650,779 B2 | 11/2003 | Vachtsevanos et al. |
| 6,658,287 B1 | 12/2003 | Litt et al. |
| 6,675,164 B2 | 1/2004 | Kamath et al. |
| 6,678,548 B1 | 1/2004 | Echauz et al. |
| 6,697,661 B2 | 2/2004 | Raghavan et al. |
| 6,708,163 B1 | 3/2004 | Kargupta et al. |
| 6,757,415 B1 | 6/2004 | Rogers et al. |
| 6,757,602 B2 | 6/2004 | Breed et al. |
| 6,763,128 B1 | 7/2004 | Rogers et al. |
| 6,763,322 B2 | 7/2004 | Potyrailo et al. |
| 6,789,054 B1 | 9/2004 | Makhlouf |
| 6,801,645 B1 | 10/2004 | Collins et al. |
| 6,826,300 B2 | 11/2004 | Liu et al. |
| 6,826,428 B1 | 11/2004 | Chen et al. |
| 6,840,907 B1 | 1/2005 | Brydon |
| 6,850,252 B1 | 2/2005 | Hoffberg |
| 6,862,710 B1 | 3/2005 | Marchisio |
| 6,865,492 B2 | 3/2005 | Mandell et al. |
| 6,879,729 B2 | 4/2005 | Kamath et al. |
| 6,882,992 B1 | 4/2005 | Werbos |
| 6,885,975 B2 | 4/2005 | Srinivasan et al. |
| 6,886,008 B2 | 4/2005 | Blayvas et al. |
| 6,970,587 B1 | 11/2005 | Rogers |
| 6,988,093 B2 | 1/2006 | Pic et al. |
| 6,993,378 B2 | 1/2006 | Wiederhold et al. |
| 6,994,675 B2 | 2/2006 | Sharrock |
| 6,996,549 B2 | 2/2006 | Zhang et al. |
| 7,003,403 B1 | 2/2006 | Dougherty et al. |
| 7,006,881 B1 | 2/2006 | Hoffberg et al. |
| 7,007,035 B2 | 2/2006 | Kamath et al. |
| 7,016,885 B1 | 3/2006 | Mikhael et al. |
| 7,019,641 B1 | 3/2006 | Lakshmanan et al. |
| 7,028,015 B2 | 4/2006 | Poluzzi et al. |
| 7,039,462 B2 | 5/2006 | Pastore et al. |
| 7,039,654 B1 | 5/2006 | Eder |
| 7,043,293 B1 | 5/2006 | Baura |
| 7,051,017 B2 | 5/2006 | Marchisio |
| 7,077,810 B2 | 7/2006 | Lange et al. |
| 7,079,896 B1 | 7/2006 | Park et al. |
| 7,082,572 B2 | 7/2006 | Pea et al. |
| 7,085,401 B2 | 8/2006 | Averbuch et al. |
| 7,139,609 B1 | 11/2006 | Min et al. |
| 7,147,246 B2 | 12/2006 | Breed et al. |
| 7,149,320 B2 | 12/2006 | Haykin et al. |
| 7,162,076 B2 | 1/2007 | Liu |
| 7,164,117 B2 | 1/2007 | Breed et al. |
| 7,177,686 B1 | 2/2007 | Turcott |
| 7,180,943 B1 | 2/2007 | Arlid et al. |
| 7,190,149 B2 | 3/2007 | Huff et al. |
| 7,194,143 B2 | 3/2007 | Sowa |
| 7,206,636 B1 | 4/2007 | Turcott |
| 7,209,787 B2 | 4/2007 | DiLorenzo |
| 7,228,238 B2 | 6/2007 | Mandell et al. |
| 7,231,254 B2 | 6/2007 | DiLorenzo |
| 7,233,882 B2 | 6/2007 | Srinivasan et al. |
| 7,242,984 B2 | 7/2007 | DiLorenzo |
| 7,243,945 B2 | 7/2007 | Breed et al. |
| 7,248,923 B2 | 7/2007 | Maile et al. |
| 7,269,537 B1 | 9/2007 | Mattern |
| 7,270,733 B2 | 9/2007 | Wikiel et al. |
| 7,277,758 B2 | 10/2007 | DiLorenzo |
| 7,286,871 B2 | 10/2007 | Cohen |
| 7,286,964 B2 | 10/2007 | Kim |
| 7,293,002 B2 | 11/2007 | Starzyk |
| 7,295,608 B2 | 11/2007 | Reynolds et al. |
| 7,308,126 B2 | 12/2007 | Rogers et al. |
| 7,310,522 B2 | 12/2007 | Geile |
| 7,314,451 B2 | 1/2008 | Halperin et al. |
| 7,324,036 B2 | 1/2008 | Petre et al. |
| 7,324,851 B1 | 1/2008 | DiLorenzo |
| 7,333,851 B2 | 2/2008 | Echauz et al. |
| 7,338,436 B1 | 3/2008 | Snell et al. |

(56) References Cited

U.S. PATENT DOCUMENTS

| | | |
|---|---|---|
| 7,366,719 B2 | 4/2008 | Shaw |
| 7,376,553 B2 | 5/2008 | Quinn |
| 7,379,568 B2 | 5/2008 | Movellan et al. |
| 7,383,237 B2 | 6/2008 | Zhang et al. |
| 7,385,300 B2 | 6/2008 | Huff et al. |
| 7,392,143 B2 | 6/2008 | Jayabalan et al. |
| 7,395,250 B1 | 7/2008 | Aggarwal et al. |
| 7,396,331 B2 | 7/2008 | Mack et al. |
| 7,401,057 B2 | 7/2008 | Eder |
| 7,401,807 B2 | 7/2008 | Breed et al. |
| 7,403,820 B2 | 7/2008 | DiLorenzo |
| 7,407,029 B2 | 8/2008 | Breed et al. |
| 7,408,486 B2 | 8/2008 | Kilbank |
| 7,409,303 B2 | 8/2008 | Yeo et al. |
| 7,415,126 B2 | 8/2008 | Breed et al. |
| 7,417,536 B2 | 8/2008 | Lakshmanan et al. |
| 7,426,499 B2 | 9/2008 | Eder |
| 7,428,323 B2 | 9/2008 | Hillman |
| 7,430,483 B2 | 9/2008 | Wiig |
| 7,451,005 B2 | 11/2008 | Hoffberg et al. |
| 7,454,244 B2 | 11/2008 | Kassab et al. |
| 7,460,903 B2 | 12/2008 | Pineda et al. |
| 7,460,909 B1 | 12/2008 | Koh et al. |
| 7,477,758 B2 | 1/2009 | Piirainen et al. |
| 7,483,868 B2 | 1/2009 | Meng et al. |
| 7,494,459 B2 | 2/2009 | Anstadt et al. |
| 7,502,677 B2 | 3/2009 | Weichenberger et al. |
| 7,511,833 B2 | 3/2009 | Breed |
| 7,519,476 B1 | 4/2009 | Tnacheri et al. |
| 7,526,461 B2 | 4/2009 | Srinivasa et al. |
| 7,533,006 B2 | 5/2009 | Huddleston et al. |
| 7,535,822 B2 | 5/2009 | Geile et al. |
| 7,536,064 B2 | 5/2009 | Venkatesan et al. |
| 7,539,532 B2 | 5/2009 | Tran |
| 7,539,533 B2 | 5/2009 | Tran |
| 7,546,161 B1 | 6/2009 | Bjorling et al. |
| 7,558,622 B2 | 7/2009 | Tran |
| 7,574,255 B1 | 8/2009 | Min |
| 7,575,171 B2 | 8/2009 | Lev |
| 7,577,478 B1 | 8/2009 | Kroll et al. |
| 7,581,434 B1 | 9/2009 | Discenzo et al. |
| 7,584,075 B2 | 9/2009 | Kim |
| 7,587,069 B2 | 9/2009 | Movellan et al. |
| 7,590,510 B2 | 9/2009 | Kim |
| 7,590,589 B2 | 9/2009 | Hoffberg |
| 7,596,242 B2 | 9/2009 | Breed et al. |
| 7,596,470 B2 | 9/2009 | Kim |
| 7,599,759 B2 | 10/2009 | Zugibe et al. |
| 7,604,956 B2 | 10/2009 | Drukier |
| 7,606,790 B2 | 10/2009 | Levy |
| 7,620,527 B1 | 11/2009 | Gielis |
| 7,624,076 B2 | 11/2009 | Movellan et al. |
| 7,630,757 B2 | 12/2009 | Dorfmeister et al. |
| 7,636,600 B1 | 12/2009 | Koh |
| 7,636,700 B2 | 12/2009 | Owechko et al. |
| 7,649,160 B2 | 1/2010 | Colomb et al. |
| 7,650,189 B1 | 1/2010 | Park et al. |
| 7,655,895 B2 | 2/2010 | Breed |
| 7,657,299 B2 | 2/2010 | Huizenga et al. |
| 7,660,437 B2 | 2/2010 | Breed |
| 7,660,632 B2 | 2/2010 | Kirby et al. |
| 7,662,785 B2 | 2/2010 | DeNardo et al. |
| 7,663,502 B2 | 2/2010 | Breed |
| 7,668,697 B2 | 2/2010 | Volkov et al. |
| 7,670,295 B2 | 3/2010 | Sackner et al. |
| 7,672,219 B2 | 3/2010 | Geile |
| 7,672,728 B2 | 3/2010 | Libbus |
| 7,675,843 B2 | 3/2010 | Geile |
| 7,676,062 B2 | 3/2010 | Breed et al. |
| 7,676,263 B2 | 3/2010 | Harris et al. |
| 7,676,266 B1 | 3/2010 | Kroll |
| 7,689,283 B1 | 3/2010 | Schecter |
| 7,693,683 B2 | 4/2010 | Ihara |
| 7,697,453 B2 | 4/2010 | Geile et al. |
| 7,697,792 B2 | 4/2010 | Keating et al. |
| 7,702,185 B2 | 4/2010 | Keating et al. |
| 7,702,555 B1 | 4/2010 | Breeden et al. |
| 7,706,349 B2 | 4/2010 | Geile et al. |
| 7,710,828 B2 | 5/2010 | Barger et al. |
| 7,712,898 B2 | 5/2010 | Abramoff et al. |
| 7,715,894 B2 | 5/2010 | Dunseath et al. |
| 7,716,148 B2 | 5/2010 | Meng et al. |
| 7,727,157 B2 | 6/2010 | Sharrock |
| 7,730,063 B2 | 6/2010 | Eder |
| 7,733,224 B2 | 6/2010 | Tran |
| 7,742,806 B2 | 6/2010 | Sternickel et al. |
| 7,747,325 B2 | 6/2010 | Dilorenzo |
| 7,747,390 B2 | 6/2010 | Miyake et al. |
| 7,756,060 B2 | 7/2010 | Geile et al. |
| 7,768,380 B2 | 8/2010 | Breed et al. |
| 7,769,446 B2 | 8/2010 | Moffitt et al. |
| 7,769,513 B2 | 8/2010 | Breed et al. |
| 7,773,537 B2 | 8/2010 | Geile et al. |
| 7,774,055 B1 | 8/2010 | Min |
| 7,777,743 B2 | 8/2010 | Pao et al. |
| 7,785,257 B2 | 8/2010 | Mack et al. |
| 7,787,946 B2 | 8/2010 | Stahmann et al. |
| 7,788,212 B2 | 8/2010 | Beckmann et al. |
| RE41,771 E | 9/2010 | Geile et al. |
| 7,797,050 B2 | 9/2010 | Libbus et al. |
| 7,805,386 B2 | 9/2010 | Greer |
| 7,813,805 B1 | 10/2010 | Farazi |
| 7,813,822 B1 | 10/2010 | Hoffberg |
| 7,818,053 B2 | 10/2010 | Kassab |
| 7,819,003 B2 | 10/2010 | Breed et al. |
| 7,823,058 B2 | 10/2010 | Pea et al. |
| 7,831,358 B2 | 11/2010 | Breed et al. |
| 7,846,104 B2 | 12/2010 | MacQuarrie et al. |
| 7,848,816 B1 | 12/2010 | Wenzel et al. |
| 7,850,616 B1 | 12/2010 | Gill et al. |
| 7,855,977 B2 | 12/2010 | Morrison et al. |
| 7,856,268 B2 | 12/2010 | Kroll et al. |
| 7,869,869 B1 | 1/2011 | Farazi |
| 7,869,876 B2 | 1/2011 | Prakash et al. |
| 7,872,985 B2 | 1/2011 | Geile et al. |
| 7,877,146 B2 | 1/2011 | Rezai et al. |
| 7,881,180 B2 | 2/2011 | Geile et al. |
| 7,881,181 B2 | 2/2011 | Dapper et al. |
| 7,887,089 B2 | 2/2011 | Breed et al. |
| RE42,236 E | 3/2011 | Geile et al. |
| 7,903,617 B2 | 3/2011 | Liu et al. |
| 7,904,187 B2 | 3/2011 | Hoffberg et al. |
| 7,908,004 B1 | 3/2011 | Gill et al. |
| 7,912,138 B2 | 3/2011 | Geile et al. |
| 7,912,734 B2 | 3/2011 | Kil |
| 7,936,662 B2 | 5/2011 | Geile et al. |
| 7,949,398 B1 | 5/2011 | Wenzel et al. |
| 7,949,399 B2 | 5/2011 | Wenzel et al. |
| 7,953,479 B2 | 5/2011 | Wenzel et al. |
| 7,957,265 B2 | 6/2011 | Geile et al. |
| 7,963,925 B1 | 6/2011 | Schecter |
| 7,966,078 B2 | 6/2011 | Hoffberg et al. |
| 7,974,714 B2 | 7/2011 | Hoffberg |
| 7,981,399 B2 | 7/2011 | Burns |
| 7,983,141 B2 | 7/2011 | Geile |
| 7,983,817 B2 | 7/2011 | Breed |
| 7,987,003 B2 | 7/2011 | Hoffberg et al. |
| 7,995,454 B2 | 8/2011 | Geile et al. |
| 7,996,762 B2 | 8/2011 | Qi et al. |
| 8,000,773 B2 | 8/2011 | Rousso et al. |
| 8,005,524 B2 | 8/2011 | Brauker et al. |
| 8,005,543 B2 | 8/2011 | Libbus et al. |
| 8,005,631 B2 | 8/2011 | Barger et al. |
| 8,010,194 B2 | 8/2011 | Muller |
| 8,015,128 B2 | 9/2011 | Baughman |
| 8,023,710 B2 | 9/2011 | Summers et al. |
| 8,024,044 B2 | 9/2011 | Kirby et al. |
| 8,025,624 B2 | 9/2011 | Wariar et al. |
| 8,027,724 B2 | 9/2011 | Wei et al. |
| 8,031,060 B2 | 10/2011 | Hoffberg et al. |
| 8,032,477 B1 | 10/2011 | Hoffberg et al. |
| 8,036,265 B1 | 10/2011 | Reynolds et al. |
| 8,036,442 B2 | 10/2011 | Bernard et al. |
| 8,036,736 B2 | 10/2011 | Snyder et al. |

(56) References Cited

U.S. PATENT DOCUMENTS

| | | |
|---|---|---|
| 8,041,124 B2 | 10/2011 | Shi et al. |
| 8,041,651 B2 | 10/2011 | Greer |
| 8,046,107 B2 | 10/2011 | Zugibe et al. |
| 8,055,667 B2 | 11/2011 | Levy |
| 8,068,894 B2 | 11/2011 | Huizenga et al. |
| 8,073,541 B2 | 12/2011 | Alt et al. |
| 8,077,958 B2 | 12/2011 | Qian et al. |
| 8,078,274 B2 | 12/2011 | Kassab |
| 8,078,552 B2 | 12/2011 | Kaushal et al. |
| 8,082,032 B2 | 12/2011 | Kassab et al. |
| 8,082,353 B2 | 12/2011 | Huber et al. |
| 8,086,017 B2 | 12/2011 | He et al. |
| 8,086,294 B2 | 12/2011 | Echauz et al. |
| 8,089,853 B2 | 1/2012 | Dapper et al. |
| 8,094,551 B2 | 1/2012 | Huber et al. |
| 8,098,938 B1 | 1/2012 | Buddemeier et al. |
| 8,099,161 B2 | 1/2012 | Kassab |
| 8,103,333 B2 | 1/2012 | Tran |
| 8,107,726 B2 | 1/2012 | Xu et al. |
| 8,108,036 B2 | 1/2012 | Tran |
| 8,114,143 B2 | 2/2012 | Kassab et al. |
| 8,115,640 B2 | 2/2012 | Walls |
| 8,121,046 B2 | 2/2012 | Morrison et al. |
| 8,121,673 B2 | 2/2012 | Tran |
| 8,121,823 B2 | 2/2012 | Krebs et al. |
| 8,126,664 B2 | 2/2012 | Fournier et al. |
| 8,145,304 B2 | 3/2012 | Moffitt et al. |
| 8,149,649 B1 | 4/2012 | Brinn et al. |
| 8,160,701 B2 | 4/2012 | Zhao et al. |
| 8,164,345 B2 | 4/2012 | Bushnell et al. |
| 8,165,661 B2 | 4/2012 | Koski et al. |
| 8,165,916 B2 | 4/2012 | Hoffberg et al. |
| 8,170,333 B2 | 5/2012 | Balster et al. |
| 8,170,334 B2 | 5/2012 | Balster et al. |
| 8,170,335 B2 | 5/2012 | Balster et al. |
| 8,174,956 B2 | 5/2012 | Dapper et al. |
| 8,179,847 B2 | 5/2012 | Huber et al. |
| 8,183,062 B2 | 5/2012 | Funk et al. |
| 8,185,194 B2 | 5/2012 | Kassab |
| 8,190,194 B2 | 5/2012 | Brisebois |
| 8,190,543 B2 | 5/2012 | Kaushal et al. |
| 8,194,938 B2 | 6/2012 | Wechsler et al. |
| 8,194,986 B2 | 6/2012 | Conwell |
| 8,199,632 B2 | 6/2012 | Geile et al. |
| 8,200,506 B2 | 6/2012 | Kil |
| 8,204,697 B2 | 6/2012 | Garvey et al. |
| 8,208,697 B2 | 6/2012 | Schaffer et al. |
| 8,209,010 B2 | 6/2012 | Ryu et al. |
| 8,209,745 B2 | 6/2012 | Huber et al. |
| 8,213,398 B2 | 7/2012 | Geile et al. |
| 8,213,399 B2 | 7/2012 | Geile et al. |
| 8,214,033 B2 | 7/2012 | Snell et al. |
| 8,216,139 B2 | 7/2012 | Brauker et al. |
| 8,223,023 B2 | 7/2012 | Sachanandani et al. |
| 8,226,561 B2 | 7/2012 | McLaughlin et al. |
| 8,233,958 B2 | 7/2012 | Brauker et al. |
| 8,244,355 B2 | 8/2012 | Bennett et al. |
| 8,244,475 B2 | 8/2012 | Aguilar et al. |
| 8,249,698 B2 | 8/2012 | Mugler et al. |
| 8,251,906 B2 | 8/2012 | Brauker et al. |
| 8,251,911 B2 | 8/2012 | MacQuarrie et al. |
| 8,253,824 B2 | 8/2012 | Benezra et al. |
| 8,255,042 B2 | 8/2012 | MacQuarrie et al. |
| 8,257,259 B2 | 9/2012 | Brauker et al. |
| 8,262,582 B2 | 9/2012 | Kortelainen |
| 8,265,725 B2 | 9/2012 | Brauker et al. |
| 8,271,412 B2 | 9/2012 | Johnson |
| 8,275,463 B1 | 9/2012 | Andersen |
| 8,282,549 B2 | 10/2012 | Brauker et al. |
| 8,285,373 B2 | 10/2012 | Ternes et al. |
| 8,287,459 B2 | 10/2012 | Min et al. |
| 8,290,561 B2 | 10/2012 | Brauker et al. |
| 8,295,934 B2 | 10/2012 | Leyde |
| 8,301,241 B2 | 10/2012 | Ternes et al. |
| 8,301,406 B2 | 10/2012 | Lee et al. |
| 8,305,436 B2 | 11/2012 | Fujisawa et al. |
| 8,307,273 B2 | 11/2012 | Pea et al. |
| 8,315,150 B2 | 11/2012 | Geile et al. |
| 8,320,217 B1 | 11/2012 | Barger et al. |
| 8,321,003 B2 | 11/2012 | Zhang et al. |
| 8,323,188 B2 | 12/2012 | Tran |
| 8,323,189 B2 | 12/2012 | Tran et al. |
| 8,326,428 B2 | 12/2012 | Wenzel et al. |
| 8,326,429 B2 | 12/2012 | Wenzel et al. |
| 8,328,718 B2 | 12/2012 | Tran |
| 8,331,228 B2 | 12/2012 | Huber et al. |
| 8,346,360 B2 | 1/2013 | Libbus et al. |
| 8,351,321 B2 | 1/2013 | Dapper et al. |
| 8,355,579 B2 | 1/2013 | LeMoigne-Stewart et al. |
| 8,364,136 B2 | 1/2013 | Hoffberg et al. |
| 8,366,707 B2 | 2/2013 | Kassab et al. |
| 8,369,967 B2 | 2/2013 | Hoffberg et al. |
| 8,374,414 B2 | 2/2013 | Tang et al. |
| 8,374,667 B2 | 2/2013 | Brauker et al. |
| 8,374,696 B2 | 2/2013 | Sanchez et al. |
| 8,376,954 B2 | 2/2013 | Lange et al. |
| 8,376,964 B2 | 2/2013 | Park et al. |
| 8,380,308 B2 | 2/2013 | Rosenberg et al. |
| 8,388,604 B2 | 3/2013 | Kassab |
| 8,391,963 B2 | 3/2013 | Sternickel et al. |
| 8,396,582 B2 | 3/2013 | Kaushal et al. |
| 8,397,204 B2 | 3/2013 | Sengupta et al. |
| 8,401,640 B2 | 3/2013 | Zhao et al. |
| 8,403,865 B2 | 3/2013 | Halperin et al. |
| 8,406,115 B2 | 3/2013 | Dapper et al. |
| 8,406,522 B1 | 3/2013 | Owechko et al. |
| 8,406,867 B2 | 3/2013 | Kassab |
| 8,411,910 B2 | 4/2013 | Savvides et al. |
| 8,416,710 B2 | 4/2013 | Brisebois et al. |
| 8,423,125 B2 | 4/2013 | Rousso et al. |
| 8,425,415 B2 | 4/2013 | Tran |
| 8,427,649 B2 | 4/2013 | Hays et al. |
| 8,428,925 B2 | 4/2013 | Krebs et al. |
| 8,433,101 B2 | 4/2013 | Xu et al. |
| 8,435,167 B2 | 5/2013 | Oohashi et al. |
| 8,435,179 B2 | 5/2013 | Goode, Jr. et al. |
| 8,437,223 B2 | 5/2013 | Barger et al. |
| 8,437,844 B2 | 5/2013 | Syed Momen et al. |
| 8,437,998 B2 | 5/2013 | Routh et al. |
| 8,445,851 B2 | 5/2013 | Rousso et al. |
| 8,449,471 B2 | 5/2013 | Tran |
| 8,452,389 B2 | 5/2013 | Min |
| 8,456,309 B2 | 6/2013 | Sachanandani et al. |
| 8,461,988 B2 | 6/2013 | Tran |
| 8,463,441 B2 | 6/2013 | Zugibe et al. |
| 8,467,611 B2 | 6/2013 | Kumar et al. |
| 8,467,874 B2 | 6/2013 | Chen et al. |
| 8,467,884 B2 | 6/2013 | Chen et al. |
| 8,469,886 B2 | 6/2013 | Brauker et al. |
| 8,473,055 B2 | 6/2013 | Ryu et al. |
| 8,473,068 B2 | 6/2013 | Farazi |
| 8,475,367 B1 | 7/2013 | Yuen et al. |
| 8,475,368 B2 | 7/2013 | Tran et al. |
| 8,478,394 B2 | 7/2013 | Prichep et al. |
| 8,482,416 B2 | 7/2013 | Krans et al. |
| 8,486,690 B2 | 7/2013 | Burns |
| 8,488,863 B2 | 7/2013 | Boucheron |
| 8,489,247 B1 | 7/2013 | Engler |
| 8,491,492 B2 | 7/2013 | Shinar et al. |
| 8,494,829 B2 | 7/2013 | Teixeira |
| RE44,460 E | 8/2013 | Geile |
| 8,500,636 B2 | 8/2013 | Tran |
| 8,503,791 B2 | 8/2013 | Conwell |
| 8,509,881 B2 | 8/2013 | Thiagarajan et al. |
| 8,509,890 B2 | 8/2013 | Keel et al. |
| 8,515,126 B1 | 8/2013 | Medasani et al. |
| 8,515,534 B2 | 8/2013 | Ternes et al. |
| 8,515,535 B2 | 8/2013 | Hopper et al. |
| 8,516,266 B2 | 8/2013 | Hoffberg et al. |
| 8,517,953 B2 | 8/2013 | Lange et al. |
| 8,520,979 B2 | 8/2013 | Conwell |
| 8,522,312 B2 | 8/2013 | Huber et al. |
| 8,525,673 B2 | 9/2013 | Tran |
| 8,525,687 B2 | 9/2013 | Tran |

(56) References Cited

U.S. PATENT DOCUMENTS

| | | | |
|---|---|---|---|
| 8,527,324 | B2 | 9/2013 | Richter |
| 8,531,291 | B2 | 9/2013 | Tran |
| 8,532,770 | B2 | 9/2013 | Sweeney et al. |
| 8,536,133 | B2 | 9/2013 | DeNardo et al. |
| 8,540,651 | B2 | 9/2013 | Pfeffer et al. |
| 8,543,199 | B2 | 9/2013 | Snyder et al. |
| 8,547,824 | B2 | 10/2013 | Dapper et al. |
| 8,559,645 | B2 | 10/2013 | Corona-Strauss et al. |
| 8,560,134 | B1 | 10/2013 | Lee |
| 8,562,526 | B2 | 10/2013 | Heneghan et al. |
| 8,576,693 | B2 | 11/2013 | Dapper et al. |
| 8,577,451 | B2 | 11/2013 | Causevic |
| 8,577,822 | B2 | 11/2013 | Kusiak et al. |
| 8,582,916 | B2 | 11/2013 | Bar-Aviv et al. |
| 8,583,229 | B2 | 11/2013 | Rezai et al. |
| 8,583,230 | B2 | 11/2013 | Ryu et al. |
| 8,583,233 | B2 | 11/2013 | Betzold |
| 8,583,263 | B2 | 11/2013 | Hoffberg et al. |
| 8,585,607 | B2 | 11/2013 | Klap et al. |
| 8,586,932 | B2 | 11/2013 | Rousso et al. |
| 8,588,906 | B2 | 11/2013 | Ternes et al. |
| 8,588,933 | B2 | 11/2013 | Floyd et al. |
| 8,594,787 | B2 | 11/2013 | Crompvoets et al. |
| 8,594,805 | B2 | 11/2013 | Hincapie Ordonez et al. |
| 8,594,811 | B2 | 11/2013 | Chen et al. |
| 8,595,164 | B2 | 11/2013 | Dong et al. |
| 8,599,266 | B2 | 12/2013 | Trivedi et al. |
| 8,600,830 | B2 | 12/2013 | Hoffberg |
| 8,603,010 | B2 | 12/2013 | Lange et al. |
| 8,605,970 | B2 | 12/2013 | Bar-Aviv et al. |
| 8,606,021 | B2 | 12/2013 | Conwell |
| 8,606,349 | B2 | 12/2013 | Rousso et al. |
| 8,606,418 | B1 | 12/2013 | Myers et al. |
| 8,611,692 | B2 | 12/2013 | Nimnual et al. |
| 8,617,082 | B2 | 12/2013 | Zhang et al. |
| 8,620,426 | B2 | 12/2013 | Moffitt et al. |
| 8,620,427 | B2 | 12/2013 | Libbus et al. |
| 8,620,660 | B2 | 12/2013 | Yen et al. |
| 8,626,274 | B2 | 1/2014 | Chiu et al. |
| 8,626,281 | B2 | 1/2014 | Ternes et al. |
| 8,630,707 | B2 | 1/2014 | Zhao et al. |
| 8,632,469 | B2 | 1/2014 | Kassab |
| 8,634,930 | B2 | 1/2014 | Dalal et al. |
| 8,635,051 | B1 | 1/2014 | Wu et al. |
| 8,638,655 | B2 | 1/2014 | Geile |
| 8,645,832 | B2 | 2/2014 | Pea et al. |
| 8,648,959 | B2 | 2/2014 | Capata et al. |
| 8,649,565 | B1 | 2/2014 | Kim et al. |
| 8,649,853 | B2 | 2/2014 | Sweeney et al. |
| 8,652,038 | B2 | 2/2014 | Tran et al. |
| 8,657,745 | B2 | 2/2014 | Brauker et al. |
| 8,659,697 | B2 | 2/2014 | Capata et al. |
| 8,677,505 | B2 | 3/2014 | Redlich et al. |
| 8,678,943 | B2 | 3/2014 | Mooney |
| 8,679,018 | B2 | 3/2014 | McLaughlin et al. |
| 8,679,030 | B2 | 3/2014 | Shinar et al. |
| 8,679,034 | B2 | 3/2014 | Halperin et al. |
| 8,680,991 | B2 | 3/2014 | Tran |
| 8,684,900 | B2 | 4/2014 | Tran |
| 8,684,922 | B2 | 4/2014 | Tran |
| 8,684,925 | B2 | 4/2014 | Manicka et al. |
| 8,696,569 | B2 | 4/2014 | Yuen et al. |
| 8,700,137 | B2 | 4/2014 | Albert |
| 8,700,146 | B2 | 4/2014 | Ternes et al. |
| 8,702,616 | B2 | 4/2014 | Gill et al. |
| 8,702,629 | B2 | 4/2014 | Giuffrida et al. |
| 8,706,204 | B2 | 4/2014 | Seo et al. |
| 8,708,903 | B2 | 4/2014 | Tran |
| 8,712,507 | B2 | 4/2014 | Cazares et al. |
| 8,713,025 | B2 | 4/2014 | Eder |
| 8,714,983 | B2 | 5/2014 | Kil |
| 8,725,243 | B2 | 5/2014 | Dilorenzo et al. |
| 8,725,507 | B2 | 5/2014 | Cortez et al. |
| 8,725,667 | B2 | 5/2014 | Kaushal et al. |
| 8,727,978 | B2 | 5/2014 | Tran et al. |
| 8,731,646 | B2 | 5/2014 | Halperin et al. |
| 8,734,360 | B2 | 5/2014 | Klap et al. |
| 8,738,111 | B2 | 5/2014 | Sweeney et al. |
| 8,738,119 | B2 | 5/2014 | Zhang et al. |
| 8,743,776 | B2 | 6/2014 | Gurajala et al. |
| 8,744,557 | B2 | 6/2014 | Sternickel et al. |
| 8,744,607 | B2 | 6/2014 | Kaushal et al. |
| 8,747,312 | B2 | 6/2014 | Yuen et al. |
| 8,747,313 | B2 | 6/2014 | Tran et al. |
| 8,747,315 | B2 | 6/2014 | Brauker et al. |
| 8,747,336 | B2 | 6/2014 | Tran |
| 8,750,971 | B2 | 6/2014 | Tran |
| 8,750,981 | B2 | 6/2014 | Bornzin et al. |
| 8,750,992 | B2 | 6/2014 | Hopper et al. |
| 8,755,837 | B2 | 6/2014 | Rhoads et al. |
| 8,755,916 | B2 | 6/2014 | Lou |
| 8,755,940 | B2 | 6/2014 | Lou et al. |
| 8,761,051 | B2 | 6/2014 | Brisebois et al. |
| 8,761,893 | B2 | 6/2014 | Klefenz et al. |
| 8,761,903 | B2 | 6/2014 | Chen et al. |
| 8,762,065 | B2 | 6/2014 | DiLorenzo |
| 8,764,651 | B2 | 7/2014 | Tran |
| 8,764,653 | B2 | 7/2014 | Kaminska et al. |
| 8,764,661 | B2 | 7/2014 | McLaughlin et al. |
| 8,768,461 | B2 | 7/2014 | Stein |
| 8,775,134 | B2 | 7/2014 | Gielis |
| 8,775,143 | B2 | 7/2014 | Routh et al. |
| 8,781,597 | B2 | 7/2014 | DiLorenzo |
| 8,786,624 | B2 | 7/2014 | Echauz et al. |
| 8,790,264 | B2 | 7/2014 | Sandler et al. |
| 8,792,974 | B2 | 7/2014 | Rothman |
| 8,792,998 | B2 | 7/2014 | Xi et al. |
| 8,797,448 | B2 | 8/2014 | Capata et al. |
| 8,797,550 | B2 | 8/2014 | Hays et al. |
| 8,798,714 | B2 | 8/2014 | Henning |
| 8,798,726 | B2 | 8/2014 | Kang et al. |
| 8,798,731 | B2 | 8/2014 | Keel et al. |
| 8,801,610 | B2 | 8/2014 | Brauker et al. |
| 8,810,796 | B2 | 8/2014 | Hays et al. |
| 8,811,977 | B2 | 8/2014 | Austin et al. |
| 8,818,404 | B2 | 8/2014 | Brisebois |
| 8,818,524 | B2 | 8/2014 | Hincapie Ordonez et al. |
| 8,818,778 | B2 | 8/2014 | Salazar-Tio et al. |
| 8,821,403 | B2 | 9/2014 | Sharrock |
| 8,821,418 | B2 | 9/2014 | Meger et al. |
| 8,826,199 | B2 | 9/2014 | Sedaghat et al. |
| 8,827,918 | B2 | 9/2014 | Kim et al. |
| 8,831,705 | B2 | 9/2014 | Dobak |
| 8,834,364 | B2 | 9/2014 | Heneghan et al. |
| 8,838,510 | B2 | 9/2014 | Baughman et al. |
| 8,840,564 | B2 | 9/2014 | Pinhas et al. |
| 8,842,136 | B2 | 9/2014 | Kuo et al. |
| 8,849,390 | B2 | 9/2014 | Echauz et al. |
| 8,849,575 | B2 | 9/2014 | Gustafsson et al. |
| 8,849,629 | B2 | 9/2014 | Brown et al. |
| 8,849,737 | B1 | 9/2014 | Engler |
| 8,850,048 | B2 | 9/2014 | Huber et al. |
| 8,855,011 | B2 | 10/2014 | Ortega et al. |
| 8,855,372 | B2 | 10/2014 | Rodriguez et al. |
| 8,855,775 | B2 | 10/2014 | Leyde |
| 8,855,980 | B2 | 10/2014 | Brown et al. |
| 8,856,716 | B1 | 10/2014 | Huang et al. |
| 8,858,449 | B2 | 10/2014 | Inan et al. |
| 8,860,793 | B2 | 10/2014 | Lo et al. |
| 8,861,799 | B2 | 10/2014 | Savvides et al. |
| 8,862,226 | B2 | 10/2014 | Ternes et al. |
| 8,862,231 | B2 | 10/2014 | Kirchner et al. |
| 8,862,627 | B2 | 10/2014 | Ferringer et al. |
| 8,866,322 | B2 | 10/2014 | Tchoryk, Jr. et al. |
| 8,866,936 | B2 | 10/2014 | Barbu |
| 8,868,172 | B2 | 10/2014 | Leyde et al. |
| 8,870,780 | B2 | 10/2014 | Inan et al. |
| 8,873,813 | B2 | 10/2014 | Tadayon et al. |
| 8,873,853 | B2 | 10/2014 | Rodriguez |
| 8,874,203 | B2 | 10/2014 | Kassab et al. |
| 8,874,477 | B2 | 10/2014 | Hoffberg |
| 8,880,156 | B2 | 11/2014 | Crompvoets et al. |
| 8,880,158 | B2 | 11/2014 | Spector |
| 8,882,684 | B2 | 11/2014 | Halperin et al. |

(56) References Cited

U.S. PATENT DOCUMENTS

| | | |
|---|---|---|
| 8,882,765 B2 | 11/2014 | Kassab et al. |
| 8,886,301 B2 | 11/2014 | Kassab |
| 8,886,311 B2 | 11/2014 | Anderson et al. |
| 8,888,710 B2 | 11/2014 | Wariar et al. |
| 8,892,413 B2 | 11/2014 | Routh et al. |
| 8,897,586 B2 | 11/2014 | Dorairaj |
| 8,897,869 B2 | 11/2014 | Kassab |
| 8,903,997 B2 | 12/2014 | Hobbs |
| 8,905,928 B2 | 12/2014 | Hayes et al. |
| 8,909,329 B2 | 12/2014 | Prakash et al. |
| 8,913,839 B2 | 12/2014 | Ricanek, Jr. et al. |
| 8,918,169 B2 | 12/2014 | Kassab et al. |
| 8,918,172 B2 | 12/2014 | Moffitt et al. |
| 8,922,856 B2 | 12/2014 | Yanai et al. |
| 8,923,958 B2 | 12/2014 | Gupta et al. |
| 8,923,965 B2 | 12/2014 | Min et al. |
| 8,923,981 B2 | 12/2014 | Grill, Jr. et al. |
| 8,934,970 B2 | 1/2015 | Ternes et al. |
| 8,938,113 B2 | 1/2015 | Kovalan et al. |
| 8,942,180 B2 | 1/2015 | Gurajala et al. |
| 8,942,779 B2 | 1/2015 | Halperin et al. |
| 8,942,799 B2 | 1/2015 | Ternes et al. |
| 8,945,875 B2 | 2/2015 | Roessler et al. |
| 8,948,442 B2 | 2/2015 | Breed et al. |
| 8,954,146 B2 | 2/2015 | Hopper et al. |
| 8,961,185 B2 | 2/2015 | Bleich et al. |
| 8,965,044 B1 | 2/2015 | Owechko et al. |
| 8,968,195 B2 | 3/2015 | Tran |
| 8,972,861 B2 | 3/2015 | Pea et al. |
| 8,976,856 B2 | 3/2015 | Haskell |
| 8,979,730 B2 | 3/2015 | Naujokat et al. |
| 8,979,731 B2 | 3/2015 | Aarts et al. |
| 8,983,854 B2 | 3/2015 | Park et al. |
| 8,990,688 B2 | 3/2015 | Lee et al. |
| 8,990,740 B2 | 3/2015 | Zhang et al. |
| 8,992,434 B2 | 3/2015 | Halperin et al. |
| 8,995,074 B1 | 3/2015 | Low |
| 8,996,107 B2 | 3/2015 | Libbus et al. |
| 8,996,110 B2 | 3/2015 | Sison et al. |
| 8,996,442 B2 | 3/2015 | Gould et al. |
| 8,998,820 B2 | 4/2015 | Jarverud et al. |
| 8,998,830 B2 | 4/2015 | Halperin et al. |
| 9,002,446 B2 | 4/2015 | Wenzel et al. |
| 9,002,453 B2 | 4/2015 | Keel et al. |
| 9,002,483 B1 | 4/2015 | Engler |
| 9,002,682 B2 | 4/2015 | Kasabov |
| 9,008,367 B2 | 4/2015 | Tolkowsky et al. |
| 9,008,754 B2 | 4/2015 | Steinberg et al. |
| 9,008,762 B2 | 4/2015 | Brockway et al. |
| 9,009,670 B2 | 4/2015 | Precious et al. |
| 9,011,338 B2 | 4/2015 | Park et al. |
| 9,011,346 B2 | 4/2015 | Wiard et al. |
| 9,014,453 B2 | 4/2015 | Steinberg et al. |
| 9,014,789 B2 | 4/2015 | Mercader et al. |
| 9,014,790 B2 | 4/2015 | Richards et al. |
| 9,014,809 B2 | 4/2015 | Wenzel et al. |
| 9,015,093 B1 | 4/2015 | Commons |
| 9,015,145 B2 | 4/2015 | Lim et al. |
| 9,017,691 B2 | 4/2015 | Barouch et al. |
| 9,019,819 B2 | 4/2015 | Huber et al. |
| 9,020,585 B2 | 4/2015 | John et al. |
| RE45,512 E | 5/2015 | Tearney et al. |
| 9,022,564 B2 | 5/2015 | Watanabe et al. |
| 9,023,984 B2 | 5/2015 | Hutton et al. |
| 9,026,193 B2 | 5/2015 | Pahlevan et al. |
| 9,026,199 B2 | 5/2015 | Halperin et al. |
| 9,026,200 B2 | 5/2015 | Nagata et al. |
| 9,026,201 B2 | 5/2015 | Zhang et al. |
| 9,026,202 B2 | 5/2015 | Albert |
| 9,026,214 B2 | 5/2015 | Ternes et al. |
| 9,028,405 B2 | 5/2015 | Tran |
| 9,028,407 B1 | 5/2015 | Bennett-Guerrero |
| 9,029,413 B2 | 5/2015 | Munger et al. |
| 9,031,301 B2 | 5/2015 | Imamura et al. |
| 9,031,642 B2 | 5/2015 | Ghosh |
| 9,031,649 B2 | 5/2015 | Ousdigian |
| 9,033,883 B2 | 5/2015 | Wang et al. |
| 9,033,887 B2 | 5/2015 | Ionasec et al. |
| 9,033,893 B2 | 5/2015 | Spector |
| 9,037,223 B2 | 5/2015 | Oral et al. |
| 9,037,224 B1 | 5/2015 | Fu |
| 9,042,619 B2 | 5/2015 | Zheng et al. |
| 9,042,952 B2 | 5/2015 | Lynn et al. |
| 9,042,958 B2 | 5/2015 | Karmarkar et al. |
| 9,044,144 B2 | 6/2015 | Figgatt et al. |
| 9,044,149 B2 | 6/2015 | Richards et al. |
| 9,044,171 B2 | 6/2015 | Venkatraman et al. |
| 9,044,558 B2 | 6/2015 | Baker, Jr. et al. |
| 9,047,272 B1 | 6/2015 | To |
| 9,047,353 B2 | 6/2015 | Kumar |
| 9,049,981 B2 | 6/2015 | Patangay et al. |
| 9,049,985 B2 | 6/2015 | Feher |
| 9,050,007 B1 | 6/2015 | Brockway et al. |
| 9,050,014 B2 | 6/2015 | Zhang |
| 9,051,379 B2 | 6/2015 | Wolf et al. |
| 9,053,416 B1 | 6/2015 | De Leo et al. |
| 9,055,871 B2 | 6/2015 | Inan et al. |
| 9,055,884 B2 | 6/2015 | Piferi et al. |
| 9,056,172 B2 | 6/2015 | Shelly et al. |
| 9,060,669 B1 | 6/2015 | Mo et al. |
| 9,060,683 B2 | 6/2015 | Tran |
| 9,060,689 B2 | 6/2015 | Tearney et al. |
| 9,060,695 B2 | 6/2015 | Peters |
| 9,060,722 B2 | 6/2015 | Teixeira |
| 9,060,733 B2 | 6/2015 | Bruder et al. |
| 9,063,139 B2 | 6/2015 | Allikmets et al. |
| 9,066,672 B2 | 6/2015 | Kassab et al. |
| 9,066,679 B2 | 6/2015 | Beach et al. |
| 9,066,680 B1 | 6/2015 | Al-Ali et al. |
| 9,066,686 B2 | 6/2015 | Lasser et al. |
| 9,066,708 B2 | 6/2015 | Kassab |
| 9,069,130 B2 | 6/2015 | Yun et al. |
| 9,072,437 B2 | 7/2015 | Paalasmaa |
| 9,072,438 B2 | 7/2015 | Brockway et al. |
| 9,075,446 B2 | 7/2015 | Garudadri et al. |
| 9,076,202 B2 | 7/2015 | Courtney et al. |
| 9,079,060 B2 | 7/2015 | Hong et al. |
| 9,081,148 B2 | 7/2015 | Tearney et al. |
| 9,084,531 B2 | 7/2015 | Chen et al. |
| 9,084,576 B2 | 7/2015 | Guracar |
| 9,084,611 B2 | 7/2015 | Amirana et al. |
| 9,086,467 B2 | 7/2015 | Elgort et al. |
| 9,087,368 B2 | 7/2015 | Tearney et al. |
| 9,089,269 B2 | 7/2015 | Narayan et al. |
| 9,092,691 B1 | 7/2015 | Beaumont et al. |
| 9,095,266 B1 | 8/2015 | Fu |
| 9,095,313 B2 | 8/2015 | Tolkowsky et al. |
| 9,095,505 B2 | 8/2015 | Hertle |
| 9,097,756 B2 | 8/2015 | Piferi |
| 9,101,286 B2 | 8/2015 | Tolkowsky et al. |
| 9,101,772 B2 | 8/2015 | Kleckner et al. |
| 9,107,571 B2 | 8/2015 | Strauss et al. |
| 9,107,584 B2 | 8/2015 | Wohlschlager et al. |
| 9,107,586 B2 | 8/2015 | Tran |
| 9,107,623 B2 | 8/2015 | Brauker et al. |
| 9,107,624 B2 | 8/2015 | Darty |
| 9,113,794 B2 | 8/2015 | Hong et al. |
| 9,113,795 B2 | 8/2015 | Hong et al. |
| 9,113,826 B2 | 8/2015 | Osumi |
| 9,113,830 B2 | 8/2015 | Galen et al. |
| 9,114,260 B2 | 8/2015 | Pless et al. |
| 9,116,835 B1 | 8/2015 | Smyth |
| RE45,660 E | 9/2015 | Weiner et al. |
| 9,119,547 B2 | 9/2015 | Cazares et al. |
| 9,119,573 B2 | 9/2015 | Lu et al. |
| 9,121,801 B2 | 9/2015 | Clark et al. |
| 9,125,574 B2 | 9/2015 | Zia et al. |
| 9,125,577 B2 | 9/2015 | Sameni et al. |
| 9,125,578 B2 | 9/2015 | Grunwald |
| 9,126,050 B2 | 9/2015 | Simon et al. |
| 9,131,852 B2 | 9/2015 | Li et al. |
| 9,131,864 B2 | 9/2015 | Korenberg |
| 9,131,902 B2 | 9/2015 | Halperin et al. |
| 9,136,980 B2 | 9/2015 | Baheti et al. |

(56) References Cited

U.S. PATENT DOCUMENTS

| | | |
|---|---|---|
| 9,138,150 B2 | 9/2015 | Boschetti Sacco et al. |
| 9,144,394 B2 | 9/2015 | Cohen et al. |
| 9,147,268 B2 | 9/2015 | Chen et al. |
| 9,148,839 B2 | 9/2015 | Hejazi et al. |
| RE45,725 E | 10/2015 | Mugler, III et al. |
| 9,149,219 B2 | 10/2015 | Goode, Jr. et al. |
| 9,149,231 B2 | 10/2015 | Fujita et al. |
| 9,149,244 B2 | 10/2015 | Anderson |
| 9,149,645 B2 | 10/2015 | Sanghera et al. |
| 9,155,482 B2 | 10/2015 | Anderson et al. |
| 9,155,484 B2 | 10/2015 | Baker et al. |
| 9,155,893 B2 | 10/2015 | Zhou et al. |
| 9,161,705 B2 | 10/2015 | Tamil et al. |
| 9,162,074 B2 | 10/2015 | Allavatam et al. |
| 9,163,216 B1 | 10/2015 | Hickman et al. |
| 9,164,481 B2 | 10/2015 | Tsang |
| 9,167,971 B2 | 10/2015 | Ahmad et al. |
| 9,168,290 B2 | 10/2015 | Heifetz |
| 9,168,380 B1 | 10/2015 | Greenhut et al. |
| 9,168,385 B2 | 10/2015 | Snyder |
| 9,168,419 B2 | 10/2015 | Hong et al. |
| 9,171,250 B2 | 10/2015 | Wang et al. |
| 9,171,353 B2 | 10/2015 | Vija et al. |
| 9,173,566 B2 | 11/2015 | Feher |
| 9,173,579 B2 | 11/2015 | Berkow |
| 9,173,909 B2 | 11/2015 | Lee |
| 9,174,061 B2 | 11/2015 | Freeman et al. |
| 9,175,095 B2 | 11/2015 | Deisseroth et al. |
| 9,176,319 B2 | 11/2015 | Bouma et al. |
| 9,178,330 B2 | 11/2015 | Oh et al. |
| 9,179,890 B2 | 11/2015 | Ionasec et al. |
| 9,180,043 B2 | 11/2015 | Merrill et al. |
| 9,180,300 B2 | 11/2015 | Sambelashvili et al. |
| 9,183,351 B2 | 11/2015 | Shusterman |
| 9,183,626 B2 | 11/2015 | Zhao et al. |
| 9,186,066 B2 | 11/2015 | Tearney et al. |
| 9,186,067 B2 | 11/2015 | Tearney et al. |
| 9,186,068 B2 | 11/2015 | Li et al. |
| 9,186,079 B2 | 11/2015 | Mase et al. |
| 9,186,105 B2 | 11/2015 | Leininger et al. |
| 9,186,106 B2 | 11/2015 | Osorio |
| 9,186,521 B2 | 11/2015 | Quan et al. |
| 9,189,733 B2 | 11/2015 | Thompson et al. |
| 9,192,328 B2 | 11/2015 | Brauker et al. |
| 9,192,336 B2 | 11/2015 | Addison et al. |
| 9,192,446 B2 | 11/2015 | Piferi et al. |
| 9,193,442 B1 | 11/2015 | Young et al. |
| 9,195,949 B2 | 11/2015 | Kasabov |
| 9,197,173 B2 | 11/2015 | Denison et al. |
| 9,198,582 B2 | 12/2015 | Watson et al. |
| 9,198,586 B2 | 12/2015 | Melker |
| 9,198,604 B2 | 12/2015 | Venkatraman et al. |
| 9,198,616 B2 | 12/2015 | Addison et al. |
| 9,198,634 B2 | 12/2015 | Pretorius et al. |
| 9,199,078 B1 | 12/2015 | Gunderson |
| 9,201,902 B2 | 12/2015 | Doi et al. |
| 9,202,008 B1 | 12/2015 | Frederick et al. |
| 9,204,796 B2 | 12/2015 | Tran |
| 9,208,173 B1 | 12/2015 | Doi et al. |
| 9,208,557 B2 | 12/2015 | Pautot |
| 9,208,587 B2 | 12/2015 | Hardy et al. |
| 9,209,782 B2 | 12/2015 | Ricci et al. |
| 9,211,413 B2 | 12/2015 | Ziegler et al. |
| 9,213,990 B2 | 12/2015 | Adjaoute |
| 9,215,298 B2 | 12/2015 | Schiff |
| 9,215,980 B2 | 12/2015 | Tran et al. |
| 9,215,987 B2 | 12/2015 | Trayanova et al. |
| 9,215,991 B2 | 12/2015 | Inan et al. |
| 9,216,001 B2 | 12/2015 | Owen et al. |
| 9,216,065 B2 | 12/2015 | Cohen et al. |
| 9,218,181 B1 | 12/2015 | Chmiel et al. |
| 9,220,440 B2 | 12/2015 | Addison et al. |
| 9,220,455 B2 | 12/2015 | Sarrafzadeh et al. |
| 9,220,459 B2 | 12/2015 | Addison et al. |
| 9,220,460 B2 | 12/2015 | Addison et al. |
| 9,220,467 B2 | 12/2015 | Wu et al. |
| 9,220,856 B2 | 12/2015 | Martin et al. |
| 9,223,569 B1 | 12/2015 | Chmiel et al. |
| 9,226,660 B2 | 1/2016 | de Boer et al. |
| 9,226,665 B2 | 1/2016 | Tearney et al. |
| 9,226,676 B2 | 1/2016 | Chiu |
| 9,236,046 B2 | 1/2016 | Watson et al. |
| 9,237,855 B2 | 1/2016 | Hong et al. |
| 9,239,951 B2 | 1/2016 | Hoffberg et al. |
| 9,241,667 B2 | 1/2016 | Narayan et al. |
| 9,242,090 B2 | 1/2016 | Atalar et al. |
| 9,242,095 B2 | 1/2016 | Grill, Jr. et al. |
| 9,245,091 B2 | 1/2016 | Voigt et al. |
| 9,247,901 B2 | 2/2016 | Kamath et al. |
| 9,248,288 B2 | 2/2016 | Panken et al. |
| 9,248,306 B2 | 2/2016 | Joo et al. |
| 9,249,200 B2 | 2/2016 | Deisseroth et al. |
| 9,254,089 B2 | 2/2016 | Tearney et al. |
| 9,254,093 B2 | 2/2016 | Spector |
| 9,254,095 B2 | 2/2016 | Galloway et al. |
| 9,254,102 B2 | 2/2016 | Tearney et al. |
| 9,254,383 B2 | 2/2016 | Simon et al. |
| 9,256,701 B2 | 2/2016 | Chen et al. |
| 9,258,199 B2 | 2/2016 | Kalika et al. |
| 9,258,561 B2 | 2/2016 | Amon et al. |
| 9,259,167 B2 | 2/2016 | Lo et al. |
| 9,259,579 B2 | 2/2016 | Grill et al. |
| 9,259,591 B2 | 2/2016 | Brown et al. |
| 9,261,573 B1 | 2/2016 | Radparvar et al. |
| 9,262,826 B2 | 2/2016 | Khachaturian et al. |
| 9,264,877 B2 | 2/2016 | Feher |
| 9,267,936 B2 | 2/2016 | Hickman et al. |
| 9,269,127 B2 | 2/2016 | Ding et al. |
| RE45,922 E | 3/2016 | Marcovecchio et al. |
| 9,277,871 B2 | 3/2016 | Keenan et al. |
| 9,277,956 B2 | 3/2016 | Zhang |
| 9,278,226 B2 | 3/2016 | Olson |
| 9,282,896 B2 | 3/2016 | Crawley et al. |
| 9,282,902 B2 | 3/2016 | Richards et al. |
| 9,282,908 B2 | 3/2016 | Spector |
| 9,282,910 B2 | 3/2016 | Narayan et al. |
| 9,282,911 B2 | 3/2016 | Stickney et al. |
| 9,282,925 B2 | 3/2016 | Kamath et al. |
| 9,282,931 B2 | 3/2016 | Tearney et al. |
| 9,286,662 B2 | 3/2016 | Wang et al. |
| 9,287,939 B2 | 3/2016 | Xu et al. |
| 9,289,133 B2 | 3/2016 | Cohen et al. |
| 9,289,136 B2 | 3/2016 | Addison et al. |
| 9,289,150 B1 | 3/2016 | Gupta et al. |
| 9,289,165 B2 | 3/2016 | Soykan et al. |
| 9,289,167 B2 | 3/2016 | Diab et al. |
| 9,289,471 B2 | 3/2016 | White |
| 9,289,545 B2 | 3/2016 | Olde et al. |
| 9,294,074 B2 | 3/2016 | Brockway |
| 9,295,391 B1 | 3/2016 | Tearney et al. |
| 9,301,703 B2 | 4/2016 | Sato |
| 9,301,705 B2 | 4/2016 | Halperin et al. |
| 9,302,111 B2 | 4/2016 | John et al. |
| 9,304,121 B2 | 4/2016 | Tearney et al. |
| 9,305,334 B2 | 4/2016 | Barzelay et al. |
| 9,305,350 B2 | 4/2016 | Crawley et al. |
| 9,307,407 B1 | 4/2016 | Feher |
| 9,307,917 B2 | 4/2016 | Hong et al. |
| 9,308,042 B2 | 4/2016 | Whayne et al. |
| 9,308,052 B2 | 4/2016 | Tolkowsky |
| 9,314,181 B2 | 4/2016 | Brockway et al. |
| 9,314,305 B2 | 4/2016 | Jenkins et al. |
| 9,317,626 B2 | 4/2016 | Chan |
| 9,317,740 B2 | 4/2016 | Ricanek, Jr. et al. |
| 9,319,028 B2 | 4/2016 | Ricci et al. |
| 9,319,212 B2 | 4/2016 | Feher |
| 9,320,491 B2 | 4/2016 | Konofagou et al. |
| 9,321,544 B2 | 4/2016 | Thompson et al. |
| 9,323,890 B2 | 4/2016 | Hayashi |
| 9,324,005 B2 | 4/2016 | Wadhwa et al. |
| 9,324,141 B2 | 4/2016 | Begin |
| 9,324,144 B2 | 4/2016 | Khachaturian et al. |
| 9,325,348 B2 | 4/2016 | Moroz et al. |
| 9,326,682 B2 | 5/2016 | Tearney et al. |

(56) References Cited

U.S. PATENT DOCUMENTS

| | | |
|---|---|---|
| 9,326,697 B2 | 5/2016 | Linker |
| 9,326,722 B2 | 5/2016 | Young |
| 9,327,130 B2 | 5/2016 | Marculescu et al. |
| 9,330,092 B2 | 5/2016 | Vakoc et al. |
| 9,330,459 B2 | 5/2016 | Crawley et al. |
| 9,332,357 B2 | 5/2016 | Adachi et al. |
| 9,332,939 B2 | 5/2016 | Osorio |
| 9,332,942 B2 | 5/2016 | Jaffer et al. |
| 9,339,202 B2 | 5/2016 | Brockway et al. |
| 9,339,206 B2 | 5/2016 | Grunwald |
| 9,339,230 B2 | 5/2016 | Kassab |
| 9,339,241 B2 | 5/2016 | Najarian et al. |
| 9,339,436 B2 | 5/2016 | Freeman et al. |
| 9,339,662 B2 | 5/2016 | Allavatam et al. |
| 9,340,589 B2 | 5/2016 | Deisseroth et al. |
| 9,341,783 B2 | 5/2016 | Namati et al. |
| 9,345,413 B2 | 5/2016 | Schie et al. |
| 9,345,609 B2 | 5/2016 | Hyde et al. |
| 9,345,888 B2 | 5/2016 | Wedan et al. |
| 9,351,640 B2 | 5/2016 | Tran |
| 9,351,642 B2 | 5/2016 | Nadkarni et al. |
| 9,351,649 B2 | 5/2016 | Mestha et al. |
| 9,351,661 B2 | 5/2016 | Kassab |
| 9,351,668 B2 | 5/2016 | Brauker et al. |
| 9,351,674 B2 | 5/2016 | Baker, Jr. |
| 9,352,057 B2 | 5/2016 | Ahrens et al. |
| 9,352,165 B2 | 5/2016 | Zhang |
| 9,354,115 B2 | 5/2016 | Darty |
| 9,356,731 B2 | 5/2016 | Baheti et al. |
| 2001/0028743 A1 | 10/2001 | Kostrzewski et al. |
| 2002/0009756 A1 | 1/2002 | Mandell et al. |
| 2002/0015532 A1 | 2/2002 | Kostrzewski et al. |
| 2002/0032386 A1 | 3/2002 | Sackner et al. |
| 2002/0040192 A1 | 4/2002 | Prutchi |
| 2002/0054694 A1 | 5/2002 | Vachtsevanos et al. |
| 2002/0059022 A1 | 5/2002 | Breed et al. |
| 2002/0082756 A1 | 6/2002 | Breed et al. |
| 2002/0123975 A1 | 9/2002 | Poluzzi et al. |
| 2002/0138014 A1* | 9/2002 | Baura .................. A61B 5/029 600/526 |
| 2002/0151992 A1 | 10/2002 | Hoffberg et al. |
| 2002/0165854 A1 | 11/2002 | Blayvas et al. |
| 2002/0173936 A1 | 11/2002 | Srinivasan et al. |
| 2002/0176624 A1 | 11/2002 | Kostrzewski et al. |
| 2002/0186875 A1 | 12/2002 | Burmer et al. |
| 2002/0194159 A1 | 12/2002 | Kamath et al. |
| 2003/0036835 A1 | 2/2003 | Breed et al. |
| 2003/0045806 A1 | 3/2003 | Brydon |
| 2003/0055799 A1 | 3/2003 | Starzyk |
| 2003/0059837 A1 | 3/2003 | Levinson et al. |
| 2003/0061228 A1 | 3/2003 | Kamath et al. |
| 2003/0081836 A1 | 5/2003 | Averbuch et al. |
| 2003/0086593 A1 | 5/2003 | Liu et al. |
| 2003/0101164 A1 | 5/2003 | Pic et al. |
| 2003/0135097 A1 | 7/2003 | Wiederhold et al. |
| 2003/0135109 A1 | 7/2003 | Raghavan et al. |
| 2003/0135127 A1 | 7/2003 | Sackner et al. |
| 2003/0176656 A1 | 9/2003 | Mandell et al. |
| 2003/0200189 A1 | 10/2003 | Meng et al. |
| 2003/0208451 A1 | 11/2003 | Liaw |
| 2003/0209893 A1 | 11/2003 | Breed et al. |
| 2003/0217047 A1 | 11/2003 | Marchisio |
| 2003/0228565 A1 | 12/2003 | Oestreicher et al. |
| 2003/0233034 A1 | 12/2003 | Varri et al. |
| 2003/0233132 A1 | 12/2003 | Pastore et al. |
| 2004/0019470 A1 | 1/2004 | Card et al. |
| 2004/0045030 A1 | 3/2004 | Reynolds et al. |
| 2004/0068199 A1 | 4/2004 | Echauz et al. |
| 2004/0097802 A1 | 5/2004 | Cohen |
| 2004/0125121 A1 | 7/2004 | Pea et al. |
| 2004/0125133 A1 | 7/2004 | Pea et al. |
| 2004/0125148 A1 | 7/2004 | Pea et al. |
| 2004/0129478 A1 | 7/2004 | Breed et al. |
| 2004/0133355 A1 | 7/2004 | Schneider |
| 2004/0138578 A1 | 7/2004 | Pineda et al. |
| 2004/0207548 A1 | 10/2004 | Kilbank |
| 2004/0225629 A1 | 11/2004 | Eder |
| 2004/0225649 A1 | 11/2004 | Yeo et al. |
| 2004/0229210 A1 | 11/2004 | Sabry et al. |
| 2004/0230131 A1 | 11/2004 | Kassab et al. |
| 2004/0243567 A1 | 12/2004 | Levy |
| 2004/0267086 A1 | 12/2004 | Anstadt et al. |
| 2005/0008179 A1 | 1/2005 | Quinn |
| 2005/0017488 A1 | 1/2005 | Breed et al. |
| 2005/0021101 A1 | 1/2005 | Chen et al. |
| 2005/0026199 A1 | 2/2005 | Shaw |
| 2005/0027457 A1 | 2/2005 | Mandell et al. |
| 2005/0046584 A1 | 3/2005 | Breed |
| 2005/0069162 A1 | 3/2005 | Haykin et al. |
| 2005/0075846 A1 | 4/2005 | Kim |
| 2005/0076190 A1 | 4/2005 | Shaw |
| 2005/0079524 A1 | 4/2005 | Shaw |
| 2005/0089923 A9 | 4/2005 | Levinson et al. |
| 2005/0102246 A1 | 5/2005 | Movellan et al. |
| 2005/0113666 A1 | 5/2005 | Bonmassar et al. |
| 2005/0114078 A1 | 5/2005 | Srinivasan et al. |
| 2005/0119454 A1 | 6/2005 | Mandell et al. |
| 2005/0124864 A1 | 6/2005 | Mack et al. |
| 2005/0131607 A1 | 6/2005 | Breed |
| 2005/0131660 A1 | 6/2005 | Yadegar et al. |
| 2005/0137480 A1 | 6/2005 | Alt et al. |
| 2005/0144284 A1 | 6/2005 | Ludwig et al. |
| 2005/0156775 A1 | 7/2005 | Petre et al. |
| 2005/0158736 A1 | 7/2005 | Shaw |
| 2005/0183958 A1 | 8/2005 | Wikiel et al. |
| 2005/0196047 A1 | 9/2005 | Owechko et al. |
| 2005/0197590 A1 | 9/2005 | Osorio et al. |
| 2005/0203360 A1 | 9/2005 | Brauker et al. |
| 2005/0203434 A1 | 9/2005 | Kassab |
| 2005/0234289 A1 | 10/2005 | Anstadt et al. |
| 2005/0246314 A1 | 11/2005 | Eder |
| 2005/0248136 A1 | 11/2005 | Breed et al. |
| 2005/0267911 A1 | 12/2005 | Kamath et al. |
| 2005/0272110 A1 | 12/2005 | Drukier |
| 2005/0286179 A1 | 12/2005 | Huff et al. |
| 2006/0015492 A1 | 1/2006 | Keating et al. |
| 2006/0015494 A1 | 1/2006 | Keating et al. |
| 2006/0015495 A1 | 1/2006 | Keating et al. |
| 2006/0015496 A1 | 1/2006 | Keating et al. |
| 2006/0015497 A1 | 1/2006 | Keating et al. |
| 2006/0020597 A1 | 1/2006 | Keating et al. |
| 2006/0059028 A1 | 3/2006 | Eder |
| 2006/0084115 A1 | 4/2006 | DeNardo et al. |
| 2006/0094967 A1 | 5/2006 | Bennett et al. |
| 2006/0101017 A1 | 5/2006 | Eder |
| 2006/0106797 A1 | 5/2006 | Srinivasa et al. |
| 2006/0111754 A1 | 5/2006 | Rezai et al. |
| 2006/0120584 A1 | 6/2006 | Hillman |
| 2006/0123363 A1 | 6/2006 | Williams et al. |
| 2006/0142634 A1 | 6/2006 | Anstadt et al. |
| 2006/0149139 A1 | 7/2006 | Bonmassar et al. |
| 2006/0155398 A1 | 7/2006 | Hoffberg et al. |
| 2006/0167334 A1 | 7/2006 | Anstadt et al. |
| 2006/0167784 A1 | 7/2006 | Hoffberg |
| 2006/0184473 A1 | 8/2006 | Eder |
| 2006/0200253 A1 | 9/2006 | Hoffberg et al. |
| 2006/0200258 A1 | 9/2006 | Hoffberg et al. |
| 2006/0200259 A1 | 9/2006 | Hoffberg et al. |
| 2006/0200260 A1 | 9/2006 | Hoffberg et al. |
| 2006/0206159 A1 | 9/2006 | Moffitt et al. |
| 2006/0208169 A1 | 9/2006 | Breed et al. |
| 2006/0211909 A1 | 9/2006 | Anstadt et al. |
| 2006/0229822 A1 | 10/2006 | Theobald et al. |
| 2006/0241510 A1 | 10/2006 | Halperin et al. |
| 2006/0244246 A1 | 11/2006 | Breed et al. |
| 2006/0247536 A1 | 11/2006 | Koski et al. |
| 2006/0247542 A1 | 11/2006 | Watanabe et al. |
| 2006/0251293 A1 | 11/2006 | Piirainen et al. |
| 2006/0253258 A1 | 11/2006 | Miyake |
| 2006/0253781 A1 | 11/2006 | Pea et al. |
| 2006/0293607 A1 | 12/2006 | Alt et al. |
| 2007/0013509 A1 | 1/2007 | Lakshmanan et al. |
| 2007/0016476 A1 | 1/2007 | Hoffberg et al. |
| 2007/0025597 A1 | 2/2007 | Breed et al. |

(56) References Cited

U.S. PATENT DOCUMENTS

| | | |
|---|---|---|
| 2007/0035114 A1 | 2/2007 | Breed et al. |
| 2007/0053513 A1 | 3/2007 | Hoffberg |
| 2007/0054266 A1 | 3/2007 | Sato et al. |
| 2007/0054347 A1 | 3/2007 | Rosendahl et al. |
| 2007/0067003 A1 | 3/2007 | Sanchez et al. |
| 2007/0083128 A1 | 4/2007 | Cote et al. |
| 2007/0083243 A1 | 4/2007 | Prakash et al. |
| 2007/0086624 A1 | 4/2007 | Breed et al. |
| 2007/0087756 A1 | 4/2007 | Hoffberg |
| 2007/0103328 A1 | 5/2007 | Lakshmanan et al. |
| 2007/0106170 A1 | 5/2007 | Dunseath et al. |
| 2007/0118054 A1 | 5/2007 | Pinhas et al. |
| 2007/0135984 A1 | 6/2007 | Breed et al. |
| 2007/0140551 A1 | 6/2007 | He et al. |
| 2007/0150006 A1 | 6/2007 | Libbus et al. |
| 2007/0150021 A1 | 6/2007 | Chen et al. |
| 2007/0152433 A1 | 7/2007 | Weichenberger et al. |
| 2007/0154063 A1 | 7/2007 | Breed |
| 2007/0154078 A1 | 7/2007 | He et al. |
| 2007/0154079 A1 | 7/2007 | He et al. |
| 2007/0154099 A1 | 7/2007 | He et al. |
| 2007/0156317 A1 | 7/2007 | Breed |
| 2007/0160973 A1 | 7/2007 | Burns |
| 2007/0162084 A1 | 7/2007 | Chen et al. |
| 2007/0162189 A1 | 7/2007 | Huff et al. |
| 2007/0162992 A1 | 7/2007 | Burns |
| 2007/0167846 A1 | 7/2007 | Sternickel et al. |
| 2007/0175998 A1 | 8/2007 | Lev |
| 2007/0191742 A1 | 8/2007 | Park |
| 2007/0193811 A1 | 8/2007 | Breed et al. |
| 2007/0213786 A1 | 9/2007 | Sackellares et al. |
| 2007/0219749 A1 | 9/2007 | Jayabalan et al. |
| 2007/0230795 A1 | 10/2007 | Abramoff et al. |
| 2007/0256432 A1 | 11/2007 | Zugibe et al. |
| 2007/0258329 A1 | 11/2007 | Winey |
| 2007/0260285 A1 | 11/2007 | Libbus et al. |
| 2007/0260425 A1 | 11/2007 | Kim |
| 2007/0260427 A1 | 11/2007 | Kim |
| 2007/0260656 A1 | 11/2007 | Wiig |
| 2007/0262574 A1 | 11/2007 | Breed et al. |
| 2007/0265533 A1 | 11/2007 | Tran |
| 2007/0265806 A1 | 11/2007 | Kim |
| 2007/0265808 A1 | 11/2007 | Kim |
| 2007/0273504 A1 | 11/2007 | Tran |
| 2007/0276270 A1 | 11/2007 | Tran |
| 2007/0276279 A1 | 11/2007 | Echauz et al. |
| 2007/0286336 A1 | 12/2007 | Bernard et al. |
| 2007/0299349 A1 | 12/2007 | Alt et al. |
| 2008/0001735 A1 | 1/2008 | Tran |
| 2008/0004672 A1 | 1/2008 | Dalal et al. |
| 2008/0004904 A1 | 1/2008 | Tran |
| 2008/0013747 A1 | 1/2008 | Tran |
| 2008/0015871 A1 | 1/2008 | Eder |
| 2008/0021336 A1 | 1/2008 | Dobak |
| 2008/0021342 A1 | 1/2008 | Echauz et al. |
| 2008/0027769 A1 | 1/2008 | Eder |
| 2008/0027841 A1 | 1/2008 | Eder |
| 2008/0033316 A1 | 2/2008 | Kassab et al. |
| 2008/0036187 A1 | 2/2008 | Breed |
| 2008/0036580 A1 | 2/2008 | Breed |
| 2008/0039904 A1 | 2/2008 | Bulkes et al. |
| 2008/0042067 A1 | 2/2008 | Rousso et al. |
| 2008/0051660 A1 | 2/2008 | Kakadaris et al. |
| 2008/0058668 A1 | 3/2008 | Seyed Momen et al. |
| 2008/0065291 A1 | 3/2008 | Breed |
| 2008/0071136 A1 | 3/2008 | Oohashi et al. |
| 2008/0091114 A1 | 4/2008 | Min et al. |
| 2008/0114564 A1 | 5/2008 | Ihara |
| 2008/0119749 A1 | 5/2008 | Haro et al. |
| 2008/0128626 A1 | 6/2008 | Rousso et al. |
| 2008/0142713 A1 | 6/2008 | Breed et al. |
| 2008/0144944 A1 | 6/2008 | Breed |
| 2008/0146334 A1 | 6/2008 | Kil |
| 2008/0147438 A1 | 6/2008 | Kil |
| 2008/0147440 A1 | 6/2008 | Kil |
| 2008/0147441 A1 | 6/2008 | Kil |
| 2008/0152217 A1 | 6/2008 | Greer |
| 2008/0157510 A1 | 7/2008 | Breed et al. |
| 2008/0161877 A1 | 7/2008 | Kirby et al. |
| 2008/0162487 A1 | 7/2008 | Richter |
| 2008/0175480 A1 | 7/2008 | Shi et al. |
| 2008/0194946 A1 | 8/2008 | Summers et al. |
| 2008/0194975 A1 | 8/2008 | MacQuarrie et al. |
| 2008/0194996 A1 | 8/2008 | Kassab |
| 2008/0195261 A1 | 8/2008 | Breed |
| 2008/0222734 A1 | 9/2008 | Redlich et al. |
| 2008/0230702 A1 | 9/2008 | Rousso et al. |
| 2008/0230705 A1 | 9/2008 | Rousso et al. |
| 2008/0235165 A1 | 9/2008 | Movellan et al. |
| 2008/0236275 A1 | 10/2008 | Breed et al. |
| 2008/0247598 A1 | 10/2008 | Movellan et al. |
| 2008/0256069 A1 | 10/2008 | Eder |
| 2008/0262367 A1 | 10/2008 | Mugler et al. |
| 2008/0263323 A1 | 10/2008 | Mould et al. |
| 2008/0265130 A1 | 10/2008 | Colomb et al. |
| 2008/0269625 A1 | 10/2008 | Halperin et al. |
| 2008/0270328 A1 | 10/2008 | Lafferty et al. |
| 2008/0275314 A1 | 11/2008 | Mack et al. |
| 2008/0275349 A1 | 11/2008 | Halperin et al. |
| 2008/0292146 A1 | 11/2008 | Breed et al. |
| 2008/0294019 A1 | 11/2008 | Tran |
| 2008/0306397 A1 | 12/2008 | Bonmassar et al. |
| 2008/0312523 A1 | 12/2008 | Dunseath |
| 2009/0012766 A1 | 1/2009 | Miyake et al. |
| 2009/0018891 A1 | 1/2009 | Eder |
| 2009/0024044 A1 | 1/2009 | Virtanen et al. |
| 2009/0024549 A1 | 1/2009 | Johnson |
| 2009/0036758 A1 | 2/2009 | Brauker et al. |
| 2009/0036940 A1 | 2/2009 | Wei et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0054742 A1 | 2/2009 | Kaminska et al. |
| 2009/0054758 A1 | 2/2009 | Dunseath |
| 2009/0055147 A1 | 2/2009 | Miyake et al. |
| 2009/0062635 A1 | 3/2009 | Brauker et al. |
| 2009/0062684 A1 | 3/2009 | Gregersen et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076401 A1 | 3/2009 | Mazar et al. |
| 2009/0078875 A1 | 3/2009 | Rousso et al. |
| 2009/0083010 A1 | 3/2009 | Qi et al. |
| 2009/0099473 A1 | 4/2009 | Dunseath et al. |
| 2009/0105556 A1 | 4/2009 | Fricke et al. |
| 2009/0118637 A1 | 5/2009 | Kassab et al. |
| 2009/0169075 A1 | 7/2009 | Ishida et al. |
| 2009/0171740 A1 | 7/2009 | Eder |
| 2009/0177420 A1 | 7/2009 | Fournier et al. |
| 2009/0182287 A1 | 7/2009 | Kassab |
| 2009/0203972 A1 | 8/2009 | Heneghan et al. |
| 2009/0203981 A1 | 8/2009 | Brauker et al. |
| 2009/0204029 A1 | 8/2009 | Kassab |
| 2009/0204341 A1 | 8/2009 | Brauker et al. |
| 2009/0216133 A1 | 8/2009 | Kassab |
| 2009/0222108 A1 | 9/2009 | Lou et al. |
| 2009/0227876 A1 | 9/2009 | Tran |
| 2009/0227877 A1 | 9/2009 | Tran |
| 2009/0228408 A1 | 9/2009 | Kaushal et al. |
| 2009/0231173 A1 | 9/2009 | Kilbank |
| 2009/0240366 A1 | 9/2009 | Kaushal et al. |
| 2009/0259533 A1 | 10/2009 | Utter et al. |
| 2009/0259534 A1 | 10/2009 | Utter et al. |
| 2009/0259537 A1 | 10/2009 | Veksler et al. |
| 2009/0270746 A1 | 10/2009 | Min |
| 2009/0271342 A1 | 10/2009 | Eder |
| 2009/0285166 A1 | 11/2009 | Huber et al. |
| 2009/0286509 A1 | 11/2009 | Huber et al. |
| 2009/0286512 A1 | 11/2009 | Huber et al. |

(56) References Cited

U.S. PATENT DOCUMENTS

| | | |
|---|---|---|
| 2009/0288140 A1 | 11/2009 | Huber et al. |
| 2009/0288152 A1 | 11/2009 | Huber et al. |
| 2009/0299162 A1 | 12/2009 | Brauker et al. |
| 2009/0307164 A1 | 12/2009 | Baughman |
| 2009/0312612 A1 | 12/2009 | Rantala |
| 2009/0312819 A1 | 12/2009 | Klefenz et al. |
| 2009/0313041 A1 | 12/2009 | Eder |
| 2009/0316988 A1 | 12/2009 | Xu et al. |
| 2009/0318779 A1 | 12/2009 | Tran |
| 2009/0318987 A1 | 12/2009 | Kroll et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0010355 A1 | 1/2010 | Kassab |
| 2010/0010368 A1 | 1/2010 | Kassab |
| 2010/0010488 A1 | 1/2010 | Kassab et al. |
| 2010/0010503 A1 | 1/2010 | Kassab |
| 2010/0010556 A1 | 1/2010 | Zhao et al. |
| 2010/0010681 A1 | 1/2010 | Zugibe et al. |
| 2010/0014718 A1 | 1/2010 | Savvides et al. |
| 2010/0016687 A1 | 1/2010 | Brauker et al. |
| 2010/0018718 A1 | 1/2010 | Krebs et al. |
| 2010/0020208 A1 | 1/2010 | Barbu |
| 2010/0020961 A1 | 1/2010 | Spottiswoode |
| 2010/0022855 A1 | 1/2010 | Brauker et al. |
| 2010/0023307 A1 | 1/2010 | Lee et al. |
| 2010/0026799 A1 | 2/2010 | Fujisawa et al. |
| 2010/0027431 A1 | 2/2010 | Morrison et al. |
| 2010/0027469 A1 | 2/2010 | Gurajala et al. |
| 2010/0027845 A1 | 2/2010 | Kim et al. |
| 2010/0027846 A1 | 2/2010 | Xu et al. |
| 2010/0027892 A1 | 2/2010 | Guan et al. |
| 2010/0030038 A1 | 2/2010 | Brauker et al. |
| 2010/0030090 A1 | 2/2010 | Zhang et al. |
| 2010/0030484 A1 | 2/2010 | Brauker et al. |
| 2010/0030485 A1 | 2/2010 | Brauker et al. |
| 2010/0041365 A1 | 2/2010 | Lott et al. |
| 2010/0045465 A1 | 2/2010 | Brauker et al. |
| 2010/0046842 A1 | 2/2010 | Conwell |
| 2010/0048242 A1 | 2/2010 | Rhoads et al. |
| 2010/0049369 A1 | 2/2010 | Lou et al. |
| 2010/0066540 A1 | 3/2010 | Theobald et al. |
| 2010/0069768 A1 | 3/2010 | Min et al. |
| 2010/0076642 A1 | 3/2010 | Hoffberg et al. |
| 2010/0094102 A1 | 4/2010 | Zhang et al. |
| 2010/0094147 A1 | 4/2010 | Inan et al. |
| 2010/0100148 A1 | 4/2010 | Min et al. |
| 2010/0100150 A1 | 4/2010 | Kirby et al. |
| 2010/0102825 A1 | 4/2010 | Bushnell et al. |
| 2010/0106269 A1 | 4/2010 | Garudadri et al. |
| 2010/0106458 A1 | 4/2010 | Leu et al. |
| 2010/0111396 A1 | 5/2010 | Boucheron |
| 2010/0113944 A1 | 5/2010 | Min et al. |
| 2010/0114207 A1 | 5/2010 | Snell et al. |
| 2010/0119128 A1 | 5/2010 | Zhang et al. |
| 2010/0121406 A1 | 5/2010 | Libbus et al. |
| 2010/0123587 A1 | 5/2010 | Walls |
| 2010/0130189 A1 | 5/2010 | Morrison et al. |
| 2010/0138026 A1 | 6/2010 | Kaushal et al. |
| 2010/0152795 A1 | 6/2010 | Schecter |
| 2010/0152905 A1 | 6/2010 | Kusiak |
| 2010/0159945 A1 | 6/2010 | Brisebois |
| 2010/0161654 A1 | 6/2010 | Levy |
| 2010/0168836 A1 | 7/2010 | Kassab |
| 2010/0169122 A1 | 7/2010 | Ruoff et al. |
| 2010/0169810 A1 | 7/2010 | Ruoff et al. |
| 2010/0174271 A1 | 7/2010 | Kassab |
| 2010/0179400 A1 | 7/2010 | Brauker et al. |
| 2010/0179438 A1 | 7/2010 | Heneghan et al. |
| 2010/0184702 A1 | 7/2010 | DeNardo et al. |
| 2010/0198098 A1 | 8/2010 | Osorio et al. |
| 2010/0204540 A1 | 8/2010 | Oohashi et al. |
| 2010/0204550 A1 | 8/2010 | Heneghan et al. |
| 2010/0210921 A1 | 8/2010 | Park et al. |
| 2010/0214545 A1 | 8/2010 | Funk et al. |
| 2010/0217145 A1 | 8/2010 | Buscema |
| 2010/0235285 A1 | 9/2010 | Hoffberg |
| 2010/0246544 A1 | 9/2010 | Brisebois et al. |
| 2010/0249628 A1 | 9/2010 | Kortelainen |
| 2010/0256701 A1 | 10/2010 | Muller |
| 2010/0272340 A1 | 10/2010 | Bar-Aviv et al. |
| 2010/0274219 A1 | 10/2010 | Wenzel et al. |
| 2010/0292968 A1 | 11/2010 | Gielis |
| 2010/0293115 A1 | 11/2010 | Seyed Momen |
| 2010/0304864 A1 | 12/2010 | Johnson et al. |
| 2010/0305634 A1 | 12/2010 | Moffitt et al. |
| 2010/0316283 A1 | 12/2010 | Greer |
| 2010/0317420 A1 | 12/2010 | Hoffberg |
| 2010/0331908 A1 | 12/2010 | Farazi |
| 2011/0004415 A1 | 1/2011 | Miyake et al. |
| 2011/0004513 A1 | 1/2011 | Hoffberg |
| 2011/0015468 A1 | 1/2011 | Aarts et al. |
| 2011/0015702 A1 | 1/2011 | Ternes et al. |
| 2011/0015703 A1 | 1/2011 | Ternes et al. |
| 2011/0015704 A1 | 1/2011 | Ternes et al. |
| 2011/0021928 A1 | 1/2011 | Giovangrandi et al. |
| 2011/0026832 A1 | 2/2011 | LeMoigne-Stewart et al. |
| 2011/0034811 A1 | 2/2011 | Naujokat et al. |
| 2011/0034824 A1 | 2/2011 | Kassab |
| 2011/0034967 A1 | 2/2011 | Chen et al. |
| 2011/0036801 A1 | 2/2011 | Krans et al. |
| 2011/0046498 A1 | 2/2011 | Klap et al. |
| 2011/0046508 A1 | 2/2011 | Wenzel et al. |
| 2011/0047105 A1 | 2/2011 | Sternickel et al. |
| 2011/0060230 A1 | 3/2011 | Gill et al. |
| 2011/0060235 A1 | 3/2011 | Crompvoets et al. |
| 2011/0066041 A1* | 3/2011 | Pandia .................. A61B 5/029 600/484 |
| 2011/0066042 A1 | 3/2011 | Pandia et al. |
| 2011/0066205 A1 | 3/2011 | Crompvoets et al. |
| 2011/0066404 A1 | 3/2011 | Salazar-Tio et al. |
| 2011/0082511 A1 | 4/2011 | Aarts et al. |
| 2011/0087113 A1 | 4/2011 | Mack et al. |
| 2011/0087115 A1 | 4/2011 | Sackner et al. |
| 2011/0096144 A1 | 4/2011 | Pea et al. |
| 2011/0098583 A1 | 4/2011 | Pandia et al. |
| 2011/0098770 A1 | 4/2011 | Ryu et al. |
| 2011/0105930 A1 | 5/2011 | Thiagarajan et al. |
| 2011/0106558 A1 | 5/2011 | Solito et al. |
| 2011/0112426 A1 | 5/2011 | Causevic |
| 2011/0112442 A1 | 5/2011 | Meger et al. |
| 2011/0115624 A1 | 5/2011 | Tran |
| 2011/0118614 A1 | 5/2011 | Brauers et al. |
| 2011/0130670 A1 | 6/2011 | MacQuarrie et al. |
| 2011/0130671 A1 | 6/2011 | MacQuarrie et al. |
| 2011/0131041 A1 | 6/2011 | Cortez et al. |
| 2011/0131162 A1 | 6/2011 | Kaushal et al. |
| 2011/0135166 A1 | 6/2011 | Wechsler et al. |
| 2011/0137110 A1 | 6/2011 | Aarts et al. |
| 2011/0144065 A1 | 6/2011 | Denardo et al. |
| 2011/0144519 A1 | 6/2011 | Causevic |
| 2011/0150253 A1 | 6/2011 | Corona-Strauss et al. |
| 2011/0152974 A1 | 6/2011 | Rezai et al. |
| 2011/0156896 A1 | 6/2011 | Hoffberg et al. |
| 2011/0160656 A1 | 6/2011 | Johnson et al. |
| 2011/0164783 A1 | 7/2011 | Hays et al. |
| 2011/0167110 A1 | 7/2011 | Hoffberg et al. |
| 2011/0172500 A1 | 7/2011 | Van Dooren et al. |
| 2011/0172930 A1 | 7/2011 | Pancoska et al. |
| 2011/0181422 A1 | 7/2011 | Tran |
| 2011/0196254 A1 | 8/2011 | Wenzel et al. |
| 2011/0196441 A1 | 8/2011 | Ryu et al. |
| 2011/0196442 A1 | 8/2011 | Ryu et al. |
| 2011/0208016 A1 | 8/2011 | Bombardini |
| 2011/0236922 A1 | 9/2011 | Burns |
| 2011/0251502 A1 | 10/2011 | Friedrich et al. |
| 2011/0261178 A1 | 10/2011 | Lo et al. |
| 2011/0263958 A1 | 10/2011 | Brauker et al. |
| 2011/0263994 A1 | 10/2011 | Burns et al. |
| 2011/0268328 A1 | 11/2011 | Bar-Aviv et al. |
| 2011/0275364 A1 | 11/2011 | Austin et al. |
| 2011/0280447 A1 | 11/2011 | Conwell |
| 2011/0285982 A1 | 11/2011 | Breed |
| 2011/0301660 A1 | 12/2011 | Libbus et al. |

(56) References Cited

U.S. PATENT DOCUMENTS

| | | |
|---|---|---|
| 2011/0313285 A1 | 12/2011 | Fallavollita et al. |
| 2011/0319776 A1 | 12/2011 | Sweeney et al. |
| 2011/0319778 A1 | 12/2011 | Sweeney et al. |
| 2011/0319782 A1 | 12/2011 | Sweeney et al. |
| 2012/0004564 A1 | 1/2012 | Dobak |
| 2012/0004854 A1 | 1/2012 | Fernandez et al. |
| 2012/0010677 A1 | 1/2012 | Wenzel et al. |
| 2012/0010867 A1 | 1/2012 | Eder |
| 2012/0022336 A1 | 1/2012 | Teixeira |
| 2012/0022350 A1 | 1/2012 | Teixeira |
| 2012/0022384 A1 | 1/2012 | Teixeira |
| 2012/0022844 A1 | 1/2012 | Teixeira |
| 2012/0036016 A1 | 2/2012 | Hoffberg et al. |
| 2012/0041330 A1 | 2/2012 | Prichep et al. |
| 2012/0041608 A1 | 2/2012 | Zugibe et al. |
| 2012/0050750 A1 | 3/2012 | Hays et al. |
| 2012/0053441 A1 | 3/2012 | Kassab |
| 2012/0066217 A1 | 3/2012 | Eder |
| 2012/0066259 A1 | 3/2012 | Huber et al. |
| 2012/0071792 A1 | 3/2012 | Pfeffer et al. |
| 2012/0073825 A1 | 3/2012 | Routh et al. |
| 2012/0083246 A1 | 4/2012 | Huber et al. |
| 2012/0089046 A1 | 4/2012 | Kassab et al. |
| 2012/0092156 A1 | 4/2012 | Tran |
| 2012/0092157 A1 | 4/2012 | Tran |
| 2012/0095352 A1 | 4/2012 | Tran |
| 2012/0095357 A1 | 4/2012 | Tran |
| 2012/0109612 A1 | 5/2012 | Krebs et al. |
| 2012/0109653 A1 | 5/2012 | Yen et al. |
| 2012/0114249 A1 | 5/2012 | Conwell |
| 2012/0123232 A1 | 5/2012 | Najarian et al. |
| 2012/0123279 A1 | 5/2012 | Brueser et al. |
| 2012/0132211 A1 | 5/2012 | Halperin et al. |
| 2012/0136263 A1 | 5/2012 | Prakash et al. |
| 2012/0143072 A1 | 6/2012 | Prakash et al. |
| 2012/0143078 A1 | 6/2012 | Kassab et al. |
| 2012/0143382 A1 | 6/2012 | Lou |
| 2012/0148149 A1 | 6/2012 | Kumar et al. |
| 2012/0148157 A1 | 6/2012 | Kumar et al. |
| 2012/0157798 A1 | 6/2012 | Averina et al. |
| 2012/0157856 A1 | 6/2012 | An et al. |
| 2012/0157861 A1 | 6/2012 | Jarverud et al. |
| 2012/0158633 A1 | 6/2012 | Eder |
| 2012/0165892 A1 | 6/2012 | Min et al. |
| 2012/0169053 A1 | 7/2012 | Tchoryk, Jr. et al. |
| 2012/0172741 A1 | 7/2012 | Arcot-Krishnamurthy et al. |
| 2012/0172742 A1 | 7/2012 | Arcot-Krishnamurthy et al. |
| 2012/0172743 A1 | 7/2012 | Aguilar et al. |
| 2012/0172746 A1 | 7/2012 | Kassab |
| 2012/0173154 A1 | 7/2012 | Rosendahl et al. |
| 2012/0179216 A1 | 7/2012 | Moffitt et al. |
| 2012/0185012 A1 | 7/2012 | Ryu et al. |
| 2012/0190404 A1 | 7/2012 | Rhoads |
| 2012/0197333 A1 | 8/2012 | Zhao et al. |
| 2012/0197831 A1 | 8/2012 | Dong et al. |
| 2012/0203077 A1 | 8/2012 | He et al. |
| 2012/0203090 A1 | 8/2012 | Min |
| 2012/0209798 A1 | 8/2012 | Kaushal et al. |
| 2012/0214510 A1 | 8/2012 | Brisebois |
| 2012/0220835 A1 | 8/2012 | Chung |
| 2012/0226126 A1 | 9/2012 | Busse et al. |
| 2012/0238800 A1 | 9/2012 | Naujokat et al. |
| 2012/0242501 A1 | 9/2012 | Tran et al. |
| 2012/0245464 A1 | 9/2012 | Tran |
| 2012/0245476 A1 | 9/2012 | Skerl et al. |
| 2012/0245481 A1 | 9/2012 | Blanco et al. |
| 2012/0253419 A1 | 10/2012 | Rosenberg et al. |
| 2012/0257046 A1 | 10/2012 | Mueller et al. |
| 2012/0265350 A1 | 10/2012 | Ashdown |
| 2012/0271177 A1 | 10/2012 | Emerson et al. |
| 2012/0271371 A1 | 10/2012 | Keel et al. |
| 2012/0271382 A1 | 10/2012 | Arcot-Krishnamurthy et al. |
| 2012/0274937 A1 | 11/2012 | Hays et al. |
| 2012/0277545 A1 | 11/2012 | Teixeira |
| 2012/0290505 A1 | 11/2012 | Eder |
| 2012/0296228 A1 | 11/2012 | Zhang et al. |
| 2012/0303504 A1 | 11/2012 | Eder |
| 2012/0303560 A1 | 11/2012 | Sedaghat et al. |
| 2012/0330109 A1 | 12/2012 | Tran |
| 2012/0330170 A1 | 12/2012 | Chiu et al. |
| 2012/0330373 A1 | 12/2012 | Ternes et al. |
| 2013/0006317 A1 | 1/2013 | Keel et al. |
| 2013/0009783 A1 | 1/2013 | Tran |
| 2013/0011062 A1 | 1/2013 | Conwell et al. |
| 2013/0023956 A1 | 1/2013 | Ternes et al. |
| 2013/0023957 A1 | 1/2013 | Ternes et al. |
| 2013/0028052 A1 | 1/2013 | Routh et al. |
| 2013/0030312 A1 | 1/2013 | Keel et al. |
| 2013/0030314 A1 | 1/2013 | Keel et al. |
| 2013/0030315 A1 | 1/2013 | Keel et al. |
| 2013/0030484 A1 | 1/2013 | Zhang et al. |
| 2013/0030486 A1 | 1/2013 | Betzold |
| 2013/0030487 A1 | 1/2013 | Keel et al. |
| 2013/0053907 A1 | 2/2013 | Kirchner et al. |
| 2013/0053912 A1 | 2/2013 | Bornzin et al. |
| 2013/0053913 A1 | 2/2013 | Koh et al. |
| 2013/0053926 A1 | 2/2013 | Hincapie Ordonez et al. |
| 2013/0060296 A1 | 3/2013 | Wenzel et al. |
| 2013/0060297 A1 | 3/2013 | Stein |
| 2013/0063613 A1 | 3/2013 | Conwell |
| 2013/0069780 A1 | 3/2013 | Tran et al. |
| 2013/0071837 A1 | 3/2013 | Winters-Hilt et al. |
| 2013/0072807 A1 | 3/2013 | Tran |
| 2013/0073490 A1 | 3/2013 | Baughman et al. |
| 2013/0073981 A1 | 3/2013 | Pea et al. |
| 2013/0077843 A1 | 3/2013 | Bruder et al. |
| 2013/0077891 A1 | 3/2013 | Nimnual et al. |
| 2013/0079002 A1 | 3/2013 | Huber et al. |
| 2013/0085401 A1 | 4/2013 | Zhang et al. |
| 2013/0090247 A1 | 4/2013 | Gardner |
| 2013/0090265 A1 | 4/2013 | Gardner |
| 2013/0090266 A1 | 4/2013 | Gardner |
| 2013/0095459 A1 | 4/2013 | Tran |
| 2013/0096394 A1 | 4/2013 | Gupta et al. |
| 2013/0109989 A1 | 5/2013 | Busse et al. |
| 2013/0109995 A1 | 5/2013 | Rothman et al. |
| 2013/0123666 A1 | 5/2013 | Giuffrida et al. |
| 2013/0123684 A1 | 5/2013 | Giuffrida et al. |
| 2013/0123873 A1 | 5/2013 | Libbus et al. |
| 2013/0135008 A1 | 5/2013 | Zhang et al. |
| 2013/0137998 A1 | 5/2013 | Lange et al. |
| 2013/0144178 A1 | 6/2013 | Halperin et al. |
| 2013/0151447 A1 | 6/2013 | Kaushal et al. |
| 2013/0158415 A1 | 6/2013 | Kim et al. |
| 2013/0165819 A1 | 6/2013 | Tieu |
| 2013/0171599 A1 | 7/2013 | Bleich et al. |
| 2013/0172691 A1 | 7/2013 | Tran |
| 2013/0173194 A1 | 7/2013 | Dholakia et al. |
| 2013/0178718 A1 | 7/2013 | Tran et al. |
| 2013/0178730 A1 | 7/2013 | Sternickel et al. |
| 2013/0184538 A1 | 7/2013 | Lee et al. |
| 2013/0184553 A1 | 7/2013 | Kassab et al. |
| 2013/0184603 A1 | 7/2013 | Rothman |
| 2013/0189977 A1 | 7/2013 | Brisebois et al. |
| 2013/0190645 A1 | 7/2013 | Wenzel et al. |
| 2013/0190835 A1 | 7/2013 | Zhao et al. |
| 2013/0191090 A1 | 7/2013 | Krebs et al. |
| 2013/0197322 A1 | 8/2013 | Tran |
| 2013/0197375 A1 | 8/2013 | Heise et al. |
| 2013/0197380 A1 | 8/2013 | Oral et al. |
| 2013/0197597 A1 | 8/2013 | Anderson et al. |
| 2013/0202177 A1 | 8/2013 | Bar-Aviv et al. |
| 2013/0204122 A1 | 8/2013 | Hendler et al. |
| 2013/0211271 A1 | 8/2013 | Kang et al. |
| 2013/0211291 A1 | 8/2013 | Tran |
| 2013/0211482 A1 | 8/2013 | Piipponen |
| 2013/0214943 A1 | 8/2013 | Yen et al. |
| 2013/0218156 A1 | 8/2013 | Kassab et al. |
| 2013/0231574 A1 | 9/2013 | Tran |
| 2013/0236067 A1 | 9/2013 | Savvides et al. |
| 2013/0245502 A1 | 9/2013 | Lange et al. |
| 2013/0245722 A1 | 9/2013 | Ternes et al. |
| 2013/0252604 A1 | 9/2013 | Huber et al. |
| 2013/0261473 A1 | 10/2013 | Xi et al. |

(56) References Cited

U.S. PATENT DOCUMENTS

| | | |
|---|---|---|
| 2013/0269376 A1 | 10/2013 | Zugibe et al. |
| 2013/0273968 A1 | 10/2013 | Rhoads et al. |
| 2013/0296962 A1 | 11/2013 | Keel et al. |
| 2013/0301889 A1 | 11/2013 | Abramoff et al. |
| 2013/0303119 A1 | 11/2013 | Huber et al. |
| 2013/0303941 A1 | 11/2013 | Porges et al. |
| 2013/0310700 A1 | 11/2013 | Wiard et al. |
| 2013/0314694 A1 | 11/2013 | Tchoryk, Jr. et al. |
| 2013/0317392 A1 | 11/2013 | Kassab |
| 2013/0331661 A1 | 12/2013 | Woodward |
| 2013/0331904 A1 | 12/2013 | Ternes et al. |
| 2013/0336594 A1 | 12/2013 | Dorairaj |
| 2013/0338460 A1 | 12/2013 | He et al. |
| 2013/0338468 A1 | 12/2013 | Kassab |
| 2013/0338496 A1 | 12/2013 | Hielscher et al. |
| 2013/0338530 A1 | 12/2013 | Kassab |
| 2013/0345591 A1 | 12/2013 | Hincapie Ordonez et al. |
| 2014/0005496 A1 | 1/2014 | Sison et al. |
| 2014/0005743 A1 | 1/2014 | Giuffrida et al. |
| 2014/0012099 A1 | 1/2014 | Halperin et al. |
| 2014/0012144 A1 | 1/2014 | Crone |
| 2014/0025304 A1 | 1/2014 | McLennan et al. |
| 2014/0039330 A1 | 2/2014 | Seo et al. |
| 2014/0039333 A1 | 2/2014 | Min |
| 2014/0046209 A1 | 2/2014 | Klap et al. |
| 2014/0052209 A1 | 2/2014 | Ternes et al. |
| 2014/0052379 A1 | 2/2014 | McVay et al. |
| 2014/0055284 A1 | 2/2014 | Tran et al. |
| 2014/0066738 A1 | 3/2014 | Kassab |
| 2014/0066798 A1 | 3/2014 | Albert |
| 2014/0067463 A1 | 3/2014 | Richter |
| 2014/0067470 A1 | 3/2014 | Richter |
| 2014/0067484 A1 | 3/2014 | Richter |
| 2014/0067485 A1 | 3/2014 | Richter |
| 2014/0074179 A1 | 3/2014 | Heldman et al. |
| 2014/0074180 A1 | 3/2014 | Heldman et al. |
| 2014/0074564 A1 | 3/2014 | Richter |
| 2014/0077946 A1 | 3/2014 | Tran |
| 2014/0079297 A1 | 3/2014 | Tadayon et al. |
| 2014/0088415 A1 | 3/2014 | Hielscher et al. |
| 2014/0088676 A1 | 3/2014 | Moffitt et al. |
| 2014/0089241 A1 | 3/2014 | Hoffberg et al. |
| 2014/0094875 A1 | 4/2014 | Ternes et al. |
| 2014/0104059 A1 | 4/2014 | Tran |
| 2014/0114165 A1 | 4/2014 | Walker et al. |
| 2014/0114370 A1 | 4/2014 | Libbus et al. |
| 2014/0121476 A1 | 5/2014 | Tran et al. |
| 2014/0127672 A1 | 5/2014 | Davis et al. |
| 2014/0128953 A1 | 5/2014 | Zhao et al. |
| 2014/0135634 A1 | 5/2014 | Pranevicius et al. |
| 2014/0135645 A9 | 5/2014 | Wenzel et al. |
| 2014/0142437 A1 | 5/2014 | Inan et al. |
| 2014/0142444 A1 | 5/2014 | Ngo et al. |
| 2014/0142451 A1 | 5/2014 | Kim et al. |
| 2014/0143064 A1 | 5/2014 | Tran |
| 2014/0143251 A1 | 5/2014 | Wang et al. |
| 2014/0151563 A1 | 6/2014 | Rousso et al. |
| 2014/0163343 A1 | 6/2014 | Heneghan et al. |
| 2014/0163368 A1 | 6/2014 | Rousso et al. |
| 2014/0163425 A1 | 6/2014 | Tran |
| 2014/0169686 A1 | 6/2014 | Conwell et al. |
| 2014/0173452 A1 | 6/2014 | Hoffberg et al. |
| 2014/0180049 A1 | 6/2014 | Brauker et al. |
| 2014/0193087 A1 | 7/2014 | Conwell |
| 2014/0194702 A1 | 7/2014 | Tran |
| 2014/0200428 A1 | 7/2014 | Kassab |
| 2014/0200429 A1 | 7/2014 | Spector et al. |
| 2014/0200430 A1 | 7/2014 | Spector |
| 2014/0200471 A1 | 7/2014 | Spector |
| 2014/0200571 A1 | 7/2014 | Spector |
| 2014/0200572 A1 | 7/2014 | Spector |
| 2014/0200575 A1 | 7/2014 | Spector |
| 2014/0201126 A1 | 7/2014 | Zadeh et al. |
| 2014/0204700 A1 | 7/2014 | Valero et al. |
| 2014/0207204 A1 | 7/2014 | Halperin et al. |
| 2014/0213909 A1 | 7/2014 | Mestha et al. |
| 2014/0219566 A1 | 8/2014 | Rodriguez et al. |
| 2014/0221786 A1 | 8/2014 | Zhang et al. |
| 2014/0221859 A1 | 8/2014 | Albert |
| 2014/0222115 A1 | 8/2014 | Ternes et al. |
| 2014/0229409 A1 | 8/2014 | Kaushal et al. |
| 2014/0235201 A1 | 8/2014 | Gurajala et al. |
| 2014/0235965 A1 | 8/2014 | Tran |
| 2014/0236530 A1 | 8/2014 | Greene et al. |
| 2014/0249429 A1 | 9/2014 | Tran |
| 2014/0266787 A1 | 9/2014 | Tran |
| 2014/0267299 A1 | 9/2014 | Couse |
| 2014/0275824 A1 | 9/2014 | Couse |
| 2014/0275829 A1 | 9/2014 | Berezhnyy et al. |
| 2014/0275886 A1 | 9/2014 | Teixeira |
| 2014/0275925 A1 | 9/2014 | Thakur et al. |
| 2014/0276121 A1 | 9/2014 | Kassab |
| 2014/0276191 A1 | 9/2014 | Kassab |
| 2014/0277239 A1 | 9/2014 | Maskara et al. |
| 2014/0277241 A1 | 9/2014 | Bleich et al. |
| 2014/0288442 A1 | 9/2014 | Bombardini |
| 2014/0288551 A1 | 9/2014 | Bharmi et al. |
| 2014/0289172 A1 | 9/2014 | Rothman et al. |
| 2014/0308930 A1 | 10/2014 | Tran |
| 2014/0309543 A1 | 10/2014 | Keel et al. |
| 2014/0309959 A1 | 10/2014 | Shen et al. |
| 2014/0315576 A1 | 10/2014 | Brisebois |
| 2014/0316221 A1 | 10/2014 | Rothman |
| 2014/0321756 A9 | 10/2014 | Guan et al. |
| 2014/0323821 A1 | 10/2014 | Manicka et al. |
| 2014/0325019 A1 | 10/2014 | Austin et al. |
| 2014/0342703 A1 | 11/2014 | Huber et al. |
| 2014/0343396 A1 | 11/2014 | Sternickel et al. |
| 2014/0344013 A1 | 11/2014 | Karty et al. |
| 2014/0350361 A1 | 11/2014 | De Chazal et al. |
| 2014/0351188 A1 | 11/2014 | Bagg |
| 2014/0362013 A1 | 12/2014 | Nikoozadeh et al. |
| 2014/0364721 A1 | 12/2014 | Lee et al. |
| 2014/0371574 A1 | 12/2014 | Shusterman et al. |
| 2014/0371834 A1 | 12/2014 | Chen et al. |
| 2014/0378849 A1 | 12/2014 | Krimsky et al. |
| 2015/0005594 A1 | 1/2015 | Chamoun et al. |
| 2015/0005646 A1 | 1/2015 | Balakrishnan et al. |
| 2015/0005655 A1 | 1/2015 | Sato |
| 2015/0012256 A1 | 1/2015 | Routh et al. |
| 2015/0016702 A1 | 1/2015 | Huizenga et al. |
| 2015/0018632 A1 | 1/2015 | Khair |
| 2015/0018637 A1 | 1/2015 | Chen et al. |
| 2015/0025328 A1 | 1/2015 | Khair |
| 2015/0025334 A1 | 1/2015 | Jain |
| 2015/0025335 A1 | 1/2015 | Jain et al. |
| 2015/0025336 A1 | 1/2015 | Mestek et al. |
| 2015/0025393 A1 | 1/2015 | Hong et al. |
| 2015/0025394 A1 | 1/2015 | Hong et al. |
| 2015/0031964 A1 | 1/2015 | Bly et al. |
| 2015/0031969 A1 | 1/2015 | Khair |
| 2015/0032015 A1 | 1/2015 | Chiu |
| 2015/0032178 A1 | 1/2015 | Simon et al. |
| 2015/0038856 A1 | 2/2015 | Houlton et al. |
| 2015/0045684 A1 | 2/2015 | Schie et al. |
| 2015/0046095 A1 | 2/2015 | Takahashi et al. |
| 2015/0046181 A1 | 2/2015 | Adjaoute |
| 2015/0046216 A1 | 2/2015 | Adjaoute |
| 2015/0051083 A1 | 2/2015 | Regensburger et al. |
| 2015/0051452 A1 | 2/2015 | Ciaccio |
| 2015/0057512 A1 | 2/2015 | Kapoor |
| 2015/0058061 A1 | 2/2015 | Salama et al. |
| 2015/0065814 A1 | 3/2015 | Kapoor |
| 2015/0065815 A1 | 3/2015 | Najarian et al. |
| 2015/0065835 A1 | 3/2015 | Kassab |
| 2015/0068069 A1 | 3/2015 | Tran et al. |
| 2015/0073234 A1 | 3/2015 | Inan et al. |
| 2015/0073495 A1 | 3/2015 | Grill, Jr. et al. |
| 2015/0080746 A1 | 3/2015 | Bleich et al. |
| 2015/0081077 A1 | 3/2015 | Li et al. |
| 2015/0081324 A1 | 3/2015 | Adjaoute |
| 2015/0081911 A1 | 3/2015 | Li et al. |
| 2015/0086087 A1 | 3/2015 | Ricanek, Jr. et al. |
| 2015/0086131 A1 | 3/2015 | Wang et al. |

(56) References Cited

U.S. PATENT DOCUMENTS

| | | |
|---|---|---|
| 2015/0087589 A1 | 3/2015 | Schiemann et al. |
| 2015/0087931 A1 | 3/2015 | Banerjee et al. |
| 2015/0087947 A1 | 3/2015 | Freeman et al. |
| 2015/0088004 A1 | 3/2015 | Berckmans et al. |
| 2015/0088016 A1 | 3/2015 | Fleischacker et al. |
| 2015/0088024 A1 | 3/2015 | Sackellares et al. |
| 2015/0088214 A1 | 3/2015 | Allavatam et al. |
| 2015/0093037 A1 | 4/2015 | Dorairaj |
| 2015/0094012 A1 | 4/2015 | Gurajala et al. |
| 2015/0095146 A1 | 4/2015 | Adjaoute |
| 2015/0099941 A1 | 4/2015 | Tran |
| 2015/0099946 A1 | 4/2015 | Sahin |
| 2015/0103360 A1 | 4/2015 | Addison et al. |
| 2015/0103681 A1 | 4/2015 | Thiel et al. |
| 2015/0105086 A1 | 4/2015 | Thiel et al. |
| 2015/0105631 A1 | 4/2015 | Tran et al. |
| 2015/0105681 A1 | 4/2015 | Bonan et al. |
| 2015/0105695 A1 | 4/2015 | Sabatino |
| 2015/0106020 A1 | 4/2015 | Chung et al. |
| 2015/0106069 A1 | 4/2015 | Gielis |
| 2015/0106310 A1 | 4/2015 | Birdwell et al. |
| 2015/0106311 A1 | 4/2015 | Birdwell et al. |
| 2015/0106314 A1 | 4/2015 | Birdwell et al. |
| 2015/0106315 A1 | 4/2015 | Birdwell et al. |
| 2015/0106316 A1 | 4/2015 | Birdwell et al. |
| 2015/0109124 A1 | 4/2015 | He et al. |
| 2015/0112154 A1 | 4/2015 | He et al. |
| 2015/0112155 A1 | 4/2015 | Bijjani et al. |
| 2015/0112156 A1 | 4/2015 | He et al. |
| 2015/0112157 A1 | 4/2015 | Bijjani et al. |
| 2015/0112158 A1 | 4/2015 | He et al. |
| 2015/0112159 A1 | 4/2015 | He et al. |
| 2015/0112208 A1 | 4/2015 | He et al. |
| 2015/0112209 A1 | 4/2015 | Blaber et al. |
| 2015/0112211 A1 | 4/2015 | Purdy |
| 2015/0112212 A1 | 4/2015 | Purdy |
| 2015/0112220 A1 | 4/2015 | Sana et al. |
| 2015/0112403 A1 | 4/2015 | Ruffini et al. |
| 2015/0112409 A1 | 4/2015 | Hagedorn |
| 2015/0112452 A1 | 4/2015 | He et al. |
| 2015/0112606 A1 | 4/2015 | He et al. |
| 2015/0112636 A1 | 4/2015 | Grichnik et al. |
| 2015/0117741 A1 | 4/2015 | Imamura |
| 2015/0118158 A1 | 4/2015 | Jensen et al. |
| 2015/0119711 A1 | 4/2015 | Osumi et al. |
| 2015/0122018 A1 | 5/2015 | Yuen |
| 2015/0125832 A1 | 5/2015 | Tran |
| 2015/0126833 A1 | 5/2015 | Anderson et al. |
| 2015/0126848 A1 | 5/2015 | Baker et al. |
| 2015/0126876 A1 | 5/2015 | Lee et al. |
| 2015/0127061 A1 | 5/2015 | Ternes et al. |
| 2015/0127066 A1 | 5/2015 | Grill, Jr. et al. |
| 2015/0127067 A1 | 5/2015 | Ternes et al. |
| 2015/0133306 A1 | 5/2015 | Cronin |
| 2015/0133307 A1 | 5/2015 | Zhang et al. |
| 2015/0133795 A1 | 5/2015 | Tomaselli et al. |
| 2015/0133807 A1 | 5/2015 | Moorman et al. |
| 2015/0134019 A1 | 5/2015 | Moffitt et al. |
| 2015/0134315 A1 | 5/2015 | Sarmiento et al. |
| 2015/0135310 A1 | 5/2015 | Lee |
| 2015/0137988 A1 | 5/2015 | Gravenstein et al. |
| 2015/0139977 A1 | 5/2015 | Weiner et al. |
| 2015/0141846 A1 | 5/2015 | Sanchez et al. |
| 2015/0141857 A1 | 5/2015 | Nallathambi et al. |
| 2015/0141860 A1 | 5/2015 | Linker |
| 2015/0141861 A1 | 5/2015 | Trayanova et al. |
| 2015/0141863 A1 | 5/2015 | Kassab et al. |
| 2015/0142069 A1 | 5/2015 | Sambelashvili |
| 2015/0142070 A1 | 5/2015 | Sambelashvili |
| 2015/0148635 A1 | 5/2015 | Benaron |
| 2015/0157218 A1 | 6/2015 | Ahmad et al. |
| 2015/0157239 A1 | 6/2015 | Rissacher et al. |
| 2015/0157258 A1 | 6/2015 | Beattie et al. |
| 2015/0157269 A1 | 6/2015 | Lisogurski et al. |
| 2015/0157387 A1 | 6/2015 | OuYang et al. |
| 2015/0161629 A1 | 6/2015 | Verma |
| 2015/0164339 A1 | 6/2015 | Xu et al. |
| 2015/0164340 A1 | 6/2015 | Bedingham et al. |
| 2015/0164349 A1 | 6/2015 | Gopalakrishnan et al. |
| 2015/0164355 A1 | 6/2015 | Brockway et al. |
| 2015/0164358 A1 | 6/2015 | Moorman et al. |
| 2015/0164375 A1 | 6/2015 | Schindhelm et al. |
| 2015/0164433 A1 | 6/2015 | Halperin et al. |
| 2015/0165223 A1 | 6/2015 | Babaeizadeh et al. |
| 2015/0170052 A1 | 6/2015 | Abdul Rahman et al. |
| 2015/0171998 A1 | 6/2015 | Baheti et al. |
| 2015/0173631 A1 | 6/2015 | Richards et al. |
| 2015/0174307 A1 | 6/2015 | Eckman et al. |
| 2015/0174408 A1 | 6/2015 | Grill, Jr. et al. |
| 2015/0178631 A1 | 6/2015 | Thomas et al. |
| 2015/0181822 A1 | 7/2015 | Daetwyler et al. |
| 2015/0182160 A1 | 7/2015 | Kim et al. |
| 2015/0190060 A1 | 7/2015 | Addison et al. |
| 2015/0190088 A1 | 7/2015 | Chen et al. |
| 2015/0190636 A1 | 7/2015 | Simon et al. |
| 2015/0190637 A1 | 7/2015 | Simon et al. |
| 2015/0196213 A1 | 7/2015 | Pandia et al. |
| 2015/0196256 A1 | 7/2015 | Venkatraman et al. |
| 2015/0201853 A1 | 7/2015 | Hong et al. |
| 2015/0201854 A1 | 7/2015 | Hong et al. |
| 2015/0201859 A1 | 7/2015 | Baker et al. |
| 2015/0204559 A1 | 7/2015 | Hoffberg et al. |
| 2015/0206214 A1 | 7/2015 | Adjaoute |
| 2015/0208939 A1 | 7/2015 | Zigel et al. |
| 2015/0216426 A1 | 8/2015 | Burton et al. |
| 2015/0216431 A1 | 8/2015 | Pahlevan et al. |
| 2015/0216433 A1 | 8/2015 | Thakur et al. |
| 2015/0216480 A1 | 8/2015 | Nagata et al. |
| 2015/0216483 A1 | 8/2015 | Sevcencu et al. |
| 2015/0220486 A1 | 8/2015 | Karakonstantis et al. |
| 2015/0223708 A1 | 8/2015 | Richards et al. |
| 2015/0223711 A1 | 8/2015 | Raeder et al. |
| 2015/0223733 A1 | 8/2015 | Al-Alusi |
| 2015/0223756 A1 | 8/2015 | Nagata et al. |
| 2015/0223863 A1 | 8/2015 | Ghosh |
| 2015/0234976 A1 | 8/2015 | Chen et al. |
| 2015/0238091 A1 | 8/2015 | Iyer et al. |
| 2015/0238106 A1 | 8/2015 | Lappalainen et al. |
| 2015/0238147 A1 | 8/2015 | Figgatt et al. |
| 2015/0238148 A1 | 8/2015 | Georgescu et al. |
| 2015/0244946 A1 | 8/2015 | Agaian et al. |
| 2015/0245782 A1 | 9/2015 | Morland et al. |
| 2015/0246195 A1 | 9/2015 | Baker, Jr. et al. |
| 2015/0251012 A1 | 9/2015 | Olson |
| 2015/0257668 A1 | 9/2015 | Braojos Lopez et al. |
| 2015/0257671 A1 | 9/2015 | Laughner et al. |
| 2015/0257700 A1 | 9/2015 | Fu |
| 2015/0257712 A1 | 9/2015 | Sarrafzadeh et al. |
| 2015/0257715 A1 | 9/2015 | Quan et al. |
| 2015/0261926 A1 | 9/2015 | Kasabov |
| 2015/0265161 A1 | 9/2015 | Hernandez et al. |
| 2015/0265164 A1 | 9/2015 | Gopalakrishnan et al. |
| 2015/0265174 A1 | 9/2015 | Shakibi Gilani |
| 2015/0265175 A1 | 9/2015 | Shakibi Gilani |
| 2015/0265348 A1 | 9/2015 | Avitall et al. |
| 2015/0269825 A1 | 9/2015 | Tran |
| 2015/0272457 A1 | 10/2015 | Etemad et al. |
| 2015/0272464 A1 | 10/2015 | Armoundas |
| 2015/0283027 A1 | 10/2015 | Lampe et al. |
| 2015/0286779 A1 | 10/2015 | Bala et al. |
| 2015/0288573 A1 | 10/2015 | Baughman et al. |
| 2015/0289210 A1 | 10/2015 | Zhao et al. |
| 2015/0289777 A1 | 10/2015 | Linker |
| 2015/0289807 A1 | 10/2015 | Narayan et al. |
| 2015/0290453 A1 | 10/2015 | Tyler et al. |
| 2015/0297104 A1 | 10/2015 | Chen et al. |
| 2015/0297111 A1 | 10/2015 | Kassab |
| 2015/0297112 A1 | 10/2015 | Kassab et al. |
| 2015/0297907 A1 | 10/2015 | Zhang |
| 2015/0305632 A1 | 10/2015 | Najarian et al. |
| 2015/0320316 A1 | 11/2015 | Dhawan |
| 2015/0342478 A1 | 12/2015 | Galen et al. |
| 2015/0342488 A1 | 12/2015 | Laughner et al. |
| 2015/0342490 A1 | 12/2015 | Sachin et al. |

(56) References Cited

U.S. PATENT DOCUMENTS

| | | |
|---|---|---|
| 2015/0351699 A1 | 12/2015 | Addison et al. |
| 2015/0352367 A1 | 12/2015 | Quan et al. |
| 2015/0352369 A1 | 12/2015 | Quan et al. |
| 2015/0353880 A1 | 12/2015 | Clark et al. |
| 2015/0355459 A1 | 12/2015 | Shen et al. |
| 2015/0356350 A1 | 12/2015 | Awad |
| 2015/0359441 A1 | 12/2015 | Giovangrandi et al. |
| 2015/0359452 A1 | 12/2015 | Giovangrandi et al. |
| 2015/0359467 A1 | 12/2015 | Tran |
| 2015/0359486 A1 | 12/2015 | Kovacs et al. |
| 2015/0359492 A1 | 12/2015 | Giovangrandi et al. |
| 2015/0362360 A1 | 12/2015 | Kovacs et al. |
| 2015/0363108 A1 | 12/2015 | Kumar |
| 2015/0363193 A1 | 12/2015 | Chmiel et al. |
| 2015/0363194 A1 | 12/2015 | Chmiel et al. |
| 2015/0366511 A1 | 12/2015 | Addison et al. |
| 2015/0366518 A1 | 12/2015 | Sampson |
| 2015/0366532 A1 | 12/2015 | Voigt et al. |
| 2015/0374300 A1 | 12/2015 | Najarian et al. |
| 2015/0374983 A1 | 12/2015 | Simon et al. |
| 2016/0000346 A1 | 1/2016 | Lo et al. |
| 2016/0000350 A1 | 1/2016 | Zhang |
| 2016/0001089 A1 | 1/2016 | Allavatam et al. |
| 2016/0007907 A1 | 1/2016 | Lancaster et al. |
| 2016/0007932 A1 | 1/2016 | Laughner et al. |
| 2016/0008613 A1 | 1/2016 | Snyder |
| 2016/0022156 A1 | 1/2016 | Kovacs et al. |
| 2016/0022164 A1 | 1/2016 | Brockway et al. |
| 2016/0022166 A1 | 1/2016 | Stadler et al. |
| 2016/0022999 A1 | 1/2016 | Zhang et al. |
| 2016/0023013 A1 | 1/2016 | Greenhut et al. |
| 2016/0024156 A1 | 1/2016 | Barouch et al. |
| 2016/0033319 A1 | 2/2016 | Kovacs |
| 2016/0033622 A1 | 2/2016 | Martone et al. |
| 2016/0034634 A9 | 2/2016 | Hong et al. |
| 2016/0038037 A1 | 2/2016 | Kovacs |
| 2016/0038038 A1 | 2/2016 | Kovacs |
| 2016/0038091 A1 | 2/2016 | Krishnaswamy et al. |
| 2016/0041174 A1 | 2/2016 | Chinnaiyan et al. |
| 2016/0045123 A1 | 2/2016 | Bar-Tal et al. |
| 2016/0051203 A1 | 2/2016 | Furness et al. |
| 2016/0051205 A1 | 2/2016 | Al-Ali et al. |
| 2016/0051233 A1 | 2/2016 | Mo et al. |
| 2016/0051822 A1 | 2/2016 | Guez |
| 2016/0058301 A1 | 3/2016 | Shusterman |
| 2016/0058308 A1 | 3/2016 | Robinson |
| 2016/0066788 A1 | 3/2016 | Tran et al. |
| 2016/0066799 A1 | 3/2016 | Berkow |
| 2016/0066860 A1 | 3/2016 | Sternickel et al. |
| 2016/0066881 A1 | 3/2016 | Li et al. |
| 2016/0067433 A1 | 3/2016 | Martin et al. |
| 2016/0073313 A1 | 3/2016 | Hejazi et al. |
| 2016/0073959 A1 | 3/2016 | Eagle et al. |
| 2016/0073965 A1 | 3/2016 | Addison et al. |
| 2016/0074667 A1 | 3/2016 | Sullivan et al. |
| 2016/0081561 A1 | 3/2016 | Huang et al. |
| 2016/0081573 A1 | 3/2016 | Niebauer et al. |
| 2016/0087603 A1 | 3/2016 | Ricci et al. |
| 2016/0095531 A1 | 4/2016 | Narayan et al. |
| 2016/0098835 A1 | 4/2016 | Zhao et al. |
| 2016/0100787 A1 | 4/2016 | Leung et al. |
| 2016/0100803 A1 | 4/2016 | Korzinov et al. |
| 2016/0100817 A1 | 4/2016 | Hussain |
| 2016/0106378 A1 | 4/2016 | Kyal et al. |
| 2016/0113618 A1 | 4/2016 | Su et al. |
| 2016/0114162 A1 | 4/2016 | Sheldon et al. |
| 2016/0114168 A1 | 4/2016 | Demmer et al. |
| 2016/0114169 A1 | 4/2016 | Sheldon et al. |
| 2016/0120418 A1 | 5/2016 | Oksala et al. |
| 2016/0120431 A1 | 5/2016 | Habte et al. |
| 2016/0120433 A1 | 5/2016 | Hughes et al. |
| 2016/0120434 A1 | 5/2016 | Park et al. |
| 2016/0120464 A1 | 5/2016 | Lau et al. |
| 2016/0128630 A1 | 5/2016 | Warren et al. |
| 2016/0128641 A1 | 5/2016 | Fonseca et al. |
| 2016/0135705 A1 | 5/2016 | Liu et al. |
| 2016/0135754 A1 | 5/2016 | Marshall et al. |
| 2016/0136431 A1 | 5/2016 | Grill et al. |
| 2016/0140834 A1 | 5/2016 | Tran |
| 2016/0143543 A1 | 5/2016 | Zhang |
| 2016/0143594 A1 | 5/2016 | Moorman et al. |
| 2016/0148531 A1 | 5/2016 | Bleich et al. |
| 2016/0151013 A1 | 6/2016 | Atallah et al. |
| 2016/0152438 A1 | 6/2016 | Siikonen et al. |

* cited by examiner

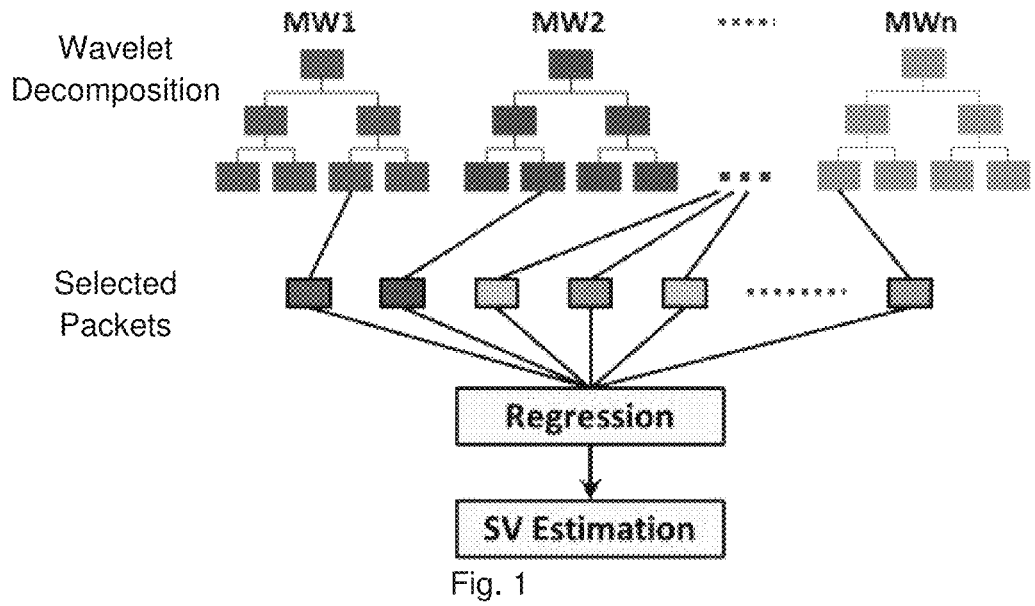

Fig. 1

Procedure GA

```
begin t = 0;
  while the limit for soft restarts is not reached do begin
    if number of generations is equal to zero initialize P(t);
    else
      t=t+1;
      P(t) = random population + best individual from P(t-1); end
    evaluate structures in P(t);
    while convergence termination condition not satisfied do begin
      t=t+1;
      select C(t) from P(t-1); recombine structures in
      C(t); evaluate structures in C(t); select P(t) from
      C(t) and P(t-1);
    end
    number of soft restarts ++; end
end
```

Fig. 2

SYSTEM AND METHOD FOR INFRASONIC CARDIAC MONITORING

CROSS REFERENCE TO RELATED APPLICATIONS

The present application is a Non-provisional of, and claims priority under 35 U.S.C. § 119(e) from, U.S. Provisional Patent Application No. 62/175,686, filed Jun. 15, 2015, the entirety of which is expressly incorporated herein by reference.

BACKGROUND OF THE INVENTION

The present application incorporates the following material by reference, in its entirety: Ohad BarSimanTov, Ph.D. Dissertation, Binghamton University (2014, embargoed).

Cardiac Output (CO) is the one of the most important measurements for assessing human health. CO refers to the volume (in liters) of blood pumped out by the left ventricle to the body per minute. Unfortunately, the lack of accuracy and difficultly of measuring this parameter in the primary care and home care environments has drastically limited its use. As a result, other more readily obtained assessments are commonly used to provide an estimation of CO, for example, heart rate, respiratory rate, blood pressure, body temperature (i.e., the vital signs).

A vital signs assessment of an individual's health is undertaken during any hospital admission, any doctor visit, by a medic, or at the start of almost any healthcare intervention. The reason for this assessment is to check how well the vital organs of the body, lungs, heart, etc., are working, and thereby identify any early signs of illness. There are four Vital Signs commonly used to quickly assess the health status of an individual [1]; pulse rate, blood pressure, breathing rate, and body temperature. The pulse rate also is called heart rate, which is the number of heart beats per minute. Heart Rate (HR) can readily be measured by sensing the pulsations in an artery. Blood pressure is typically measured at the arteries of the arm and represents the driving force of blood through the arterial system. The systolic pressure is the high pressure value, and indicates the heart's contraction force. The diastolic pressure is lower pressure value and happens during the relaxation phase of the heart. The blood pressure and pulse rate provides only a very crude estimate of Cardiac Output (CO). Cardiac Output is commonly compared to the person's body surface areas (BSA) which can be obtained through the person's height and weight. Cardiac Index (CI) is the ratio of CO to BSA and is relatively constant across the population in healthy individuals, though it decays with increasing age. The third vital sign is breathing rate and is obtained by counting the number of times the person's chest rises and falls in one minute. Usually, a physician will pay attention to abnormal sounds during respiration, which can provide information about the person's respiratory condition. The last vital sign is the body temperature, which provides a measure of the individuals' thermo-regulatory status, a critical aspect of health in a homoeothermic organism.

Introduction of a dye into the blood stream provides one method to measure CO. The Fick method uses two catheters to extract blood samples from the pulmonary artery and from the aorta and measure the oxygen levels in both. The dye dilution uses a single catheter to extract blood samples from the aorta after the dye was injected in the median antecubital vein. Around 1960s, the dye dilution came to be viewed as the most accurate technique to measure CO. In 1970s the pulmonary artery catheter (PAC) was introduced and became the 'gold standard' apparatus as it could be used in both dye-dilution and thermo-dilution methods, which involves just one catheter to inject a solution to the right atrium and measure its change in the pulmonary artery. Since then, invasive techniques using PAC, and other arterial catheters, are widely used in hospital settings. However, these invasive methods and techniques introduce significant risk of deleterious complications such as bleeding, pneumothorax, and infection and widespread use of these devices is falling out of favor. Therefore, non-invasive CO monitoring measurements are preferred by physicians and patients.

Numerous non-invasive cardiac monitoring technology have been developed over the years to address the need for non-invasive cardiac monitoring, including Electrocardiogram (ECG), Computed Tomography (CT), Magnetic Resonance Imaging, Doppler Ultrasound, Echocardiogram, and Bio-impedance. All of these improve patient safety and significantly reduce complications. Some of them also dramatically reduce the cost of cardiac monitoring. ECG does not provide any specific information about the mechanical activity (i.e. pumping activity) of the heart, only the electrical activity. Similarly, CT and MRI provide only static images of the heart. Doppler Ultrasound and Bioimpedance provide estimates of the volume of blood ejected by the heart during each contraction, which when multiplied by heart rate, provides an estimate of CO.

The total volume of blood that the heart pumps during each contraction is referred to as the stroke volume. Cardiac output (CO) is simply the product of the heart rate and stroke volume. Stroke volume depends on atrial filling pressure, the end diastolic pressure in the ventricle (backpressure), and the contractility of the ventricle. Typically, a healthy cardiac muscle will eject between 55% and 70% of the ventricular volume, or approximately 70 ml [23]. As the cardiovascular system is a closed system, the right ventricle volume and ejection fraction roughly equal to those on the left ventricle at any given point in time. A complete cardiac cycle occurs during each heartbeat, both atria simultaneously contract followed by contraction of the ventricles [24]. During contraction, the blood pressure in the left ventricle varies rapidly from about 80 mmHg (typical diastolic pressure) to about 120 mmHg (typical systolic pressure). The right ventricle pressures are much lower, ranging from 2 mmHg to 30 mmHg. As all tissues are critically dependent on adequate blood perfusion to maintain normal function, a measure of cardiac output can provide important information regarding the cause of any tissue or organ system failure. Based on an individual's gender, age, and training levels, HR and SV differ, but the heart supplies the needed amount of blood to the entire body by regulating these two factors. If one component is lower the other adapts to a higher level during either rest or exercise. Because HR can vary over a range of 2-3 fold, and SV can vary over a range of 2-3 fold, the heart has the capability to increase its output by up to roughly tenfold. The ability to attain this full operating range is the essence of athletic training, therefore, accurate, non-invasive, continuous CO monitoring has major applications not just in the healthcare domain, but also in the athletic domain.

The heart generates sounds during each cardiac cycle due to the flow of blood through the heart; four heart sounds are commonly defined. The first two, S1 and S2, are normal and associated with the closing of the mitral and tricuspid valves and the aortic and pulmonary valves during the beginning of systolic and diastolic phases respectively [37]. These heart sounds can provide a basis for synchronization of heart contraction timing. The third and the fourth heart sounds, S3 and S4, may be normal or abnormal and are the result of turbulent flow through the values, or regurgitation back through valve. These latter heart sounds are often referred to as murmurs.

Following the ECG P wave, contraction of the atria is associated with left ventricular volume increase and small left ventricle and left atrium pressure increase. Following The ECG QRS complex the ventricles contract and the left ventricle pressure increases rapidly. This causes the closing of the tricuspid valve, which produces the first heart sound, representing the beginning of the systolic phase. The left ventricle pressure continues to increase and the aorta semilunar valve opens when the left ventricle pressure exceeds the aorta pressure. As a result, the aortic pressure is increased and the left ventricle volume decreases. The blood from the left ventricle is expelled into the aorta until the relaxation phase begins. At this stage, the aortic valve closes and produces the second heart sound which is the end of the systole phase and the beginning for the diastole phase. The left ventricle continues to relax, and then the tricuspid valve opens and oxygenated blood enters to the left ventricle. These flows and volumetric changes produce forces, and motions of the chest wall, which have physiological correlates.

In the 19 century it was first proposed that measurements of chest wall movement during cardiac muscle contraction could serve as a useful measure of stroke volume. Many techniques and methods have been developed to capture cardiac activity non-invasively using sensing techniques, including Sphygmography, Apex-cardiogram, Mechanocardiogram, Vibrocardiogram, accelerocardiogram, Cardiokymogram, Ballistocardiogram, Kinetocardiogram, Seismocardiogram, and other related methods were introduced to measure cardiac activity from body and/or chest motion. All of these methods measure a mechanical motion below 20 Hz, which is at or below the audible range of human hearing. Acoustic signals below the range of human hearing are referred to as infrasonic [64].

The Vibrocardiogram (VbCG) provides for measurement of the phases of isometric contraction, ejection, systole and diastole obtained from the precordial vibration tracing, with an accuracy as good as that realized with direct cardiac catheterization [79, 80]. Those recordings permit the total energy spectrum of the heart in a displacement form, like the ACG. However, the VbCG signal, is obtained using a microphone, which provides a measure of the velocity of the chest motion. If this signal is integrated, it provides the displacement of the chest wall. The VbCG waveform typically consists of four main deflections [79]. The segment between J2 and L is considered to be the ejection time (ET) and the isometric contraction time (ICT) is considered to be between R left and J2. However, in later studies it has been found that the isometric contraction is happening after the ECG R way. The comparison between the dye dilution and VbCG has been explored and a good correlation of the ejection time has been found (r=0.9). Also, an estimation of cardiac output has been shown to be possible [81].

The recording location of the VbCG is defined as the area between the 4th to the 5th left intercostal spaces near the sternum, similarly to ACG, accelerocardiogram [82], and Cardiokymography (CKG) [84]. The investigation of heart diseases using these methods has also been described [81, 83]. VbCG and Accelerocardiogram record the acceleration of the chest wall at the apex location (behind the fifth left intercostal space, 8 to 9 cm from the mid-sternal line, slightly medial to the midclavicular line.) ACG and CKG record the displacement of the chest wall at the apex location. These four methods require breath holding while the subject is lying down. Moreover, the signal varies due to the position of the transducer on the chest, though traditionally the sensor is located exclusively at the apex, and the interpretation of the signal at other locations is not generally interpreted. Some of the recent publications have used optical sensing devices to measure cardiac activities [85, 86] and some investigators have concluded that these techniques have the capability and certain advantages for long term cardiac monitoring [87].

An alternative method of recording precordial (the region of the chest over the heart) movements is the Kinetocardiogram (KCG) [103, 104, 105]. Like the ACG and BCG, KCG records the displacement of a human body as a result of cardiac activity. This method was very similar to ACG, but the recordings were taken at specific known locations on the chest like the V1-V6 in ECG, and included the apex location. The recordings utilize a sensitive piezoelectric transducer (accelerometer) during the end of normal expiration [103]. The recordings demonstrate a range of motion over the chest of about two hundred microns.

Seismocardiogram (SCG) is a similar method which records the acceleration of the chest wall; however, the recording location is at the sternum, similarly to one of the KCG recording locations. SCG was first described in 1961 [107]. In 1990 SCG recordings were performed using an accelerometer and microprocessor based signal analysis device [108]. The frequency range of the SCG signal was found to be 0.3 to 50 Hertz [108]. Moreover, this method has been investigated and compared to left ventricular function [109] and the relationship between SCG and Echocardiogram [110].

The idea of integrating a portable Seismocardiography signal to measure CO has therefore existed for quite some time [115, 116, 117]. However, it is not fully developed.

There are many mathematical tools used to analyze a signal in the frequency domain. The traditional Fourier and Laplace methods work well in smooth continuous signals, for which the statistics properties do not vary in time (i.e. the signals are stationary). They are widely used in science and engineering and suitable when the recorded signal is stationary. The basis functions, however, are sine and cosine functions, which extend over infinite time intervals and are therefore not suited for non-stationary signals [122]. Short Time Fourier Transform (STFT), which is used to analyze small segments of a signal, is more suitable for non-stationary signals if the statistical properties of the signal vary slowly relative to the dominant frequency of the signal. In the context of infrasonic vibrations associated with heart activity, the received signal consists of many frequencies which are very close to frequency of variation (~1 Hz, i.e. the heart rate frequency) and is not suitable for the use of STFT. Wavelet analysis is a tool which can be used to extract spectral information where ST Fourier methods fail [124]. Wavelet analysis transforms signals into a two dimensional time-frequency domain, utilizing a series of convolution operations on the signal against particular filters at various positions and time scales. This process not only separates high frequency component from low frequency components, but as well, the wavelet scaling process allows one to look at a signal within a small window, and notice the time location of small and high frequency features. In addition, noises can be subtracted fairly easily from the recorded signal, which makes this tool very powerful in many applications: data compression, signal and image processing, music analysis, speech discrimination, quantum physics, optics, earthquake-prediction, radar, human vision, seismic geology, and more. The mathematical proof of the transformations is provided in the papers [124-126].

Wavelet analysis typically consists of three major stages. The first is decomposition, which separates the signal's high frequency components from the low frequency components. This process continues recursively through different stages and provides signal analysis while convolving the signal with high pass and low pass filters. Based on the "cost" of each decomposition level the efficiency of the analysis is calculated to ensure the desired information is extracted from the signal. The second stage is called threshold, where each of the decomposed segments, called packets, is processed via mathematical computations. The last stage is signal reconstruction, which collects the packets and reconstructs the desired signal. This three step process is very common in data compression, and image processing.

The set of high pass and low pass filters are scaled functions of the Mother Wavelet. A Mother Wavelet is a wavelet prototype function which is adapted (scaled and shifted) during the procedure of wavelet analysis. The analysis is performed with a high pass filter and a low pass filter using the Mother Wavelet coefficients. Different Mother wavelets will produce different outputs and different signal information [126]. Therefore, a more suitable mother wavelet function will provide better information extraction and better noise reduction from the original signal.

The original signal can be reconstructed using all scalings and details of the decomposed signal with knowledge of the decomposed mother wavelet. Wavelet decomposition separates the signal to details g[n] and scaling h[n] coefficients with the scaling and details decimated by factors of two. Each level of decomposition can be obtained from the scaling factor and separated into scaling and details again. Similarly, the reconstruction process can use the scaling and detail packets to reconstruct the previous decomposition level packets until the original is reconstructed. The scaling h[n] and detail g[n] are convolved with the Mother wavelet until the original signal is reconstructed.

Wavelet analysis has become one of the most commonly used digital signal processing tools, with applications in data compression, image processing, time series data filtering, material detection and de-noising [125, 189]. Over the past two decades, the use of wavelet analysis has increased rapidly in the biomedical field with analyses being applied to remove base line variation and high frequency components from the electrocardiogram (ECG) and to distinguish specific features within the ECG waveform [153, 154]. Wavelets have also been used in analysis of electromyograms (EMG) [155, 156], mechanomyograms (MMG) [157], electroencephalograms (EEG) [158, 159], seismocardiograms [115], and other medical applications. Wavelet analysis is widely used to de-noise data and to separate observed components where decomposition, thresh-holding, and reconstruction are computed. Of course, physiological recordings are not signals (i.e. messages) per se. In communication systems, the original transmitted message is known and can be compared to the received signal; physiologic recordings can only be interpreted based on a set of assumptions regarding the performance of the physiologic system, rather than comparing to a-priori signal. Accordingly, the appropriate processing algorithm must be identified by correlating the output produced by various analyses to some system characteristic of interest.

See, e.g., U.S. Patent and U.S. Pat. Nos. 9,008,367, 9,008,754, 9,008,762, 9,011,338, 9,014,453, 9,014,789, 9,014,790, 9,014,809, 9,020,585, 9,026,193, 9,026,200, 9,028,405, 9,028,407, 9,031,301, 9,031,642, 9,031,649, 9,033,883, 9,033,887, 9,033,893, 9,037,223, 9,037,224, 9,042,619, 9,042,952, 9,042,958, 9,044,144, 9,044,149, 9,044,171, 9,044,558, 9,049,981, 9,049,985, 9,050,007, 9,050,014, 9,055,871, 9,055,884, 9,056,172, 9,060,669, 9,060,683, 9,060,689, 9,060,695, 9,060,722, 9,060,733, 9,066,672, 9,066,679, 9,066,680, 9,066,686, 9,066,708, 9,069,130, 9,072,437, 9,072,438, 9,075,446, 9,076,202, 9,079,060, 9,081,148, 9,084,531, 9,084,576, 9,084,611, 9,086,467, 9,087,368, 9,089,269, 9,092,691, 9,095,266, 9,095,313, 9,095,505, 9,097,756, 9,101,286, 9,101,772, 9,107,571, 9,107,584, 9,107,586, 9,107,623, 9,107,624, 9,113,794, 9,113,795, 9,113,826, 9,113,830, 9,114,260, 9,116,835, 9,119,547, 9,119,573, 9,125,574, 9,125,577, 9,125,578, 9,126,050, 9,131,852, 9,131,864, 9,131,902, 9,136,980, 9,138,150, 9,144,394, 9,147,268, 9,149,219, 9,149,231, 9,149,244, 9,149,645, 9,155,482, 9,155,484, 9,155,893, 9,161,705, 9,162,074, 9,163,216, 9,167,971, 9,168,380, 9,168,385, 9,168,419, 9,171,353, 9,173,566, 9,173,579, 9,173,909, 9,174,061, 9,175,095, 9,176,319, 9,178,330, 9,179,890, 9,180,043, 9,180,300, 9,183,351, 9,183,626, 9,186,066, 9,186,067, 9,186,068, 9,186,079, 9,186,105, 9,186,106, 9,186,521, 9,192,328, 9,192,336, 9,192,446, 9,197,173, 9,198,582, 9,198,586, 9,198,604, 9,198,616, 9,198,634, 9,199,078, 9,201,902, 9,202,008, 9,204,796, 9,208,173, 9,208,557, 9,208,587, 9,209,782, 9,211,413, 9,215,298, 9,215,980, 9,215,987, 9,215,991, 9,216,001, 9,216,065, 9,220,440, 9,220,455, 9,220,459, 9,220,460, 9,220,467, 9,220,856, 9,226,660, 9,226,665, 9,226,676, 9,236,046, 9,237,855, 9,239,951, 9,241,667, 9,242,090, 9,245,091, 9,247,901, 9,248,288, 9,248,306, 9,249,200, 9,254,089, 9,254,093, 9,254,095, 9,254,102, 9,254,383, 9,258,561, 9,259,167, 9,259,591, 9,261,573, 9,262,826, 9,264,877, 9,267,936, 9,269,127, 9,277,871, 9,277,956, 9,278,226, 9,282,896, 9,282,902, 9,282,908, 9,282,910, 9,282,911, 9,282,925, 9,282,931, 9,286,662, 9,289,133, 9,289,136, 9,289,150, 9,289,165, 9,289,167, 9,289,545, 9,294,074, 9,295,391, 9,301,703, 9,301,705, 9,302,111, 9,304,121, 9,305,334, 9,305,350, 9,307,407, 9,307,917, 9,308,042, 9,308,052, 9,314,181, 9,314,305, 9,319,028, 9,319,212, 9,320,491, 9,324,005, 9,324,141, 9,324,144, 9,326,682, 9,326,697, 9,326,722, 9,327,130, 9,330,092, 9,330,459, 9,332,357, 9,332,939, 9,332,942, 9,339,202, 9,339,206, 9,339,230, 9,339,241, 9,339,436, 9,339,662, 9,340,589, 9,341,783, 9,345,413, 9,345,609, 9,345,888, 9,351,640, 9,351,642, 9,351,649, 9,351,661, 9,351,668, 9,351,674, 9,352,057, 9,352,165, 9,354,115, 9,356,731, RE45512, RE45725, RE45922, U.S. Pat. Nos. 9,026,202, 9,026,199, 9,011,346, 8,998,830, 8,992,434, 8,983,854, 8,979,731, 8,979,730, 8,942,779, 8,905,928, 8,882,684, 8,880,156, 8,870,780, 8,862,231, 8,858,449, 8,840,564, 8,834,364, 8,827,918, 8,821,418, 8,798,726, 8,798,714, 8,790,264, 8,764,653, 8,747,312, 8,734,360, 8,731,646, 8,706,204, 8,700,137, 8,696,569, 8,679,034, 8,679,030, 8,603,010, 8,594,787, 8,585,607, 8,562,526, 8,540,651, 8,517,953, 8,509,881, 8,491,492, 8,482,416, 8,475,367, 8,403,865, 8,376,964, 8,376,954, 8,262,582, 8,249,698, 8,024,044, 7,785,257, 7,715,894, 7,660,632, 7,417,536, 7,396,331, 7,314,451, 7,286,871, 7,269,537, 7,077,810, 7,043,293, 7,019,641, 6,993,378, 6,840,907, 6,547,743, 6,535,754, 6,478,744, 6,370,481, 6,179,783, 6,152,879, 6,053,872, 6,050,950, 5,964,720, RE35122, 5,445,162, 5,197,490, 4,934,372, 4,928,692, 4,926,866, 4,911,167, 4,895,155, 4,893,633, 4,889,130, 4,889,123, 4,884,578, 4,848,350, 4,838,275, 4,836,215, 4,817,610, 4,802,486, 4,738,264, 4,681,098, 4,679,569, 4,657,025, 4,519,395, 4,195,643, 4,036,215, 3,960,140, 9,028,407, 9,028,405, 9,026,214, 9,026,201, 9,014,809, 9,002,453, 9,002,446, 8,998,820, 8,996,110, 8,996,107, 8,968,195, 8,961,185, 8,954,146, 8,942,799, 8,934,970, 8,923,965, 8,918,172, 8,909,329, 8,888,710, 8,886,311, 8,862,226, 8,818,524, 8,798,731, 8,792,998, 8,768,461, 8,764,651, 8,750,992, 8,750,981, 8,747,336, 8,747,313, 8,738,119, 8,738,111, 8,727,978, 8,708,903, 8,702,616, 8,700,146, 8,684,925, 8,684,922, 8,684,900, 8,680,991, 8,652,038, 8,649,853, 8,634,930, 8,630,707, 8,626,281, 8,620,427, 8,620,426, 8,617,082, 8,606,349, 8,594,805, 8,588,906, 8,586,932, 8,583,233, 8,583,230, 8,583,229, 8,532,770, 8,531,291, 8,525,687, 8,525,673, 8,515,535, 8,515,534, 8,509,890, 8,500,636, 8,494,829, 8,475,368, 8,473,068, 8,473,055, 8,461,988, 8,456,309, 8,452,389, 8,449,471, 8,445,851, 8,425,415, 8,423,125, 8,401,640, 8,380,308, 8,346,360, 8,328,718, 8,326,429, 8,326,428, 8,323,189, 8,323,188, 8,321,003, 8,301,241, 8,287,459, 8,285,373, 8,275,463, 8,255,042, 8,251,911, 8,244,355, 8,223,023, 8,214,033, 8,209,010, 8,160,701, 8,145,304, 8,121,673, 8,115,640, 8,108,036, 8,103,333, 8,073,541, 8,027,724, 8,025,624, 8,010,194, 8,005,543, 8,000,773, 7,963,925, 7,953,479, 7,949,399, 7,949,398, 7,908,004, 7,877,146, 7,869,876, 7,869,869, 7,856,268, 7,850,616, 7,848,816, 7,846,104, 7,813,805, 7,797,050, 7,787,946, 7,774,055, 7,769,446, 7,733,224, 7,689,283, 7,676,266, 7,672,728, 7,670,295, 7,650,189, 7,636,600, 7,577,478, 7,574,255, 7,558,622, 7,546,161, 7,539,533, 7,539,532, 7,494,459, 7,460,909, 7,338,436, 7,248,923, 7,206,636, 7,177,686, 7,139,609, 7,079,896, 7,039,462, 6,647,289, 6,551,252, 6,477,406, 6,370,424, 6,171,263, 6,155,976, 6,022,322, 5,782,884, 5,718,720, 5,507,785, 20160151013, 20160148531, 20160143594, 20160143543, 20160140834, 20160135754, 20160135705, 20160128641, 20160128630, 20160120464, 20160120434, 20160120433, 20160120431, 20160120418, 20160114169, 20160114168, 20160114162, 20160113618, 20160106378, 20160100817, 20160100803, 20160100787, 20160098835, 20160095531, 20160087603, 20160081573, 20160081561, 20160074667, 20160073965, 20160073959, 20160067433, 20160066881, 20160066860, 20160066799, 20160066788, 20160058308, 20160058301, 20160051822, 20160051233, 20160051205, 20160051203, 20160045123, 20160038091, 20160038038, 20160038037, 20160034634, 20160033319, 20160023013, 20160022999, 20160022216, 20160022164, 20160022156, 20160008613, 20160007932, 20160007907, 20160001089, 20160000350, 20160000346, 20150374983, 20150374300, 20150366532, 20150366518, 20150366511, 20150362360, 20150359492, 20150359486, 20150359467, 20150359452, 20150359441, 20150352369, 20150352367, 20150351699, 20150342490, 20150342488, 20150342478, 20150305632, 20150297907, 20150297112, 20150297111, 20150297104, 20150290453, 20150289807, 20150289777, 20150286779, 20150283027, 20150272464, 20150272457, 20150269825, 20150265348, 20150265175, 20150265174, 20150265164, 20150265161, 20150257715, 20150257712, 20150257700, 20150257671, 20150257668, 20150251012, 20150246195, 20150245782, 20150238148, 20150238147, 20150238106, 20150238091, 20150223863, 20150223756, 20150223733, 20150223711, 20150223708, 20150220486, 20150216483, 20150216480, 20150216433, 20150216431, 20150216426, 20150208939, 20150204559, 20150201859, 20150201854, 20150201853, 20150196256, 20150196213, 20150190637, 20150190636, 20150190088, 20150190060, 20150182160, 20150178631, 20150174307, 20150173631, 20150171998, 20150165223, 20150164433, 20150164375, 20150164358, 20150164355, 20150164349, 20150164340, 20150164339, 20150157387, 20150157269, 20150157258, 20150157239, 20150157218, 20150148635, 20150142070, 20150142069, 20150141863, 20150141861, 20150141860, 20150141857, 20150141846, 20150137988, 20150135310, 20150134019, 20150133807, 20150133795, 20150127067, 20150127061, 20150126876, 20150126848, 20150126833, 20150125832, 20150122018, 20150119711, 20150117741, 20150112606, 20150112452, 20150112409, 20150112220, 20150112212, 20150112211, 20150112209, 20150112208, 20150112159, 20150112158, 20150112157, 20150112156, 20150112155, 20150112154, 20150109124, 20150106020, 20150105695, 20150105681, 20150105631, 20150103360, 20150099946, 20150099941, 20150088214, 20150088016, 20150088004, 20150087947, 20150087931, 20150086131, 20150080746, 20150073234, 20150068069, 20150065835, 20150065815, 20150065814, 20150057512, 20150051452, 20150046095, 20150045684, 20150038856, 20150032178, 20150031969, 20150031964, 20150025394, 20150025393, 20150025336, 20150025335, 20150025334, 20150025328, 20150018637, 20150018632, 20150016702, 20150005655, 20150005594, 20150005646, 20140378849, 20140371574, 20140362013, 20140350361, 20140323821, 20140309543, 20140308930, 20140288551, 20140288442, 20140277241, 20140277239, 20140275925, 20140275886, 20140275829, 20140275824, 20140267299, 20140266787, 20140249429, 20140222115, 20140221859, 20140221786, 20140207204, 20140194702, 20140163425, 20140163368, 20140163343, 20140151563, 20140143064, 20140142451, 20140142444, 20140142437, 20140135645, 20140135634, 20140128953, 20140121476, 20140114370, 20140104059, 20140094875, 20140088676, 20140077946, 20140066798, 20140055284, 20140052209, 20140046209, 20140039333, 20140039330, 20140012144, 20140012099, 20140005496, 20130345591, 20130338460, 20130331904, 20130331661, 20130310700, 20130296962, 20130261473, 20130245722, 20130245502, 20130231574, 20130211482, 20130211291, 20130211271, 20130204122, 20130197597, 20130197375, 20130197322, 20130190835, 20130190645, 20130178718, 20130172691, 20130171599, 20130165819, 20130158415, 20130144178, 20130137998, 20130123873, 20130109989, 20130095459, 20130085401, 20130072807, 20130069780, 20130060297, 20130060296, 20130053926, 20130053913, 20130053912, 20130053907, 20130030487, 20130030486, 20130030484, 20130030315, 20130030314, 20130030312, 20130023957, 20130023956, 20130009783, 20130006317, 20120330373, 20120330109, 20120296228, 20120277545, 20120271382, 20120271371, 20120271177, 20120253419, 20120245476, 20120245464, 20120242501, 20120238800, 20120226126, 20120220835, 20120203090, 20120203077, 20120197333, 20120185012, 20120179216, 20120172742, 20120172741, 20120165892, 20120157861, 20120157856, 20120157798, 20120143072, 20120136263, 20120132211, 20120123279, 20120095357, 20120095352, 20120092157, 20120092156, 20120071792, 20120022844, 20120022384, 20120022350, 20120022336, 20120010677, 20110319782, 20110319778, 20110319776, 20110301660, 20110263994, 20110251502, 20110208016, 20110196442, 20110196441, 20110196254, 20110181422, 20110172500, 20110160656, 20110152974, 20110137110, 20110130671, 20110130670, 20110118614, 20110115624, 20110112442, 20110106558, 20110105930, 20110098770, 20110098583, 20110087115, 20110087113, 20110082511, 20110066205, 20110066042, 20110066041, 20110060235, 20110060230, 20110046508, 20110046498, 20110036801, 20110034811, 20110021928, 20110015704, 20110015703, 20110015702, 20110015468, 20100331908, 20100305634, 20100304864, 20100274219, 20100256701, 20100249628, 20100210921, 20100204550, 20100179438, 20100169810, 20100169122, 20100152795, 20100123587, 20100121406, 20100114207, 20100113944, 20100100150, 20100100148, 20100094147, 20100094102, 20100069768, 20100030090, 20100010556, 20090318987, 20090318779, 20090312612, 20090270746, 20090227877, 20090227876, 20090203972, 20090105556, 20090099473, 20090078875, 20090076401, 20090076350, 20090076349, 20090076348, 20090076346, 20090076343, 20090076342, 20090054758, 20090054742, 20090036940, 20090024044, 20080312523, 20080306397, 20080275349, 20080275314, 20080269625, 20080262367, 20080230705, 20080230702, 20080194975, 20080161877, 20080128626, 20080119749, 20080091114, 20080042067, 20080039904, 20080013747, 20080004904, 20080004672, 20080001735, 20070299349, 20070276270, 20070273504, 20070265533, 20070260285, 20070191742, 20070150006, 20070118054, 20070106170, 20070103328, 20070083243, 20070083128, 20070013509, 20060293607, 20060247542, 20060241510, 20060211909, 20060206159, 20060167334, 20060149139, 20060142634, 20060111754, 20060094967, 20050234289, 20050137480, 20050124864, 20050113666, 20040267086, 20040097802, 20030233132, 20030233034, 20030135127, 20030135097, 20030045806, 20020040192, 20020032386, each of which is expressly incorporated herein by reference in its entirety. These references disclose, for example, complementary technologies, aspects and details of implementation, applications, and the like.

The Mother Wavelet function is often selected based on the shape and characteristic of the feature one is trying to extract. Some functions are better at capturing amplitude and phase changes; others are better at synthesizing data and quantitative information. Domingues et al. [190] and Chourasia et al. [191] show examples, where selection of a particular mother wavelet provides better feature extraction than others. Rather than accepting such a trade-off by selecting a single basis set, it should be possible to combine information from multiple mother wavelets. See, U.S. Pat. No. 8,874,477, expressly incorporated herein by reference.

If one has inadequate a-priori understanding of the characteristics which need to be extracted for a particular application there may be advantages in performing multiple full tree decompositions using multiple mother wavelets, and then recombining specific packets to create a hybrid. While encouraging in principle, this approach soon faces the curse of dimensionality; the number of combinations increases factorially. Genetic Algorithms (GAs) have some ability to deal with combinational exploration, so this approach was explored.

Genetic Algorithms (GAs) and Wavelets have been combined recently in image processing for fault detection [160, 161], voice recognition [162], and other applications [163, 164], but these investigations used a binary encoding for packet selection. Previous investigations [149] imply that a better approach is to incorporate an index representation (genes are the indexes of the features to select from a possibly large pool of features), with a special subset selection crossover operator. This approach has been used in medical imaging, and also genomic and proteomic data mining [165, 166, 167], but not generally applied in time series data processing. In this case multiple filter banks from multiple mother wavelets were employed. Each mother wavelet was used to decompose data to provide a set of filter banks, also known as packets and then a GA was used to evaluate a subset of the filters specified in each chromosome (FIG. 1).

There are many types of Evolutionary Computations (EC). Each has strengths and weaknesses. Darwin's theorem influenced all of them. A brief introduction and history to GAs is provided and explains the differences between GA and other numerical methods. The no free lunch [138] theorem states there is not a universal algorithm to derive the global optimal solutions for all problems. Therefore, only a few ECs are investigated and explained in detail.

Evolutionary computation is a research domain, where computer algorithms are inspired by principles of natural evolution. Evolutionary computation has sub areas: evolutionary programming, evolution strategies, genetic algorithms, and genetic programming. All may be characterized as non-linear, stochastic search methods based on the mechanics of natural selection and natural genetics [138]. Survival of the fittest among the entire population provides the step forward to find the "optimal solution" from one generation to another. The three main mechanisms that drive evolution forward are reproduction, inheritance with variation, and natural selection. Usually, GAs use crossover and mutation to explore the landscape. Evolutionary Programming (EP) usually uses only mutation and emphasizes the evolution of behaviors. Evolution Strategies (ES) are based on adaptation and evolution, and traditionally used only mutation for variation. The selection process is often deterministic and based on fitness ranking and not on the evaluation value. In general, GAs work on a population of chromosomes. Each chromosome is represented by a string of genes, where each gene represents a variable in the evaluated chromosome. Based on chromosomes' evaluations, offspring are produced using crossover and mutation processes.

Evolution Strategies often employ more advanced mutation operators and often use smaller population sizes than GAs. Their solution representation and selection operators can be different from GAs. The best individuals from the population is allowed to produce offspring, which will represent the next population. The offspring are mutated and evaluated before they become the next generation. In some cases the new offspring will be combined with the previous population. The general principle of ES is as follows:

```
t=0
initialize(P(t=0));
evaluate (P(t=0));
while isNotTerminated( ) do
    P_p(t) = selectBest(μ, P(t));
    P_c(t) = reproduce(λ, P_p);
    mutate (P_c(t));
    evaluate (P_c(t));
    if (usePlusstrategy) then P=(t+1) = P_c(t) ∪ P(t);
    else P=(t+1) = P_c(t)
    t=t+1
end
```

Genetic Programming (GP) is often used to evolve computer programs and sometimes to derive mathematical equations to represent a solution to a problem. GP is able to model dynamic systems using evolved equations which best represent a solution to a system. The problem representation is encoded as a tree structure, where branches are evaluated in a specific order. Evolutionary programming (EP) is similar to GP, but the structure of the program is fixed, similar to GA. N numbers of genes can be represented where in every generation some genes are mutated and represent different operations. The data flow is similar to GA, but the new population is the mutated old population.

The search for an optimal solution is desired in every challenge. Non-linear, stochastic search, based on the mechanics of natural selection are what characterize Genetic Algorithms [139]. They are a particular evolutionary algorithm class that uses biology inspired techniques such as mutation, selection, inheritance and crossover (recombination). Survival of the fittest among the entire population with some mutation provides the step forward towards the optimal solution from one generation to another. A new set of artificial chromosomes or individuals (population) is created using some or all chromosomes in every generation. Some genes in these chromosomes are combined with new genes which were not explored before or were inherited from previous generations. This may be considered to correspond, to a son who looks like his father, but yet has minor variations which distinguish him and are carried on from previous generations, say his grandfather. Genetic Algorithms are randomized yet not simple random. They allow efficient exploitation of historical information combined with the new, and performance usually improves across generations.

The search for the best solution may not be possible mathematically and, or may cost unrealistic computation time and effort. There are three main types of search methods identified by the current literature: calculus-based, enumerative, and stochastic. Calculus-based methods have been explored widely and divide to two groups: indirect method, where search for local maxima is by solving a nonlinear set of equations directed from the gradient of the objective function, and direct method, where search uses a function likely to move in the direction related of the local gradient to find the local optima. The main disadvantage of calculus based methods is local scope. The optima they search are the best in the neighborhood of the current location, but they may not explore sufficiently; missing sharp events is probable. Based on the starting point, calculus based methods potentially miss the highest hill and focus on a local hill. In general, enumerative schemes evaluate every point in the space, one at a time, similarly to a brute force approach. This method is applicable when the search space is small, due to the lack of efficiency in large space problems. As researchers recognized the effectiveness of stochastic search over calculus-based and enumerative schemes, it became more popular. However, stochastic methods can also lack of efficiency in large space problems. Traditional schemes work well in narrow space problems, but not in broad spectrum problems.

Genetic algorithms are different in their way of solving a problem from traditional methods [139]. First, GAs do not work with the parameters themselves, but rather the coding of the parameter set. Second, the search is done from a population point of view, and not from a single point; multiple searches are performed in parallel. Third, GAs use an evaluation function in the form of payoff, considering the problem as a black box, and do not use derivatives or mathematical functions. Advantageously, they need make no assumptions of this sort. Fourth, GAs use probabilistic transition rules and not deterministic rules to direct the search. Considering the black box problem, GAs will select some inputs and acquire the evaluated output. New inputs will be based on the probability of having better performance from the previous runs' evaluations until a certain degree of satisfaction is achieved. Crossover allows useful combinations to generate better results based on the previous results. Therefore, genes from the above average ancestors will be used more frequently, similar to Darwin's evolution scheme.

The initial population is often generated randomly; each individual is generated with random genes. Often, the initial population is a combination of two initial populations after evaluating each individual; the best from both are combined into one population. Therefore, the initial population starts with better individuals, which can aid in the reduction of computation time. In some GAs, not all the individuals within the population are mated, only the more fit individuals are selected. There can also be different restrictions depending on the GA type and close "cousins", very similar individuals, are not allowed to mate. This is called incest prevention [147]. The individuals who mate produce offspring. These offspring may replace some or all of the population if they are more fit.

Each offspring is evaluated using a fitness function. It is very common to use fitness proportional reproduction, where each potential parent is compared to the population average, and this determines the expected number of offspring. The best individuals from the population are selected to continue into the next generation, whereas the others leave.

Given a problem with no prior knowledge, the landscape of all possible solutions may be defined as a finite space. Wolpert and Macready [138] showed that over the space of all possible search problems, all search algorithms have the same average performance. If algorithm A outperforms algorithm B on some set of problems, on all the other problems, the opposite will be true. In other words, there is no universally superior search algorithm.

In general, as the complexity level increases, a function's ability to provide a solution to a large problem decreases. Hill Climber (HC) functions are able to solve large problems where the complexity level is low and the landscape is defined with one high peak. At the other complexity end, Random Search (RS) and Exhaustive Enumeration (EE) are able to solve any complex problems, where the landscape is very complex with many peaks, but require small problem size. For intermediate levels of landscape complexity, algorithms like Iterated Hill Climbers (IHC), genetic algorithms (GA) and simulated annealing (SA) will each have a niche where they are able to solve the largest problems.

If the landscape complexity is unknown, the only way to understand its complexity is to perform exploration. For example, when one plays slot machines and wants to know which machines provides better outcomes; exploration is needed. Playing with each machine provides exploration of the landscape. With further exploration, patterns are recognized. One machine may provide better outcomes than others. One would like to have a strategy that exploits this emerging discovery. The optimal strategy for this, "k armed bandits' problem," is known to allocate trials to machines in exponential fashion, where the exponent is the estimate of each machine's payoff relative to the population average. As a result, some machines will be played more often than others. Furthermore, the process is adaptive: one big successful outcome from another machine may result in a shift the exploration pattern.

Much work has been done to develop superior algorithms, yet the no free lunch theorem states there is no superior algorithm for all problems. However, based on a specific problem, or class of problems, and known conditions a good algorithm can be developed and perform better than others. Previous work had produced an EC with strong properties for subset selection tasks of varying complexity [148] It used Eshelman's CHC algorithm [147]. CHC GA is non-traditional GA, where the offspring replace inferior parents (cross-generational rank selection). A superior individual (chromosome) can survive across generations. Different crossovers were investigated by Mathias et al. [148], and Schaffer et al. [149] to provide an effective subset selection GA, and they found genetic respect to be the most important characteristic. Respect means that genes that are common between parents should be passed on to the offspring [151].

This concept was tested to learn how much respect is sufficient to provide the balance between exploration and exploitation. The final crossover that is used by the algorithm is called the mix and match crossover (MMX) SubSet Selection (SSS), where the size of each chromosome plays a rule in the desired solution.

The initial CHC (Cross generation rank selection, Half uniform crossover, Cataclysmic mutation) population is generated randomly using a uniform distribution. In CHC, two initial populations are produced and the chromosomes are evaluated, and the more fit chromosomes from both populations are selected to become the next population. For all subsequent generations, the pairs of parents (randomly mated) produce two offspring and the selection operator produces the next parent generation by taking the best from the combined parents and offspring using simple deterministic ranking. Each parent chromosome has exactly one mating opportunity each generation, and the resulting offspring replace inferior parents. Mates are randomly selected, but limited due to an incest prevention operator applied before the offspring reproduction crossover operator. There is no mutation performed in the "inner loop." Only when it becomes clear that further crossovers are unlikely to advance the search, a soft restart is performed, using mutation to introduce substantial new diversity, but also retaining the best individual chromosome in the population. The responsibility for offspring production belongs to the crossover operator.

Crossover operator MMX is similar to RRR [147]. The basic MMX employs negative respect (i.e. no mutations). The MMX_SSS crossover operator consists of the MMX_0.85 crossover combined with a Subset Size (SSS) gene [148], which encodes the number of evaluated genes out of the total number of genes included in the chromosome. The parameter (0.85) in the operator name encodes the extent of negative respect (i.e. 15% mutations to the parental "unique" genes can occur).

SSS is a secondary mandate to the selection function. It is employed only if two chromosomes have the same value for classification accuracy (hierarchical selection with a two-dimensional fitness vector); then the smaller chromosome is ranked more fit. The offspring SSS gene is generated using Blend Crossover (BLX) [148, 151]. The SSS gene for each offspring is drawn uniformly randomly from an interval defined by the SSS genes in the parents and their fitness, the interval is first set to that bounded by the parental values, and then extended by in the direction of the more-fit parent.

See, e.g., U.S. Patent and U.S. Pat. Nos. 8,842,136, 8,849,575, 8,849,629, 8,855,980, 8,856,716, 8,862,627, 8,903,997, 8,913,839, 8,922,856, 8,923,981, 8,938,113, 8,945,875, 8,990,688, 8,995,074, 9,002,682, 9,009,670, 9,015,093, 9,015,145, 9,017,691, 9,022,564, 9,023,984, 9,029,413, 9,047,272, 9,047,353, 9,051,379, 9,053,416, 9,063,139, 9,121,801, 9,148,839, 9,164,481, 9,168,290, 9,171,250, 9,189,733, 9,193,442, 9,195,949, 9,213,990, 9,218,181, 9,223,569, 9,242,095, 9,256,701, 9,258,199, 9,259,579, 9,287,939, 9,289,471, 9,317,626, 9,317,740, 9,321,544, 9,323,890, 9,325,348, RE45660, 20160152438, 20160136431, 20160073313, 20160041174, 20160033622, 20160024156, 20150046181, 20150046216, 20150058061, 20150073495, 20150081077, 20150081324, 20150081911, 20150086087, 20150087589, 20150095146, 20150103681, 20150105086, 20150106310, 20150106311, 20150106314, 20150106315, 20150106316, 20150112403, 20150112636, 20150118158, 20150127066, 20150133306, 20150133307, 20150134315, 20150139977, 20150161629, 20150170052, 20150174408, 20150181822, 20150206214, 20150216426, 20150234976, 20150244946, 20150261926, 20150288573, 20150289210, 20150320316, 20150353880, 20150355459, 20150356350, 20150363108, 20150363193, 20150363194, 20150141863, 20150106069, 20150094012, 20150093037, 20150088024, 20150068069, 20150065835, 20150051083, 20150032015, 20150012256, 20140371834, 20140364721, 20140351188, 20140344013, 20140343396, 20140342703, 20140325019, 20140321756, 20140316221, 20140315576, 20140309959, 20140308930, 20140289172, 20140276191, 20140276121, 20140249429, 20140236530, 20140235965, 20140235201, 20140229409, 20140219566, 20140213909, 20140204700, 20140201126, 20140200575, 20140200572, 20140200571, 20140200471, 20140200430, 20140200429, 20140200428, 20140193087, 20140180049, 20140173452, 20140169686, 20140163425, 20140143251, 20140143064, 20140127672, 20140114165, 20140104059, 20140089241, 20140088415, 20140079297, 20140077946, 20140074564, 20140074180, 20140074179, 20140067485, 20140067484, 20140067470, 20140067463, 20140066738, 20140052379, 20140025304, 20140005743, 20130338530, 20130338496, 20130338468, 20130336594, 20130317392, 20130314694, 20130303941, 20130303119, 20130301889, 20130273968, 20130269376, 20130252604, 20130236067, 20130231574, 20130218156, 20130214943, 20130211291, 20130202177, 20130197380, 20130191090, 20130189977, 20130184603, 20130184553, 20130184538, 20130178730, 20130173194, 20130172691, 20130151447, 20130135008, 20130123684, 20130123666, 20130109995, 20130096394, 20130090266, 20130090265, 20130090247, 20130079002, 20130077891, 20130077843, 20130073981, 20130073490, 20130071837, 20130063613, 20130028052, 20130011062, 20130009783, 20120330170, 20120330109, 20120303560, 20120303504, 20120290505, 20120274937, 20120265350, 20120257046, 20120245481, 20120214510, 20120209798, 20120197831, 20120190404, 20120173154, 20120172746, 20120172743, 20120169053, 20120158633, 20120148157, 20120148149, 20120143382, 20120143078, 20120123232, 20120114249, 20120109653, 20120109612, 20120095352, 20120092157, 20120092156, 20120089046, 20120083246, 20120073825, 20120066259, 20120066217, 20120053441, 20120050750, 20120041608, 20120041330, 20120036016, 20120010867, 20120004854, 20120004564, 20110313285, 20110285982, 20110280447, 20110275364, 20110268328, 20110263958, 20110261178, 20110236922, 20110181422, 20110172930, 20110167110, 20110164783, 20110156896, 20110150253, 20110144519, 20110144065, 20110135166, 20110131162, 20110131041, 20110115624, 20110112426, 20110096144, 20110066404, 20110047105, 20110034967, 20110034824, 20110026832, 20110004513, 20110004415, 20100317420, 20100316283, 20100293115, 20100292968, 20100272340, 20100246544, 20100235285, 20100217145, 20100214545, 20100204540, 20100198098, 20100184702, 20100179400, 20100174271, 20100168836, 20100161654, 20100159945, 20100152905, 20100138026, 20100130189, 20100119128, 20100111396, 20100106458, 20100106269, 20100102825, 20100076642, 20100066540, 20100049369, 20100048242, 20100046842, 20100045465, 20100041365, 20100030485, 20100030484, 20100030038, 20100027892, 20100027846, 20100027845, 20100027469, 20100027431, 20100026799, 20100023307, 20100022855, 20100020961, 20100020208, 20100018718, 20100016687, 20100014718, 20100010681, 20100010503, 20100010488, 20100010368, 20100010355, 20100010332, 20100010331, 20100010324, 20090318779, 20090316988, 20090313041, 20090312819, 20090307164, 20090299162, 20090288152, 20090288140, 20090286512, 20090286509, 20090285166, 20090271342, 20090259537, 20090259534, 20090259533, 20090240366, 20090231173, 20090228408, 20090227876, 20090222108, 20090216133, 20090204341, 20090204029, 20090203981, 20090182287, 20090177420, 20090171740, 20090169075, 20090118637, 20090083010, 20090062684, 20090062635, 20090055147, 20090043542, 20090043541, 20090043525, 20090043182, 20090043181, 20090036758, 20090024549, 20090018891, 20090012766, 20080294019, 20080292146, 20080270328, 20080265130, 20080263323, 20080256069, 20080247598, 20080236275, 20080235165, 20080222734, 20080195261, 20080194996, 20080194946, 20080175480, 20080162487, 20080157510, 20080152217, 20080147441, 20080147440, 20080147438, 20080146334, 20080144944, 20080142713, 20080114564, 20080071136, 20080065291, 20080058668, 20080051660, 20080036580, 20080036187, 20080033316, 20080027841, 20080027769, 20080021342, 20080021336, 20080015871, 20080013747, 20080004904, 20080001735, 20070286336, 20070276279, 20070276270, 20070273504, 20070265808, 20070265806, 20070265533, 20070262574, 20070260656, 20070260427, 20070260425, 20070258329, 20070256432, 20070230795, 20070219749, 20070213786, 20070193811, 20070175998, 20070167846, 20070162992, 20070162189, 20070162084, 20070160973, 20070156317, 20070154099, 20070154079, 20070154078, 20070154063, 20070152433, 20070150021, 20070140551, 20070135964, 20070087756, 20070086624, 20070067003, 20070054347, 20070054266, 20070053513, 20070035114, 20070025597, 20070016476, 20060253781, 20060253258, 20060251293, 20060247536, 20060244246, 20060229822, 20060208169, 20060200260, 20060200259, 20060200258, 20060200253, 20060184473, 20060167784, 20060155398, 20060123363, 20060120584, 20060106797, 20060101017, 20060084115, 20060059028, 20060020597, 20060015497, 20060015496, 20060015495, 20060015494, 20060015492, 20050286179, 20050272110, 20050267911, 20050248136, 20050246314, 20050203434, 20050203360, 20050197590, 20050196047, 20050183958, 20050158736, 20050156775, 20050144284, 20050131660, 20050131607, 20050119454, 20050114078, 20050102246, 20050089923, 20050079524, 20050076190, 20050075846, 20050069162, 20050046584, 20050027457, 20050026199, 20050021101, 20050017488, 20050008179, 20040243567, 20040230131, 20040229210, 20040225649, 20040225629, 20040207548, 20040138578, 20040133355, 20040129471, 20040125148, 20040125133, 20040125121, 20040068199, 20040045030, 20040019470, 20030228565, 20030217047, 20030209893, 20030208451, 20030200189, 20030176656, 20030135109, 20030101164, 20030086593, 20030081836, 20030061228, 20030059837, 20030055799, 20030036835, 20020194159, 20020186875, 20020176624, 20020173936, 20020165854, 20020151992, 20020123975, 20020082756, 20020059022, 20020054694, 20020015532, 20020009756, 20010028743, U.S. Pat. Nos. 9,037,223, 9,033,893, 9,028,405, 9,019,819, 9,002,483, 8,996,442, 8,990,740, 8,976,856, 8,972,861, 8,965,044, 8,948,442, 8,942,180, 8,923,958, 8,918,169, 8,897,869, 8,897,586, 8,892,413, 8,886,301, 8,882,765, 8,880,158, 8,874,477, 8,874,203, 8,873,853, 8,873,813, 8,868,172, 8,866,936, 8,866,322, 8,861,799, 8,860,793, 8,855,775, 8,855,372, 8,855,011, 8,850,048, 8,849,737, 8,849,390, 8,838,510, 8,831,705, 8,826,199, 8,818,778, 8,818,404, 8,811,977, 8,810,796, 8,801,610, 8,797,550, 8,797,448, 8,792,974, 8,786,624, 8,781,597, 8,775,143, 8,775,134, 8,764,661, 8,764,651, 8,762,065, 8,761,903, 8,761,893, 8,761,051, 8,755,940, 8,755,916, 8,755,837, 8,750,971, 8,747,336, 8,747,315, 8,744,607, 8,744,557, 8,743,776, 8,725,667, 8,725,507, 8,725,243, 8,714,983, 8,713,025, 8,712,507, 8,702,629, 8,684,900, 8,680,991, 8,679,018, 8,678,943, 8,677,505, 8,659,697, 8,657,745, 8,649,565, 8,648,959, 8,645,832, 8,638,655, 8,635,051, 8,632,469, 8,626,274, 8,620,660, 8,611,692, 8,606,418, 8,606,021, 8,605,970, 8,600,830, 8,599,266, 8,595,164, 8,594,811, 8,588,933, 8,583,263, 8,582,916, 8,577,822, 8,577,451, 8,576,693, 8,560,134, 8,559,645, 8,547,824, 8,543,199, 8,536,133, 8,531,291, 8,527,324, 8,525,687, 8,525,673, RE44460, 8,522,312, 8,520,979, 8,516,266, 8,515,126, 8,503,791, 8,489,247, 8,488,863, 8,486,690, 8,478,394, 8,469,886, 8,467,884, 8,467,874, 8,467,611, 8,463,441, 8,461,988, 8,449,471, 8,437,998, 8,437,844, 8,437,223, 8,435,179, 8,435,167, 8,433,101, 8,428,925, 8,427,649, 8,416,710, 8,411,910, 8,406,867, 8,406,522, 8,406,115, 8,397,204, 8,396,582, 8,391,963, 8,388,604, 8,374,696, 8,374,667, 8,374,414, 8,369,967, 8,366,707, 8,364,136, 8,355,579, 8,351,321, 8,331,228, 8,323,188, 8,320,217, 8,315,150, 8,307,273, 8,305,436, 8,301,406, 8,295,934, 8,290,561, 8,282,549, 8,271,412, 8,265,725, 8,257,259, 8,253,824, 8,251,906, 8,244,475, 8,233,958, 8,226,561, 8,216,139, 8,213,399, 8,213,398, 8,209,745, 8,208,697, 8,204,697, 8,200,506, 8,199,632, 8,194,986, 8,194,938, 8,190,543, 8,190,194, 8,185,194, 8,183,062, 8,179,847, 8,174,956, 8,170,335, 8,170,334, 8,170,333, 8,165,916, 8,165,661, 8,164,345, 8,149,649, 8,126,664, 8,121,823, 8,121,046, 8,114,143, 8,108,036, 8,107,726, 8,103,333, 8,099,161, 8,098,938, 8,094,551, 8,089,853, 8,086,294, 8,086,017, 8,082,353, 8,082,032, 8,078,552, 8,078,274, 8,077,958, 8,068,894, 8,055,667, 8,046,107, 8,041,651, 8,041,124, 8,036,736, 8,036,442, 8,036,265, 8,032,477, 8,031,060, 8,023,710, 8,015,128, 8,005,631, 8,005,524, 7,996,762, 7,995,454, 7,987,003, 7,983,817, 7,983,141, 7,981,399, 7,974,714, 7,966,078, 7,957,265, 7,936,662, RE42236, 7,912,734, 7,912,138, 7,904,187, 7,903,617, 7,887,089, 7,881,181, 7,881,180, 7,872,985, 7,855,977, 7,831,358, 7,823,058, 7,819,003, 7,818,053, 7,813,822, RE41771, 7,805,386, 7,788,212, 7,777,743, 7,773,537, 7,769,513, 7,768,380, 7,756,060, 7,747,390, 7,747,325, 7,742,806, 7,733,224, 7,730,063, 7,716,148, 7,712,898, 7,710,828, 7,706,349, 7,702,555, 7,702,185, 7,697,792, 7,697,453, 7,693,683, 7,676,263, 7,676,062, 7,675,843, 7,672,219, 7,668,697, 7,663,502, 7,662,785, 7,660,437, 7,657,299, 7,655,895, 7,649,160, 7,636,700, 7,630,757, 7,624,076, 7,620,527, 7,606,790, 7,604,956, 7,599,759, 7,596,470, 7,596,242, 7,590,589, 7,590,510, 7,587,069, 7,584,075, 7,581,434, 7,575,171, 7,558,622, 7,539,533, 7,539,532, 7,536,064, 7,535,822, 7,533,006, 7,526,461, 7,519,476, 7,511,833, 7,502,677, 7,483,868, 7,477,758, 7,460,903, 7,454,244, 7,451,005, 7,430,483, 7,428,323, 7,426,499, 7,415,126, 7,409,303, 7,408,486, 7,407,029, 7,403,820, 7,401,807, 7,401,057, 7,395,250, 7,392,143, 7,385,300, 7,383,237, 7,379,568, 7,376,553, 7,366,719, 7,333,851, 7,324,851, 7,324,036, 7,310,522, 7,308,126, 7,295,608, 7,293,002, 7,286,964, 7,277,758, 7,270,733, 7,243,945, 7,242,984, 7,233,882, 7,231,254, 7,228,238, 7,209,787, 7,194,143, 7,190,149, 7,180,943, 7,164,117, 7,162,076, 7,149,320, 7,147,246, 7,085,401, 7,082,572, 7,051,017, 7,039,654, 7,028,015, 7,016,885, 7,007,035, 7,006,881, 7,003,403, 6,996,549, 6,988,093, 6,970,587, 6,886,008, 6,885,975, 6,882,992, 6,879,729, 6,865,492, 6,862,710, 6,850,252, 6,826,428, 6,826,300, 6,801,645, 6,789,054, 6,763,322, 6,763,128, 6,757,602, 6,757,415, 6,708,163, 6,697,661, 6,678,548, 6,675,164, 6,658,287, 6,650,779, 6,650,766, 6,640,145, 6,601,051, 6,560,542, 6,556,699, 6,549,804, 6,535,644, 6,529,809, 6,510,406, 6,459,973, 6,452,870, 6,445,988, 6,434,583, 6,400,996, 6,397,136, 6,389,157, 6,377,306, 6,363,350, 6,334,219, 6,272,479, 6,205,236, 6,167,155, 6,167,146, 6,154,705, 6,137,898, 6,128,346, 6,121,969, 6,115,488, 6,098,051, 6,091,841, 6,012,046, 5,995,868, 5,978,788, 5,963,929, 5,940,825, 5,847,952, 5,845,266, 5,815,608, 5,815,198, 5,745,382, 5,649,065, 5,602,964, each of which is expressly incorporated herein by reference in its entirety. These references disclose, for example, complementary technologies, aspects and details of implementation, applications, and the like.

SUMMARY OF THE INVENTION

The present technology provides a non-invasive and continuous system and method for monitoring of cardiac output from the human being. The technology is based on using high-sensitivity accelerometers to record chest wall motions. Specific filtering algorithms are utilized to identify both ventricular contraction time and stroke volume from such chest wall motions.

Advantageously, the system and method provide usable measurements of cardiac output for individuals who are upright, during locomotion. Therefore, the techniques are not limited to supine subjects or to subjects while holding their breath. Thus, this technology may find use in sports monitoring, and ambulatory patient monitoring. Further, the technology may be integrated within an implantable medical device (though likely requiring special calibration), and may be used to adjust a pacemaker, for example. In such a device, the cardiac output may be used as a feedback variable, permitting cardiac output to automatically respond to patient need.

In a sports medicine implementation, an athlete may be provided with real time feedback to optimize performance based on available blood flow, and perhaps predictive feedback during endurance sports to balance oxidative and glycolytic metabolism. The feedback may be presented through a watch display, audio feedback, or the like. After a sporting event or practice, the cardiac output measurements may be compared with athletic performance, to assist the athlete in achieving higher or better performance. The monitor can also be used for non competitive sports, and the cardiac output is measured to monitor health and optimize a workout. For impaired patients, the cardiac output monitor may be provided as an indicator to provide an assessment, and help determine an upper limit on physical exertion.

The technology can be implemented as a low power, portable or wearable, battery operated device. Numerous applications in wellness care, medical care, exercise monitoring, sleep monitoring, and sport science are proposed. The technology may also be applicable to veterinary science.

Different investigators have attempted to correlate specific chest acceleration signal components with the heart mechanical activity related to valves functions and volume movement. To date, all published studies have focused on analyzing the entire signal, that is, every detail of the recording throughout the cardiac cycle. Attempting to interpret all of the detailed information in a chest wall acceleration signal is problematic due to differences between subjects. However, the inward deviation of the chest wall associated with ventricular contraction which happens during the first heart sound is an aspect of the chest wall acceleration signal which is both uniform and consistent. A specific filter set was developed that is capable of providing an accurate estimate of stroke volume.

Hardware and signal processing techniques suitable for extracting both ventricular contraction timing and stroke volume estimation in the presence of breathing and when a person is moving (e.g. exercising) were developed. A 24-bit ADC is used to record chest acceleration where high amplitude impact noise does not saturate the input signal. Stroke volume and cardiac output estimates obtained using this new technology have been compared to simultaneous stroke volume and cardiac output measurements obtained with FDA approved electrical impedance technology (NICOM by Cheetah Medical) and a good correlation to this standard measurement technique, of approximately 90%, was demonstrated.

The principle challenges in achieving an accurate and reproducible estimate of stroke volume from chest wall motion is obtaining accurate timing of when the ventricle is contracting so that the signal analysis algorithm can be focused on only the relevant portion of the recorded signal, and removal of the extraneous noise generated through breathing, internal body organ movements, and whole body motion. The latter three tasks can be accomplished by appropriate filtering. Wavelet packet analysis is used for extracting information from noise in non-stationary time series data. A usual approach is to use Wavelet analysis to denoise the data and to separate observed components which subsequently allows decomposition, thresh holding, and reconstruction [176, 190, 191]. Moreover, in wavelet analysis, the mother wavelet is typically chosen based on the experience of the designer, and his sense of the ability of the mother wavelet to match certain features of the time series data stream. In some cases, just decomposition (without reconstruction) is performed to capture the magnitude of some specific feature of the signal [115].

Rather than a-priori selecting a mother wavelet for analyzing chest wall motion signals, multiple decompositions were performed based on a variety of different mother wavelets, producing an extremely large number of potential filter packets. A unique subset selection genetic algorithm (SSS-GA) was then used to isolate an optimal filter set that allows extraction of stroke volume output from acceleration recordings obtained from the chest wall during exercise using a relatively compact filter set. Previous investigations [147, 148, 149] demonstrated that a preferred strategy in this approach is to incorporate an index representation (genes are the indexes of the features to select from a possibly large pool of features), with a special subset selection crossover operator. This approach was utilized on the continuous acceleration signal to provide a continuous stroke volume assessment. Previously the SSS-GA algorithm was used with a classifier. However, the SSS-GA algorithm is now used to provide a continuous estimate. The evaluation function utilizes multiple linear regressions. The coefficient of determination is limited to two significant figures in order to provide sufficient quantization noise to promote algorithm convergence.

Four healthy men between 22-24 years in age were used as subjects. BMI ranged between 21 and 30 $Kg/m^2$, and heights ranged from 173 to 188 cm. One subject exercised regularly, while the others did not. Two subjects were Caucasian, two Asian. Cardiac output was recorded via electrical impedance spectroscopy (NICOM, Cheetah Medical, Inc.) using four electrode sets; two placed on the lower thorax and two on the upper thorax, and was set up to sample stroke volume, heart rate, and cardiac output every thirty seconds. Three ECG electrodes were used to obtain the second ECG lead, with electrodes placed on upper thorax on the right, and two on the lower thorax. Chest accelerations were recorded on the sternum above the xiphoid using a 2G accelerometer (Silicon Designs Model 1221), with analog filtering used to capture motion in the 8 Hz to 370 Hz to reduce high and low frequencies noises before digitalizing the input acceleration signal. A BioPack MP-150 data acquisition system was used to collect and digitalize (at 2000 Hz) the analog data. A twenty pole low pass digital filter at 50 Hz was used to isolate the frequencies between 8 Hz and 50 Hz to focus on the heart frequency spectrum and remove high frequency components. Following low pass filtering the data were decimated by factor of 20 to set the Nyquist frequency to 50 Hz.

Measurements were taken while subjects were at rest and during exercise. Data collection was started while the subject was at rest, in supine position, for 240 seconds, and then upright for 210 seconds. Five exercise sessions were started consisting of an exercise period for 150 seconds, pedaling at 100 cycles per minute, followed by a 270 second resting period.

A strap was wrapped around the subject with sufficient force (3N) to hold the accelerometer in place while exercising without creating difficulty to breathe. The NICOM provides thirty-second averages of stroke volume, and so wavelet decomposition was performed on each thirty seconds of recoded acceleration data. Eighty five 30s averaged measurements were taken sequentially using the NICOM, the ECG, and chest accelerations from each subject.

A filter set was identified using SSS-GA. Four mother wavelets were utilized in the design process, Daubechies (db); Symlets (sym); Coiflets (coif); BiorSplines (bior); ReverseBior (rbio).

Table 1 shows the best filter set identified to date for extracting stroke volume from chest wall acceleration data. This is a 28 filter set which utilizes packets arising from all four mother wavelets combined with Body Surface Area (BSA) of the subject, and a constant.

TABLE 1

Filter set solution to capture stroke volume which bicycling at upright position.

| Mother Wavelet | Packet | weight |
|---|---|---|
| bior5.5 | 5 | 156 |
| rbio3.3 | 7 | −376 |
| coif1 | 6 | −209 |
| rbio1.5 | 9 | −267 |
| sym8 | 10 | 476 |
| bior3.7 | 2 | −17.4 |
| sym2 | 3 | 128 |
| bior1.5 | 5 | 155 |
| rbio4.4 | 1 | 84 |
| rbio1.5 | 8 | −132 |
| sym7 | 4 | 98 |
| rbio1.3 | 5 | 309 |
| sym5 | 15 | 205 |
| bior3.9 | 9 | 298 |
| db7 | 3 | 73 |
| bior5.5 | 6 | −177 |
| rbio1.5 | 4 | −70 |
| db4 | 4 | −68 |
| bior1.3 | 10 | −385 |
| db9 | 1 | −70 |
| bior2.8 | 9 | 219 |
| db6 | 16 | −391 |
| coif5 | 3 | −65 |
| sym8 | 15 | −231 |
| sym7 | 16 | 154 |
| rbio2.4 | 9 | −296 |
| bior3.9 | 8 | 9.28 |
| db9 | 2 | 74 |
| BSA | | 4.15 |
| Constant | | −14.5 |

A multiple linear regression evaluation (using equation 1 (below) and table 2 parameters, where, W—weight, MW—mother wavelet, P—packet) was used to compare NICOM obtained stroke volume estimates to the chest wall based stroke volume estimates:

$$SV=4.15 \cdot BSA-14.5+W_1 \cdot MW_1(P_1)+W_2 \cdot MW_2(P_2)+ \ldots +W_i \cdot MW_i(P_i)$$

FIG. 15 illustrates stroke volume values obtained when this best filter set is applied to the recorded chest wall acceleration signals against NICOM estimates of stroke volume, where stroke volume estimates are averaged over thirty seconds to allow correlation to the NICOM data. An $R^2$ value of 0.89 for the four young adult men is obtained.

Accurate ventricular contraction times are critical to the performance of the above described algorithm. In initial algorithm development, ECG recordings were used to identify the point of ventricular contraction. In order to eliminate the need for the ECG, a procedure was developed to extract left ventricular contraction times directly from the acceleration signal.

Ventricular contraction timing is obtained using two algorithms, an adaptive heart rate detection algorithm, and a contraction location detection algorithm. Combined, these two algorithms provide a high correlation to the ventricular contraction time-point based on ECG recordings. In order to develop the adaptive algorithm pair, chest wall acceleration signals were concatenated from seven test subjects with different BSA and BMI. Focus is on contraction detection, since missing a heartbeat while calculating cardiac output is not permitted.

The heart rate detection algorithm isolates the first major acceleration deviation in the acceleration signal from the second major deviation (in terms of heart sounds, this is equivalent to finding the time point of the first heart sound without confusing with the second heart sound). In addition, this algorithm provides an estimate of subject heart rate (number of heartbeats per minute).

The ventricular contraction algorithm is based on a Continuous Wavelet Transform (CWT) approach, where the scaling of the mother wavelet is related to the measured hear heart rate. Filter shifting properties are used to isolate the first heart acceleration deviation (Contraction period). This algorithm provides a threshold window where only the positive data are analyzed and negative data rejected. Heart rate is measured by counting the number of threshold windows per minute, and is used to scale the CWT 'db5' mother wavelet accordingly every 60 seconds. The algorithm was tested on seven subjects between 22 and 60 years old, seated in an upright position, at rest, while breathing. The equation below is used to scale the CWT threshold function as a function of heart rate (HR). If the measured HR is greater than 240, CWT is set to be the maximum value the mother wavelet is scaled to 20, otherwise the scaling equation is used.

$$CWT_{scale} = \begin{cases} 20, & HR > 240 \\ \text{ceil}\left(\frac{2800}{HR^{0.89}}\right) & HR \leq 240 \end{cases}$$

The scaling algorithm proved to be able to adjust to a sudden new heart rate, as well as being able to adjust to different acceleration signals obtained from various subjects. FIG. 16 shows an example of the algorithm detection and adjustment phases. The algorithm detected (locked onto) the first subject's heart rate, then data from a second subject were introduced at a random point (~1.8×10⁴ data point), and the algorithm quickly adjusted to isolate the desired window, when the signal is above zero. After the algorithm has adjusted to the new subject's heart rate (~2.4×10⁴ at the bottom), the CWT transition is smoother and more definitive allowing better detection. FIG. 16 shows an example of automatic scaling adjustment based on the previous acceleration data that estimates subjects' heart rate. The arrow points on the adjustment time location.

Following the CWT Heart rate/window threshold algorithm, a second algorithm is used to detect the heart contraction deviation location using the defined CWT threshold windows.

Originally, the data were collected and analyzed first with the CWT threshold function and then with the second algorithm to find the best filter set for identifying the contraction time within the CWT threshold window. FIG. 17 shows typical acceleration data from a healthy individual, where the original acceleration signal at the top, the CWT in with the acceleration energy at the middle, and the isolation window at the bottom with the original sternum acceleration signal. The Y axis in each of the plots does not correspond to the actual acceleration or energy. The threshold function in the bottom plot accepts only the data in the positive window where the signal is equal to one and is rejected elsewhere.

The best mode algorithm performs both rate and location detection at the same time. The CWT threshold function is computed while the contraction time location algorithm detection is also computed. When a CWT window identifies a threshold time segment (i.e. change from 0 to 1 and from 1 to 0) a search for global energy maxima is performed on the combined filter set for contraction time location.

Two different algorithms have been defined; one has better sensitivity while the second has better positive predictive values. The first solution consists of two filters combined by element multiplication. This solution has sensitivity of 0.986 and positive predictive values of 0.987 and is composed of element multiplication of 'db8' at scaling of eight and 'Meyer' at a scaling of twelve. FIG. 17 shows an example applying this detection algorithm to one subject. The sternum acceleration signal is the top plot; the CWT db8 scaling 8 is the second plot; the CWT Meyer scaling 12 is the third plot; and, the absolute multiplication of both signals is shown in the fourth plot where the expected detection is equal to zero at the time of contraction and is based on the ECG signal.

The alternative solution consists of three filters and provides better positive predictive values (PPV=0.991) than the first solution. However, it has lower sensitivity (0.983). This solution consists of 'db13' at a scaling of eight, 'Meyer' at a scaling of twelve, and 'gaus2' at a scaling of 106.

The three algorithms can be combined to provide stroke volume, heart rate, and cardiac output assessment using one accelerometer placed on the sternum. They are combined in the following order since each algorithm depends on the output of the previous:

1. CWT Threshold—detects a window around the first acceleration deviation.
2. CTLD—finer detection of the contraction time detection based on CWT Threshold window
3. SV calculation using multi-regression line based on the filters energy values at the contraction time given by the CTLD output function.

The first algorithm provides an adaptive threshold window to isolate the heart contraction phase from relaxation phase. The second algorithm defines the contraction time location at the adaptive threshold window of the second algorithm. Heart rate calculation provides the scaling function of the second algorithm. The third algorithm is applied on a continuous signal, where SV is calculated using the defined contraction time to extract the combined energy from the filter set. All are combined as the "Infrasonic stroke volume". FIG. 18 shows the algorithm's function as a whole. The CWT threshold function defines general time segments to look for heart contractions. When the CWT threshold function defines a window the Contraction Time Location Detection (CTLD) algorithm output, consists of the two filters element multiplication, is pointing at the energy global maxima at the defined CWT TH window. The Stroke Volume (SV) algorithm performs regression (SVR) on all filters values at this time location, providing stroke volume measurement. Instantaneous Heart rate is calculated.

An objective of the present technology is to provide accurate and reproducible cardiac output monitoring in a small, battery operated (i.e. portable) device, specifically, a device that will allow long term cardiac monitoring. By identifying a small set of filters which provide high correlation to a "gold standard" CO measure, it is possible to utilize a microcontroller device with relatively low levels of computational power to achieve SV and CO outputs in the available time (i.e. between two adjacent heartbeats, e.g. less than 250 ms for a heart rate of 4 Hz, or 250 bpm). For example, the ARM cortex M0+ processor, operating with a 3V battery, can provide 0.9 Dhrystone Million Instructions Per-Second (DMIPS), allowing the complete algorithm to finish before new data point is presented.

Thus, the present technology estimates SV from a seismocardiogram recording, which is obtained by recording chest wall acceleration, preferably at the xiphoid process [109, 192]. This approach involves performing multi-wavelet decompositions on the acceleration data to generate a large pool of features from which a genetic algorithm (GA) is used to select the best packet combination for predicting SV. In a sitting position, a patient's back is not against a firm surface, similar to standing, resulting in different chest motions than in the supine position. Moreover, the organs of the body are shifted towards the abdomen, changing the orientation and fluid motion in the body. The patient chest vibration is preferably measured while patient breathes normally.

Cardiac output may be extracted from the displacement signal while patient is in a seated position. A twenty pole digital low pass filter was used to reduce frequencies greater than 50 Hz. It is possible to utilize a 3-D accelerometer to define the chest angles relative to gravity, and optimize the cardiac output algorithm based on the two angles. One accelerometer detects the sternum angle relative to gravity in one direction, forward and backwards. The second accelerometer detects the relative chest angle to the left and right side of the body. The genetic algorithm is used to define the best packet set for the different positions. An adaptive system based on subject position will provide the opportunity to wear this device and compute subject daily routine.

It is therefore an object to provide a method for computing cardiac output, comprising: measuring chest wall movements of a subject; performing a wavelet transform on the measured movements; determining, from the wavelet transformed measured movements, at least a cardiac stroke volume, based on calibration data derived from a plurality of subjects; and outputting information selectively dependent on the determined cardiac stroke volume.

It is also an object to provide a method for computing cardiac stoke volume, comprising: measuring chest wall movements of a subject; performing a wavelet transform on the measured movements; determining, from the wavelet transformed measured movements, at least a cardiac stroke volume, based on calibration data derived from a plurality of subjects; and outputting information selectively dependent on the determined cardiac stroke volume.

The movements are detected as vibrations comprising 2-50 Hz, and more preferably 5-25 Hz. The measured movements may be detected with a position detector (e.g., interferometer) or accelerometer, for example.

The method typically also determines a heart contraction timing, which may be dependent on the measured movements, an ECG, a microphone listening for heart sounds, a microwave sensor, an echocardiogram sensor, etc. The system preferably also measures a heart rate, and this permits calculation of cardiac output as the product of heart rate and stroke volume.

The wavelet transform may be based on one or more optimal mother wavelets and associated parameters, determined using a genetic algorithm. The genetic algorithm may also optimize a polynomial function to process the wavelet transformed information to determine stroke volume. The wavelet transform may be optimized based on both low computational complexity and correlation with a benchmark, i.e., stroke volume or cardiac output from a verified source. The wavelet transform may also be derived from at least one of an evolutionary algorithm and a genetic algorithm, which optimizes correlation with a benchmark and computational complexity to produce a set of optimum mother wavelets and weights. The method may further comprise employing at least one of an evolutionary algorithm and a genetic algorithm to define an optimal wavelet transform, which optimizes correlation with a benchmark and computational complexity. Both the stroke volume and heart contraction timing may be determined based on the wavelet transformed measured movements, and determining a cardiac output, wherein the wavelet transform is optimized based on both low computational complexity and correlation with a cardiac output benchmark for the plurality of subjects. The wavelet transform may be derived from at least one of an evolutionary algorithm and a genetic algorithm, which defines an optimum set of mother wavelets and weights. The optimum set of mother wavelets may comprise at least two different types of wavelets. The wavelet transform may comprise at least two different types of mother wavelets, in different decomposition paths. The wavelet transform may comprise a plurality of different mother wavelet types, in a plurality of decomposition paths, in a plurality of different filters at different frequencies.

The method may further comprise applying a plurality of different filters to the measured movements.

The movements may be measured on the sternum, and preferably the xiphoid process.

The method may calculate a non-normalized cardiac output value (e.g., a distorted cardiac output value that can be corrected based on subject parameters to yield a normalized cardiac output value). The non-normalized cardiac output value may be stored, communicated over a communication link, and normalized to produce a cardiac output value normalized for at least one body characteristic of the subject. The communication link may comprise Bluetooth.

The non-normalized cardiac output value may be communicated over the Bluetooth communication link to a smartphone, and the smartphone may normalize the non-normalized cardiac output value to produce the cardiac output value normalized for the at least one body characteristic of the subject.

The method may also determine a cardiac ejection fraction, a variability of a stroke volume, a variability of a cardiac output, or other parameters.

The method may employ a system comprising a housing 1 containing at least: a movement sensor, e.g., transducer 7; a microcontroller, e.g., automated processor 2; a memory 4; a power source, e.g. self-contained power source 5; and a communication port 3, wherein the measured movements are determined by the movement sensor, the stroke volume is determined by the microcontroller powered by the power source, stored in the memory, and communicated through the communication port. An acceleration sensor 6, discussed below, may also be provided in the housing 1. The housing may have a volume of less than about 4 cubic inches, e.g., <2" diameter and ¾" thick. The housing may be configured to be wearable by a human affixed to the sternum. The microcontroller may have an average power consumption while determining stroke volume on a beat-by-beat basis of less than about 300 mW, and be powered by a rechargeable battery. The battery may be, for example, a 2,400 mW-Hr battery to provide for 8 hours of continuous use.

Another object provides a system for computing cardiac output, comprising: a transducer configured to sense chest wall movements of a subject; at least one automated processor, configured to: perform a wavelet transform on the measured movements based on at least one predefined mother wavelet and at least one set of weights; and determine, from the wavelet transformed measured chest wall movements, at least a cardiac stroke volume, based on calibration data derived from a plurality of humans; and at least one of an output port and a memory, configured to receive information selectively dependent on the determined cardiac stroke volume. The system may further comprise a housing configured to be wearable by a human, containing at least: the transducer having an output corresponding to chest wall movement; a self-contained power source; and the at least one automated processor, comprising a microcontroller powered by the self-contained power source configured to process the transducer output on a beat-by-beat basis, to produce information adapted for estimating the cardiac stroke volume, to store the information in the memory, and to communicate the stored information through the communication port; wherein the communicated stored information is adapted to be processed by a remote system to calculate a cardiac output. An acceleration sensor may also be provided, configure to determine an acceleration vector of the housing, the acceleration sensor being distinct from the transducer, the microcontroller being further configured to determine an artifact condition based on the acceleration vector.

The method may further comprise measuring an acceleration vector of the housing through an accelerometer distinct from the movement sensor, and determining an artifact condition based on the measure acceleration. This is particularly helpful where the movement sensor for determining the stroke volume is readily saturated by significant body movements, and the subject is unconstrained and moving.

While it is preferred that the cardiac timing be determined from the same chest wall movements as are used to determine the stroke volume, the timing can also be determined using electrocardiogram input, phonocardiogram input, microwave, echocardiogram, or other types of sensors.

The method may further comprise receiving a height and a weight of the subject, and calculating a cardiac output based on at least the height, weight, stroke volume, and a heart rate.

The method may further comprise persistently storing in a memory a value calculated dependent on the stroke volume for each heartbeat.

The subject may be a human, mammal, or other animal. The chest wall movements of the subject may be measured during breathing and/or physical exertion. For quadrupeds, a distinct optimization would be required.

It is a further object to provide a system for computing cardiac output, comprising: a transducer configured to sense chest wall movements of a subject; an automated processor, configured to: perform a wavelet transform on the measured movements based on at least one predefined mother wavelet and at least one set of weights; and determine, from the wavelet transformed measured movements, at least a cardiac stroke volume, based on calibration data derived from a plurality of humans; and at least one of an output port and a memory, configured to receive information selectively dependent on the determined cardiac stroke volume. The automated processor may comprise a reduced instruction set computer (RISC) processor, e.g., an ARM processor.

It is a still further object to provide a method for analyzing a biological signal, comprising: receiving the biological signal as a series of digitized values representing a continuous process; performing a wavelet transform on the series of digitized values; calculating a polynomial function of the wavelet transformed series of digitized values; and outputting a calculation result of the polynomial function. The outputted calculation result may be determined substantially without inverting the wavelet transform. The wavelet transform may comprise a plurality of different wavelet waveforms and a plurality of different decomposition paths.

The wavelet transform and polynomial function may be together derived based on at least a genetic algorithm and at least one fitness criterion.

The continuous process may comprise, for example, electroencephalogram signals, or electromyogram signals.

A further object provides a method for analyzing a signal, comprising: receiving a series of digitized values representing a physical process; defining at least one fitness criterion for a wavelet transform on the series of digitized values comprising a convolution of a plurality of different mother wavelet waveforms in a plurality of different decomposition paths, the wavelet transform comprising a plurality of respective terms and at least one respective parameter applied to each respective term; optimizing the at least one respective parameter applied to each respective term of the wavelet transform, based on at least an iterative genetic algorithm and the defined at least one fitness criterion; and storing the optimized at least one respective parameter applied to each respective term of the wavelet transform. The plurality of respective terms of the wavelet transform and at least one respective parameter applied to each respective term may be together optimized based on the at least an iterative genetic algorithm and the at least one fitness criterion. The at least one respective parameter applied to each respective term of the wavelet transform may be calculated based on at least a correlation $R^2$ of the wavelet transform with a reference at a respective stage of the iterative genetic algorithm, and a precision of the correlation $R^2$ is sufficiently limited in order to increase a rate of convergence of the iterative genetic algorithm. The method may further comprise receiving a time-continuous biological signal; digitizing the biological signal to form the series of digitized values; and employing the stored optimized at least one respective parameter applied to each respective term of the wavelet transform to process the series of digitized values to determine a biological parameter, substantially without inverting the wavelet transform.

The biological signal may comprise at least one of an electroencephalogram signal, an electrocardiogram signal, an electromyogram signal, a phonocardiogram signal, a ballistocardiogram signal, an ultrasound signal, an x-ray signal, a magnetic resonance signal, a lung sound signal, and a bowel noise signal.

It is a still further object to provide a method for analyzing a signal, comprising: receiving a series of digitized values; performing a wavelet transform on the series of digitized values comprising a plurality of different wavelet waveforms and a plurality of different decomposition paths; calculating a polynomial function of the wavelet transformed series of digitized values; and outputting a calculation result of the polynomial function, wherein the wavelet transform and the polynomial function are together optimized based on at least a genetic algorithm and at least one fitness criterion.

BRIEF DESCRIPTION OF THE DRAWINGS

FIG. 1 shows the general approach of using multiple filter banks evaluated by a GA. The input signal is decomposed by multiple mother wavelets producing multiple filter banks, showing in different colors. A chromosome's genes specify a subset from those filter banks. Each subset is combined to give SV estimation and compared against a "gold standard."

FIG. 2 shows a general CHC flow chart, where survival of the fittest across generations is implemented.

DETAILED DESCRIPTION OF THE PREFERRED EMBODIMENTS

Figure 3:
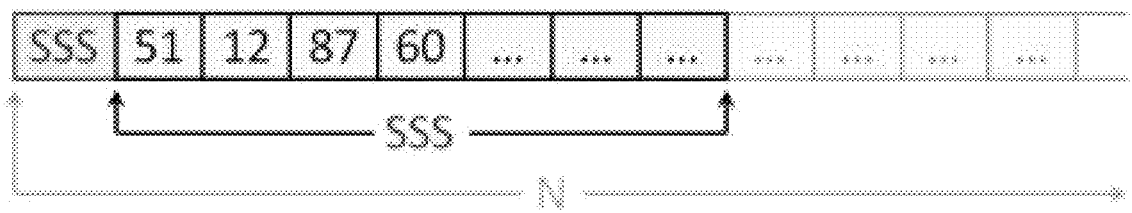
FIG. 3 shows a chromosome structure used by MMX_SSS, where the SSS gene dedicates the number of expressed genes within the chromosome and N is one plus the maximum SSS allowed in a gene.

The present technology provides a system and method for calculating cardiac output based on infrasonic chest wall movements, in an unconstrained subject. An accelerometer is provided to measure xiphoid process movements, which provide indication of both heart rate and stroke volume. While heart rate can also be obtained from other measures, the present technology permits (but does not mandate) use of a single transducer. The sensor data is processed by an algorithm that provides high correlation to standard measures of cardiac output, and has high self-consistency. To extract the two components of cardiac output, HR and SV, two different algorithms were developed. First, the HR algorithm was developed using a wavelet-based decomposition using a genetic algorithm to optimize the mother wavelet and associated parameters. The resulting algorithm determines both the heart rate and time of ventricular contraction (ejection). Second, the SV algorithm, synchronized by the HR algorithm, analyzes chest wall movement, e.g., velocity, to estimate the ejection volume. Together, these algorithms can execute on relatively low resource computational platform to provide stroke by stroke calculation of cardiac output in real time, i.e., the calculations are complete before the next heartbeat.

Cardiac Output is defined as the amount of blood the heart pumps per minute. At each heartbeat the heart contracts, the blood is pushed out from the left ventricle into the aorta. Due to this movement, chest volume is decreased, displacing the sternum to inwards. This displacement results in acceleration at the sternum. The accelerometer captures this acceleration, which is analyzed to calculate the chest displacement. In general, the displacement is equal to the double integral of acceleration.

This technology is applicable to medical, sports and fitness, and non-invasive monitoring environments. It is believed that the technology may also be used in veterinary environments, with the parameters of the algorithms recalculated depending on the species and other physical parameters.

The optimization of the parameters of the algorithms do not need to be replicated in the target monitoring device, but significant modifications of underlying presumptions would suggest reoptimization. Therefore, the target device need only receive the accelerometer or other infrasonic pickup device output, filter and preprocess the data, and execute the algorithm, which may be dependent on a subject's sex, body surface area, weight, or other readily ascertainable physical characteristics. While it is preferred that a single algorithm subject to these inputs be used, it is of course possible to provide a family of algorithms that are selected and employed dependent on the physical subject attributes and context. For example, the algorithm may differ for patients suffering from various heart diseases than for healthy subjects, e.g., mitral valve prolapse, where cardiac output as reflected in aortic flows may require correction of the stroke volume for reflux. Similarly, cardiomegaly may require use of corrections or a distinctly optimized algorithm.

It is also noted that, for any given subject, the target device may adaptively optimize its implementation to compute relative cardiac output, or a related measurement, though absent a calibration standard, absolute cardiac output calculation requires use of a verified algorithm.

A multiaxis accelerometer permits intrinsic determination of patient posture and physical activity, which can also be used as inputs to the algorithm.

The technology may also be integrated with other sensors, such as ECG, echocardiogram, microwave (radar) chest sensing, phonocardiogram, pulse oximeter, blood pressure, respiration sensor, peripheral vascular resistance (see Sharrock et al., U.S. Pat. Nos. 8,821,403; 7,727,157; 6,994,675), body fluid chemistry (e.g., saliva or sweat $CO_2$ and pH), and other non-invasive, minimally invasive or invasive measurements.

The technology may be implemented in a miniature form factor, and for example provide a module that adheres to the chest wall. The module may comprise the entire system, i.e., housing, sensor, analog signal processing (if employed), microprocessor, data memory, program memory, power supply, user interface, and data communications, or merely the housing, sensor, signal processing, and communications (e.g., Bluetooth), without execution of the algorithm. In the latter case, the cardiac output may be determined by an associated computing device, such as a smartphone, which receives the sensor data through the communication interface, and provides a platform for execution of the algorithm, user interface, and remote data interface.

The wavelet transform is a popular analysis tool for non-stationary data, but in many cases, the choice of the mother wavelet and basis set remains uncertain, particularly when dealing with physiological data. Furthermore, the possibility exists for combining information from numerous mother wavelets so as to exploit different features from the data. However, the combinatorics become daunting given the large number of basis sets that can be utilized. Recent work in evolutionary computation has produced a subset selection genetic algorithm specifically aimed at the discovery of small, high-performance, subsets from among a large pool of candidates.

This algorithm may be applied to the task of locating subsets of packets from multiple mother wavelet decompositions to estimate cardiac output from chest wall motions while avoiding the computational cost of full signal reconstruction. A continuous assessment metric can be extracted from the wavelet coefficients, but the technology preferably achieves a dual-nature objective of high accuracy with small feature sets, imposing a need to restrict the sensitivity of the continuous accuracy metric in order to achieve the small subset size desired.

Example 1

Transducer

Pilot studies were conducted using a standard MEMS accelerometer (Kistler Model 8312A). Different recording locations on the chest wall were investigated as well as the required filtering and equipment necessary to accurately and reproducibly extract CO measurements. Various analog filters, digital filters, and basic mathematical analysis approaches for removing noise and recording artifacts from the acceleration signal were also investigated. These initial studies relied on integrating the acceleration signal to obtain a displacement signal from which SV was determined. Polynomial curve fit baseline subtraction was the initial approach used to remove slow trends associated with integration and breathing. Wavelet analysis was used to remove noise from the recorded signal. First and second correlation to a NICOM Bio-impedance device showed good CO correlation.

The first recordings were undertaken in order to test the possibility of capturing a reproducible signal and provided cardiac information. Similar to previous studies reported in the literature, the initial recordings were performed with the subject supine (lying down on their back) and holding their breath for a period of 20 seconds. Three different recording locations were selected based on cardiac recording techniques utilized by others. These locations were assessed to minimize noise and other artifacts from the cardiac signal. The signal than was analyzed to extract cardiac information. Filtering and polynomial fit base subtraction were used to analyze the recorded data and provided repetitive waveform. Polynomial fit base subtraction provided consistent results to estimated CO from the recorded signal.

The recording location of any physiological signal is essential component in signal fidelity and reproducibility. Numerous considerations need to be taken into account when selecting the recording location. Muscle, fat, bones and cartilage and personal comfort are some of the components which effect the decision for recording location. Skeletal muscle vibrations in the range of 8-150 Hz are produced when contraction occurs and so can contribute to background noise in the infrasonic frequency range. Fat may contribute to low frequency vibration and also isolate or reduce specific frequencies. Bones and cartilage, in general, will transfer most acoustic energy since they are relatively solid matter, however they have a very different acoustic impedance than soft tissue, so will reflect a large portion of acoustic energy arising in soft tissue. With respect to pericardial motion recording, the skeletal system plays a critical role as the chest wall must flex in order to permit chest wall motion recording. A rigid rib cage will severely limit that motion of the chest wall. Comfort is also important to patients and as recording accuracy. If patients are not comfortable, the device may not be placed correctly or will shift from the original location over time.

Recordings were taken during breath holding and regular breathing using a 2G Kistler accelerometer, with pre-amplification (Model 5210). Initial recording showed that the sternum location provided the most consistent measurement sites since there is typically little muscle or fat at this location. This location is also easy to find and is symmetric compare to the other locations. The Apex location and its distance from the chest walls vary from one person to another, depends on subject physicality. In general, the apex is about 0.53±0.53 cm from the inner wall of chest, and 2.76±0.80 cm from the chest surface while subject is in supine position [127]. Moreover, females may have difficulty to place a transducer at the apex location. The upper chest location, between ribs two and three, slightly left from the sternum, has substantial underlying skeletal Pectoralis Major muscle, which can disturb the recorded signal if these muscles contract. Also, one person may place the transducer at slightly different locations than another, similar to what can occur at the apex location. Measurements were taken from one individual and were analyzed resulting in the selection of the lower sternum location above the xiphoid as the optimal recording location. The signal may be amplified digitally by a gain of 100 and sampled at 2,000 Hz.

The recorded signal demonstrates significant higher frequency components and has an offset due to the capture of the earth's gravitational field. Therefore, two filters were used as a band pass filter to capture frequencies between 0.05 to 150 Hz.

Heart Physiology

The ECG signal starts with the P wave deflection, result associated with both atria contracting, and correspondingly to an outward deflection of the chest wall, at maximum peak location. Ventricular contraction follows and is represented by the negative going curve (inward movement of the chest wall). SV is calculated using the slope connecting these two maxima. Isometric contraction occurs and provides constant blood pressure for a short period of time, directly correlated to systolic blood pressure. Following the ECG T wave, the ventricles relaxes and eccentric contraction occurs. The ventricles start to refill while the blood moves from the aorta out to the rest of the body. The displacement signal does not fully agree with the seismocardiogramy signal. For example, the acceleration signal shows MC—mitral valve close and AO—Aorta valve open deflections. The displacement signal does not show those events since the heart muscle is in isometric contraction during this period, resulting in blood pressure increase. Therefore, there is not much displacement and the acceleration is close to zero.

When the subject is breathing, the velocity signal contains distinct sinusoidal variation due to motion of the chest wall resulting from inhalation and exhalation. A polynomial cure fit was used to remove this low frequency noise. The integrated acceleration, which is the velocity signal in blue, has tenth order polynomial curve fit base subtraction.

Algorithmic Development

Detrending was employed to remove the lower frequency components of the signal. Specifically, a $10^{th}$ order polynomial curve fit was incorporated after the first integration as a means to reestablish a flat baseline for the chest velocity signal. The velocity was then calculated. Even though the subject, in this case, holds his/her breathe the chest still moves slowly and can be seen to have substantial low frequency components. The corrected velocity is used to identify heartbeat time duration using the negative amplitude deviation segments. These negative peaks can be used to define a windows segment to be analyzed. Similarly, a correction using polynomial curve fitting is done to the displacement of the signal after the velocity is integrated. The polynomial function was derived as a least squares regression fitting to the velocity signal.

Three heartbeats were taken as the window of integration, using the velocity signal for the entire analyzed duration. The number of analyzed windows therefore equals the number of recorded heartbeats minus two. The interval of a window has a correction based on a ninth order polynomial curve fit and is performed on the velocity signal and on the displacement signal. Therefore, each heartbeat has a third order curve fit as a correction factor. The second heartbeat, which is in the middle of the window, is analyzed and provides the displacement of the chest wall.

The acceleration signal is integrated and provides the velocity signal.

In this case the analyzed data consists of seven seconds of recordings while the subject holds their breath. There are six heartbeats generating four displacement signals. The maximum displacement variation is associated with the chest volume change, which is directly related to the heart Stroke Volume (SV). The SV is related to the Ejection Time (ET) which is about 300 milliseconds from the first positive displacement peak to the second positive displacement peak (0.38-0.65 s). The Heart Rate (HR) is calculated using the time difference from one heart contraction to another. Therefore, the CO can be found by the multiplication of the average SV by HR.

The displacement signal at the upper chest wall varies much more than the displacement signal at the apex location and the displacement signal at the sternum location, and a peak velocity was not calculated by the program. Therefore, those values were chosen manually to calculate each displacement signal.

Even a very sharp filter cannot effectively remove the noise artifacts at low frequencies. Therefore, a polynomial curve fit based subtraction was employed to analyze a small window of three heartbeats, which is used after the first integration to provide the chest velocity. Another polynomial curve fit based subtraction was then applied at the second integration to provide the chest displacement. The average of the middle displacement of all windows provides reasonably reproducible information of the stroke volume and corresponding CO. In particular, the sternum location found to be better location to record the signal perhaps due to chest symmetry and the lack of fat and muscle at this area. Importantly, this location can be found more easily than the other two locations. Literature on the Kinetocardiogram indicates that the sternum location moves symmetrically inward which also justifies the sternum location [105]. The large and symmetric motion at this site has been explained by three factors: 1) the intrathoracic pressure change associated with ejection of blood; 2) a shift of blood from the lower to the upper chest; and 3) heart movement, pulling inward the anterior surface of the chest [105].

The mechanical activity of the heart is related to the electrical activity of the heart muscle, through a process referred to as excitation-contraction coupling. Correspondingly, the ECG can be used to provide a time marker to identify when the left ventricle is about to contract. To observe the heart's electrical activity, a pair of ECG electrodes may be used, which provide the second ECG vector, that is, in a direction from the right arm to the left leg. This vector direction reflects the hearts electrical activity from the sinus node to the apex, which is the natural pattern of the heart's electrical current flow. The heart's electrical activity shows six deflections. The P wave is associated with atrial contraction. The Q, R, S segment is associated with ventricular contraction. The T wave is associated with the heart's relaxation phase. The U wave is not common and associated with heart disease. Knowing these deflections, allows temporal alignment with the chest mechanical recordings and interpret identify the hearts activity.

Simultaneous recordings of the heart ECG and chest acceleration were taken to observe the relationship between the heart mechanical activity and its electrical activity while the subject was breathe holding. Three ECG electrodes were used to record the ECG lead two. The first electrode is placed on the right shoulder and the second is placed on the left side of the stomach below the left ribs. The third electrode is placed on the right side of the stomach below the ribs and is used as a reference potential. The Kistler accelerometer was placed on the sternum. Two filters were connected to the acceleration transducer. The first one was a high pass filter at 0.05 Hertz and the second a low pass filter set at 100 Hertz, to minimize noise and other recording artifacts. The accelerometer output was amplified by a gain of 100 before digitizing at a sampling rate of 2000 Hz. The recordings were taken with the subject in supine position. Duplicate recordings were taken. The first recording was taken with the subject's holding their breath, and the second was with normal breathing. It is known that the electrical activity of the heart occurs before the mechanical activity. Specifically, the QRS complex occurs immediately before the start of ventricular contraction, and correspondingly, the magnitude of the acceleration increases rapidly. Following the T wave of the ECG there is a period of high frequency vibration, which indicates the second heart sound and the beginning of the heart's relaxation phase.

The average displacement signal was computed and seen to be slightly different than the breath-holding displacement signal. In general, there is a greater chest displacement during cardiac contraction when the subject does not hold their breath.

Further analysis was done to correlate the displacement amplitude to breathing pattern. The velocity signal was used to distinguish the initial inhale and exhale periods. The breathing pattern is clearly seen in the velocity signal. However, it is hard to distinguish the pattern using the acceleration signal. This signal provides the inhale and exhale breathing periods, with the minimum velocity points identifying the beginning of the inhalation period. The maximum velocity points are considered to be at the beginning of the exhale period. These periods were identified and analyzed separately. The acceleration signal was integrated and filtered using high order digital high pass filter to reduce the breathing pattern. High order polynomial curve fit requires high computation power, and therefore it is not used in resource-constrained applications.

The average chest displacement due to heart contraction at the beginning of exhalation was found to be about 200 microns resulting in chest compression inward. During expiration, respiratory loading caused an increase in stroke volume. During exhalation, the intrathoracic pressure increases, resulting in decreased venous return, and therefore atrial filling, resulting in a decrease in stroke volume at the end of exhalation and beginning of inhalation; corresponding increase in heart rate. During inhalation, intrathoracic pressure decreases, enhancing venous return and therefore stroke volume, resulting in a decrease in heart rate decreasing during inhalation [127, 129, 130].

The average chest displacement signal measured at the beginning of inhalation in this sample is about 150 microns. As stroke volume normally increases during inhalation, this sample may be too early in the respiratory cycle to show the benefit of increased venous return.

Simultaneous recordings of ECG and acceleration signals provided a general interpretation of the displacement signal.

Seismocardiograpy interpretation provided some information about the displacement signal but was not totally consistent with previous observations. Long duration recordings of chest acceleration allowed observation of cardiac differences between the inhale and exhale periods of breathing. The chest displacement signal was found to be different when subjects held their breath and when the subjects breathed regularly. In general, during an inhalation, chest displacement due to ventricular contraction is greater reflecting a greater heart stroke volume consistent with increased venous return associated with inhalation.

Example 2

In the next stage of testing, a new, lower noise, and more sensitive, accelerometer was used to record the acceleration signal. The accelerometer 1221 from Silicon Design was used which provided greater sensitivity (2000 mV/g) and lower noise (5 μg/Hz$^{1/2}$). The displacement signal, correspondingly, was observed to have a slightly different pattern than the previous recorded signal. In addition, wavelet analysis techniques were employed to remove the high and low frequencies components of the chest acceleration signal, and provide better artifact removal. The new transducer included amplification along with low pass and high pass filters. The high pass filter was set at 8 Hz and the low pass filter at 370 Hz. The recordings were performed similarly to the previous recordings. The displacement signal is slightly different, since the low frequency components below 8 Hz, which were captured in the previous recordings, have relatively large amplitudes. These low frequency components are reduced significantly with the 8 Hz high pass and so do not affect the signal as much as the previous recordings. In this case, all the signals are decimated to be the same length, and permitting better averaging. The average displacement is about 150 microns.

When a subject speaks, coughs, or vocalizes in any way, the chest vibrations overlap in the recorded frequency spectrum. Therefore, a low pass filter, as previously described, is applied at 50 Hz to minimize the influence of these artifacts. The significance of the filter is shown by looking on the Discrete Fourier Transform (DFT) of a typical acceleration signal before and after the filter. The sampling frequency at this point is 2 KHz, and is decimated by a factor of ten. In general, when speaking, women generate higher frequencies at a lower magnitude than men. This has an effect on the analyzed frequency spectrum. Therefore, the present example focuses on men. It is understood that an adaptive filter can assist in removing voice sounds and environmental vibrations and sounds from the spectrum to be analyzed. The frequencies over 50 Hz have higher magnitude during speaking. In men, frequencies in the 90-100 Hz range have high magnitude. The observed heart frequencies are primarily at 0.5-50 Hz. The frequency spectrum of a typical woman while speaking shows frequencies both lower and higher than 50 Hz have lower magnitudes than the observed in the frequency spectra of men. A twenty pole digital low pass filter at 50 Hz lowers the magnitude of frequencies associated with speech. The average displacement signal shows good correlation. However, not all the displacement signals align, but for the most part they do. Fast breathing or panting produces low frequency noises, and can be reduced by using high order high pass filter at 2 Hz.

The transducer provides three filters; the first filter is a three pole high pass filter at 8 Hertz; the second filter is a three pole low pass filter at 370 Hertz; and the last filter is a one pole high pass filter at 1.5 Hertz. The total gain of this system is about 400.

Because of the high pass filter, this transducer is only weakly sensitive to frequencies between 1 and 8 Hz. The observed cardiac frequency is generally considered to cover the 1-50 Hz range. Therefore, the input transducer may not contain all desired information. The transducer's transfer function is flat in range of 10 Hertz to 200 Hertz. The signal is sampled at frequency $f_s$ at 2000 Hertz, and decimated by a factor of ten, $f_d$ at 200 Hertz, before the wavelet analysis is done. Theoretically, the high pass filter should be at 2 Hz to reduce breathing and other low frequency noises, while the low pass filter should be at 50 Hz to reduce speaking and other high frequency noises.

Polynomial cure fit baselines subtraction demands substantial computational power. Therefore, more efficient and accurate methods were sought. Wavelet decomposition of the signal provides the capability to distinguish between different frequencies sets and reconstruct the filtered signal.

The analysis in this case utilized four steps. The first step was decimating the signal by a factor of ten. Therefore, the analyzed Nyquist frequency the original sampling frequency of 2000 Hertz became 100 Hertz. The second step was signal decomposition, where six levels of decomposition was performed using Matlab wavelet toolbox. It was found that the sixth level of decomposition using Shannon entropy as the cost function was most efficient. A wavelet program was written to have complete control on the processed signal and was used in the analysis. The third step was to reconstruct an output signal with selected packets base on the desired energy spectrum. The last step is to integrate the signal twice and acquire the displacement signal. Another analysis was done by preforming the double integration first and then performing wavelet analysis on the displacement signal.

Since the custom transducer had a high pass filter at 8 Hz, the velocity signal is centered at an equilibrium point after the first integration. The displacement signal, however, still has significant low frequency components. The acceleration signal is reconstructed from a fifth decomposition level using packets set of 2 to 28, where a sixth order Daubechies has been used as the mother wavelet. The double integration provides the reconstructed displacement signal, which is centered at zero. The low frequency component of the signal is reduced. Therefore, the ability of wavelet analysis to process the signal was found to be effective. Further analysis is needed to "polish" the displacement signal.

The displacement due to ventricular contraction is measured from the maximum peak around 0.28 seconds to the minimum peak around 0.32 seconds. All seven contractions contribute to the average chest displacement. The average does not represent the true average of all displacements. Therefore, the chest displacement of each heartbeat is calculated and averaged. Better results are achieved when the wavelet analysis is done on the true displacement signal, taking the double integration on the acceleration signal first and then computing the wavelet transform.

Clinical Testing

Ten subjects were selected for comparison recordings. The recordings were taken while the subjects were in the supine position and breathing normally for thirty seconds as well as during a short conversation of thirty seconds. This process was also completed while the subjects were in a seated position and a standing position. Wavelet analysis was performed on the displacement signal for each recording and compared. Most of the subjects were in their twenties, and two subjects were women. The average displacement of each subject is compared. Six decomposition levels are used and packets 2-28 were reconstructed to reduce the low and high frequency noises. Frequencies between 50 Hz and 100 Hz where not reconstructed in this example since there is no significant frequency content in the displacement signal in this range, and the literature also justifies using frequencies below fifty Hertz.

Since the raw signals are noisy, the algorithm uses the velocity signal as the marking point to find the ventricular contraction peaks. However, these peaks are not consistently detected.

There is an inverse relationship between chest displacement and BMI. As subject BMI is higher the chest displacement is lower. Assuming high BMI related to greater chest circumference, the total chest volume is greater; the chest displacement due to blood flow is smaller. As shows the $R^2$ value is low, but the representative trend-line has percentage coefficient of variation of 26.6 from the base line. One subject was removed from this analysis since all other subjects were in their twenties. Better correlation is achieved when the chest volume and heart rate are factored into the regression analysis. The standard deviation percentage from the base line is better and the $R^2$ value is higher at 0.46. Additional demographic parameters (age, gender, etc.) would need to be taken into account to provide an accurate estimate of cardiac output; nonetheless, this result shows the ability to use the measurements to assess cardiac activity. Moreover, some of the subjects needed to adjust the transducer on their chest to create more pressure between the transducer and their chest, adding errors to the recordings.

It is typically necessary to compare new measurement techniques to the existing technique to illustrate correlation between the two to provide proof of concept. If there exists a "gold standard" measurement, then comparison to the 'gold standard" is essential. In the case of cardiac output assessment there is no existing gold standard. Invasive catheter based measurements are commonly used in the hospital setting as a central line has often been placed into a patient for some alternative purpose, but this approach is widely viewed as inaccurate, and moreover, preforming invasive cardiac output measurements is not possible in a non-hospital setting. Therefore, non-invasive cardiac output monitoring (NICOM) equipment was used to provide cardiac output measurements. It is important to perform simultaneous recordings while comparing the measurements to show a "standard" measurement. Specifically, a bioelectroimpedance based technique developed by Cheetah Medical of Israel was elected, which had recently received FDA approval.

Largely as a result of NASA funded research, bioelectrical impedance techniques for estimating cardiac output have been shown to be an effective alternative to ultrasonic or invasive measurement approaches to obtain CO. Correspondingly, over the last decade, several companies have begun to offer commercial CO monitoring devices based on bioelectroimpedance. Specifically, Cheetah Medical has developed bio-impedance system (NICOM) which they refer to as a bio-reactance device. This device has obtained some acceptance in the hospital environment and provides continuous non-invasive cardiac output monitoring for several hours, or until the electrodes become detached from the skin. Importantly, this equipment does not require a physician or other clinician as an operator, significantly lowering operating costs. Standard bio-impedance systems rely on a standard four-electrode current source recording arrangement. They apply a high-frequency constant amplitude electrical current across the thorax using two electrodes, and record the corresponding voltage difference between the remaining two high input impedance electrodes. The ratio between the measured voltage and applied current amplitudes is a measure of transthoracic impedance. This instantaneous impedance change is related to the stoke volume (SV) change, and is proportional to the product of peak flow and ventricle ejection time (VET). SV is proportional to the product of maximum impedance change and to the phase shift change.

The correlation between chest motion due to heart contraction to cardiac output was determined. The first verification was performed between the reconstructed infrasonic displacement signal and the NICOM measurements of cardiac output. NICOM, ECG and Infrasonic measurements were taken simultaneously while the subject was in supine position; seated at an angle of 30°, supine with legs are at 30° from the horizontal line parallel to the ground, and after a short exercise. The average of the sternum displacement, has been compared to NICOM cardiac output measurements. The sternum displacement was measured at the two hundred milliseconds time point following the ECG QRS complex, calculated from the reconstructed infrasonic displacement signal. In this case, a 10s average sternum displacement obtained from a one minute NICOM cardiac output recording is compared.

The chest acceleration signal is recorded simultaneously with the ECG signal and is integrated twice. Wavelet transform is performed on the displacement signal, where the original signal is decomposed and specific packets are selected for reconstruction. The reconstructed signal is then aligned with the ECG signal. The inward movement of the chest is captured by the reconstructed displacement signal.

Correlation analysis was performed using the average chest volume change due to heart contraction over one minute interval. The cardiac output is the product of the average volume change per minute and heart rate obtained from the Infrasonic cardiac output.

A correlation of $R^2$=0.72 was achieved by computing five wavelet decomposition levels using $6^{th}$ order Daubechies as the filter coefficients. At the fifth decomposition level, packets two to twenty eight were selected for reconstruction. Shannon entropy indicated that the most signal information is within the first packet, which contains the lowest frequency components, but these are below the heart's frequency spectrum. Therefore, Shannon entropy does not provide a good indication for selecting packets for reconstruction. Packets with the most heart information are between one to fifty hertz and so were selected for reconstruction. Another aspect for reducing computational time and increasing cardiac output correlation, is by computing more decomposition levels. By computing more decomposition levels finer frequency segments and select a better packet set is achieved. However, computational time increases as decomposition level increases. The $R^2$ value does not change much between fifth and eighth decomposition levels, where all the packets were selected for reconstruction except the first packet; lower frequency range, and the last four packets, high frequency range.

Choosing a different Mother wavelet may also increase cardiac output correlation and decrease computation time for lower order filters. Each filter has double its coefficient based on its order. For example; Daubechies one, which also known as the Haar wavelet, has two filter coefficients; Daubechies two has four filter coefficients; Daubechies three has six filter coefficient and so on. From Daubechies two to Daubechies ten the correlation to NICOM cardiac output is about the same. Daubechies two is computed the fastest, but in general the size of the filter does not greatly affect the computation time nor provide better results.

There are many possibilities to perform different filters at different decomposition levels and choose different packet sets to achieve faster computation and obtain better cardiac output correlation. The possibility of using one or more packets to correlate to cardiac output is also an option which should be investigated. Since there are so many potential wavelet packet possibilities, Genetic Algorithm strategies were applied to define the best packet set or CO prediction.

Since one measurement does not provide a reliable cardiac output correlation, further investigation was done on multiple subjects. Measurements from four subjects were taken simultaneously using the NICOM, ECG, and chest acceleration. Subjects were asked to be in supine position for seven minutes until NICOM calibrated and performed sufficient CO measurements to start the experiment. Subjects were moved to a sitting position, and then began to exercise for 35 minutes, involving cycling for two minutes and resting for five minutes.

Previously the ECG algorithm was able to detect the contraction time (QRS complex) when the ECG signal was stable, but did a poor job when signal was not stable; i.e. when the subject was exercising. The algorithm was modified to have better QRS detection using a wavelet transform. Similarly to the acceleration signal, the ECG signal suffers from low and high frequency noises. A similar approach was used to remove the noise from the ECG signal, providing a correlation of $R^2=0.99$. Good CO correlation of $R^2=0.84$ was found, but a closer look at SV and HR indicates deficiency in SV correlation.

The transducer captured the acceleration signal from the sternum. This signal is filtered using a low pass filter at 50 Hz to remove high frequency noises, since the heart motions are largely below this frequency. The signal was decimated by a factor of ten originally, and during NICOM measurements was decimated by a factor of twenty. The acceleration signal can be converted to a displacement signal before or after the wavelet analysis. When NICOM measurements were taken, the acceleration signal was converted to displacement before computing the wavelet analysis. The number of decomposition levels and the wavelet filters are set before computing the decomposition. The packet selection is done on the last decomposition level. The displacements of the heart contractions are captured from the reconstructed displacement signal and averaged over a period of one minute. Cardiac output is calculated and compared to NICOM recordings. Use of a Genetic Algorithm may provide better correlation to NICOM by selecting different packet set.

The initial recordings utilized an off the shelf Kistler accelerometer to measure chest displacement during heart contraction. The literature on kineto-cardiograms justified the sternum recording location by showing symmetrical inward motion [105]. Moreover, this location is justified due to its physical structure; the accelerometer can be placed on the sternum where there is little muscle or fat and is found easily. The recordings at this location were found to be consistent when using a polynomial curve fit baseline subtraction and integrating the result to find the displacement of the sternum. This analysis was performed on both the velocity signal after integrating the acceleration signal and the displacement signal after integrating the velocity signal.

Simultaneous ECG recordings confirmed the initial proposal that the main negative deviation of the displacement signal is due to ventricular contraction. The simultaneous recordings also allowed us to identify the infrasonic cardiac output deviation and distinguish inhaling cardiac function from exhaling cardiac function. Chest displacement during inhaling is found to be greater than inhaling and is consisted with literature [129, 130]. Polynomial curve fit base subtraction provided good filtering tool, but requires significant computation power. Therefore, wavelet transform analysis is more suitable.

A custom made transducer was developed to improve chest infrasonic acceleration recordings due to heart contraction. This transducer provided lower noise measurements with higher sensitivity. Wavelet transformation was able to eliminate noises from the recorded signal. The analysis was performed on ten heart beats on ten subjects and observed that the variance on the ten displacement signals was about 30%, but better correlation was achieved when BMI and other physical differences were incorporated into the analysis; specifically, a 25% variance was obtained when factoring in Heart Rate, Chest volume and BMI. Better results can be obtained when more components are factored in and better signal analysis is performed.

Finally, a comparison between the infrasonic measurements and an approved non-invasive Cardiac Output monitoring were undertaken. Comparison to the NICOM demonstrated good correlation, $R^2$ value of 0.72.

Example 3

Genetic Algorithm Optimization of Wavelet Packet Set

In the past, wavelet transform and GAs where combined yield results for the problem set they were used. In this case, non-traditional wavelet computation is employed, where just decomposition is performed and a GA is used to define a specific packet set which correlated best to the ground truth. An initial method did not work and further investigation was done to modify the algorithm to identify a desirable solution. A series of experiments was used to test the algorithm, and after restricting the correlation value $R^2$, the algorithm was able to converge. The final algorithm was used to identify specific features that correlate best to NICOM SV giving four subjects data.

In this application, a subcomponent of chest wall motion (seismocardiogram recording) is sought to be discovered which can be used to estimate a specific activity of the cardiac muscle, for example, stroke volume. The time consuming operation of waveform reconstruction is sought to be avoided, since the application calls for rapid response from a resource limited device. Moreover, there is a potential to investigate for better correlation.

SV is estimated from chest acceleration, at the xiphoid process [108, 111]. The approach involves performing multi-wavelet decompositions on the acceleration data to generate a large pool of features from which the GA is used to select the best packet combination for predicting SV. The "ground truth" SV is obtained using electrical impedance based Cardiac Output Monitoring device NICOM.

Eshelman's CHC GA [147] search engine combined with the MMX crossover operator [148] identifies the best subset genes (i.e. packets), from a multiple filter bank. Since the goal was to minimize the number of genes to avoid over fitting and to reduce the computational costs of SV estimation, a Sub-Set-Size (SSS) variable was defined [149] and added to the chromosome. FIG. 2 shows the general CHC pseudo code. The initial population consists of random chromosomes, with each chromosome consisting of a variable number of genes, which are evaluated using a fitness function. CHC's selection process, called cross-generational rank selection, differs from many conventional GAs. Each parent chromosome has exactly one mating opportunity each generation, and the resulting offspring replace inferior parents. Mates are randomly selected, but limited due to an incest prevention operator applied before the offspring reproduction crossover operator. There is no mutation performed in the "inner loop."

Only when it becomes clear that further crossovers are unlikely to advance the search, a soft restart is performed, using mutation to introduce substantial new diversity, but also retaining the best individual chromosome in the population.

The initial GA population is generated randomly using a uniform distribution. In CHC two initial populations are produced and the chromosomes are evaluated, and the more fit chromosomes from both populations are selected to become the next population. For all subsequent generations, the pairs of parents (randomly mated) produce two offspring and the selection operator produces the next parent generation by taking the best from the combined parents and offspring using simple deterministic ranking.

Understanding the chromosome structure provides an understanding of the connection between the feature-genes and the Sub-Set-Size (SSS) gene. A chromosome is defined as set of genes, and in this approach, the first gene represents the SSS, that is, the number of genes that are expressed when a chromosome is evaluated (FIG. 3). The SSS gene takes on values between one and the maximum number of genes allowed; it tells the evaluation routine how many of the subsequent genes are to be used in computing the fitness. The remaining genes represent inheritance from a previous generation and may be passed on to future generations, but they do not contribute to the fitness of the chromosome. It is possible that the offspring will express some of the parental "unexpressed" genes because their locations and the SSS will change. This chromosome format was designed by Schaffer et al. [149] and is used by the MMX_SSS crossover operator.

The expressed genes in a chromosome represent the magnitudes of a subset of wavelet packets. The mathematics of the wavelet transform may be found elsewhere [125, 126, 127]; here discreet wavelet transforms (DWT) are used. In wavelet transform analysis, the focus is often the low frequency components. The time sequence is separated into two components: low frequency components, called approximations, and high frequency components, called details. Subsequent levels of decomposition are performed on the approximation coefficients; again separating the low frequency components in to approximations and details. This process is repeated with entropy, energy, and/or a cost function being computed after each level of decomposition as a means of optimizing the decomposition process.

In cardiac analysis, the acceleration data may include numerous high and low frequencies not associated with cardiac activity. High energy at the low frequency is likely to be associated with breathing and whole body motion, while high frequency components may be associated with vocalization. Since the goal is to identify those components providing the best correlation with SV, the full signal frequency spectrum was investigated regardless of its computation cost, energy, or entropy.

Figure 4:
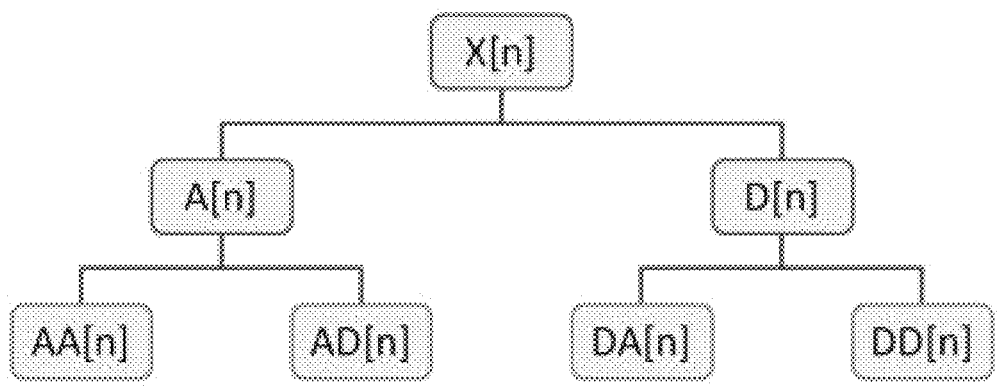
FIG. 4 shows an example of a two level wavelet tree decomposition, where the second decomposition level consists of four packets, creating a filter bank of four different filters, used as CHC genes.

Full tree decompositions, that is decomposition was performed on the details and approximation coefficients of each branch using one Mother wavelet (FIG. 4). This process was repeated for each of the mother wavelets utilized in the analysis. The first decomposition level is performed on the time sequence producing the approximation coefficients and details coefficients. The second decomposition level is performed on the approximation coefficients and the details coefficients, and represents the first Approximation Approximation (AA), the first Approximation Details (AD), the first Details Approximation (DA), and the first Details Details (DD). Another decomposition level can perform on the AA, AD, DA, and DD, and so on. The last decomposition level consists of set of filters called packets and serves as a filter bank. Full tree decomposition is applied with multiple mother wavelets creating multiple filter banks that expand the number of features allowing us to choose combinations of features that correlate best with SV. It may be possible to achieve better correlation with SV by combining packets from different mother wavelets.

An ECG signal was used to capture the ventricles contraction time (QRS complex), which serve to identify the time point to evaluate in the decomposed acceleration signal. Four decomposition levels were performed with six different mother wavelets providing ninety six different features associated with ventricle contraction acceleration energy.

The goal of utilizing the subset selection GA was to identify the minimal subset of features capable of accurately estimating the NICOM reported SVs. The NICOM provides thirty-second averages of SV and so wavelet decomposition was performed on each thirty seconds of recoded acceleration data. Eighty-five thirty-second averaged measurements were taken sequentially using the NICOM, the ECG, and chest accelerations, from a single subject during both rest and during exercising. There were five exercise periods for one hundred and fifty seconds at the same intensity and five resting periods of two hundred and seventy seconds. Data was collected while subject was at rest, in upright position for four hundred and fifty seconds. Multivariate regression was used to correlate the expressed chromosome genes 'packets energy' to the averaged NICOM SV measurements. The $R^2$ value of the regression line was used as the chromosome fitness value. The higher the $R^2$ value, the better the gene set predicts the NICOM SV.

In the CHC GA, the more fit chromosomes remain in the population until they are replaced by even more fit offspring. The fitness functions returns a two-vector, where one is the $R^2$ value, and the other is the SSS. The SSS is located at first chromosome gene. The vector selection process works by comparing two chromosomes, a parent, A and an offspring B, if $R^2(A)>R^2(B)$, then A is more fit (and vice versa). However, if $R^2(A)=R^2(B)$, then the chromosome with the smaller SSS is more fit. If the SSS's are also equal, the parent is not replaced.

The crossover operator is responsible for offspring reproduction. It consists of three operators: Incest Prevention that decides if the two parents can mate; Index Gene Crossover that is responsible for inheritance of both parents' genes to the offspring; SSS Recombination crossover that is responsible for setting the SSS gene of the offspring based on both parents' SSS genes.

The crossover operator is applied to each random pair of parents. The first step is to check the pair for incest prevention. Parents who are too closely related are prevented from mating. The distance between two chromosomes is simply the number of unique genes, in the leading portion of the chromosomes out to the furthest genes an offspring might inherit (the larger value of SSS genes from the two chromosomes). The initial value for the incest threshold is half of the maximum SSS, but it is decremented whenever a generation occurs in which no offspring survive. When the incest threshold drops to zero, any chromosome may mate with any other, including a clone of itself. The incest threshold dropping to zero is one of the criteria used by CHC for halt and restart decisions. This incest prevention algorithm has been shown to effectively defeat genetic drift [168]. It does this by promoting exploration, allowing only mating among the more divergent chromosomes; as long as this process is successful (offspring survive). Being self-adjusting, it tunes itself to problems of differing difficulties; when more fit offspring are being produced, the threshold remains fixed, it drops only when progress is not occurring.

Figure 5:
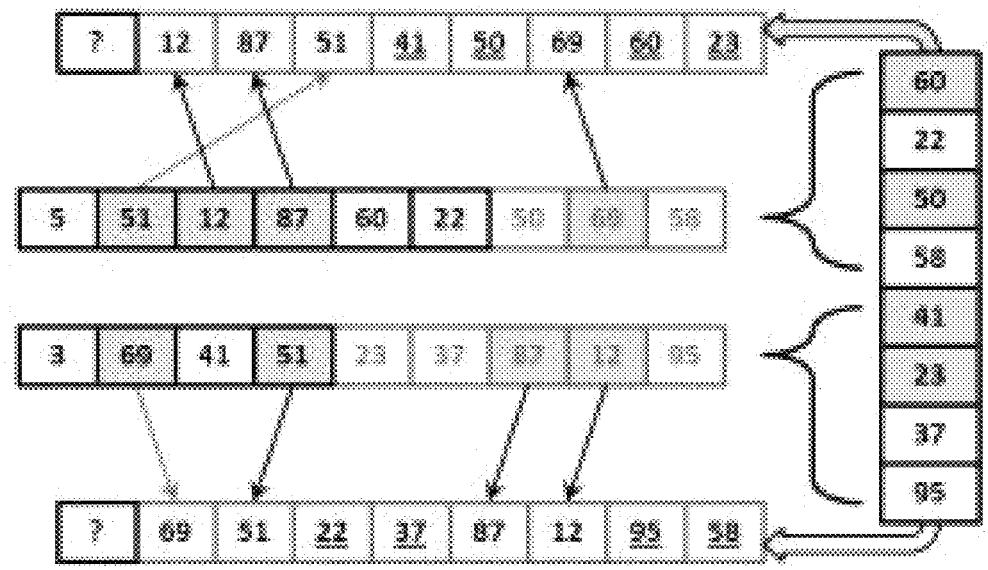
FIG. 5 shows the MMX_SSS crossover operator.

GA research has shown that "respect" is an important property for a crossover operator [199, 200]. That is, if the parents share common genes, it is important that the offspring should inherit them. The MMX_SSS operator achieves this by first copying the common genes from the parents to the offspring. However, given that there is selection pressure for smaller SSS gene values, this copy operation moves each gene one position forward, to the left, in the offspring (FIG. 5). Thus, if a gene consistently contributes to fitness, it will slowly migrate towards the front of the chromosome, from grandparent, to parent, to child. If a common gene is in the first, position adjacent to the SSS gene, it stays in the first position unless there is a common gene immediately following, in which case they switch places. The unique genes from the two parents are randomly inserted into unused chromosome slots in the offspring. These operations allow genes unexpressed in the parents to become expressed in the offspring.

Figure 6:
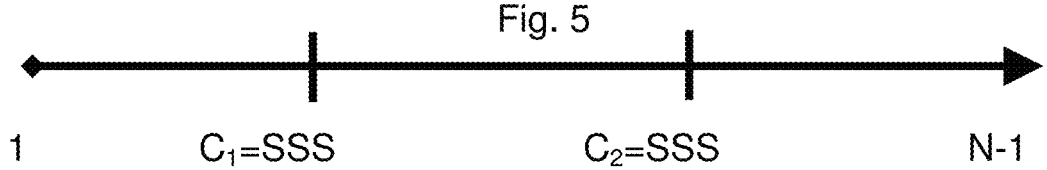
FIG. 6 shows the offspring SSS interval, where parent C1 is more fit than parent C2.

The last step in crossover is to set the values for the SSS genes in the offspring. This operation uses the "blend crossover" or BLX [149, 198]. The SSS gene for each offspring is drawn uniformly randomly from an interval defined by the SSS genes in the parents and their fitness (FIG. 6).

The common genes from the two parents are copied one space to the left in the offspring and the other genes are randomly inserted into the offspring. In this example, the first parent common gene 51 switches places first with gene 12 and then gene 87 in the next generation, (offspring one) because all three are common in both parents. Gene 69 from the second parent stays in the first place since gene 41 is not common (offspring two). The rest of the genes, the "unique" genes, are copied to a grab bag, the table on the right in FIG. 5. The two offspring randomly pick the genes from this grab bag to fill up the places that are not filled. In this case, the first offspring selects genes 41, 50, 60, and 23, which have a gray background in the table and are underlined within the first gene. The second off spring picks the genes with the white background, which are underlined in the second gene. Blend crossover set the SSS gene.

The interval is first set to that bounded by the parental values, and then extended by fifty percent in the direction of the more fit parent. In the example illustrated in FIG. 6, the parent with the smaller SSS gene value, being the more fit, biases evolution towards smaller SSSs. The opposite circumstance may also occur. In fact, this condition (the more fit parent being the one with the larger SSS), is what determines the limit for the computation of unique genes for incest prevention.

To evaluate this approach, a series of experiments were performed to test each aspect of the algorithm; these experiments are described in sequential order. All experiments used seismocardiogram data from a single subject obtained at rest and while undergoing mild exercise (light bike pedaling in an upright position with back support). Four levels of wavelet decomposition were performed on successive thirty-second time intervals. Six mother wavelets were utilized: Daubechies, Symlets, discrete Meyer, Coiflet, Biorthogonal, and reverse Biorthogonal. A "ground truth" SV value was obtained for each thirty-second interval from the NICOM. This produced a data set with 96 features (6×24), and a "true" SV for each of the 85 intervals that were measured. The maximum value of SSS was set to 32 assuming the GA could obtain results with a subset much smaller than this. Thus, the chromosome contained 33 genes, one for SSS and 32 packet indexes. For fitness to maximize, the $R^2$ from a linear regression of the packets energy to SV was selected. The population size was one hundred, the number of soft restarts was set to ten, with maximum zero accepts (restart condition) set to three.

Figure 7:
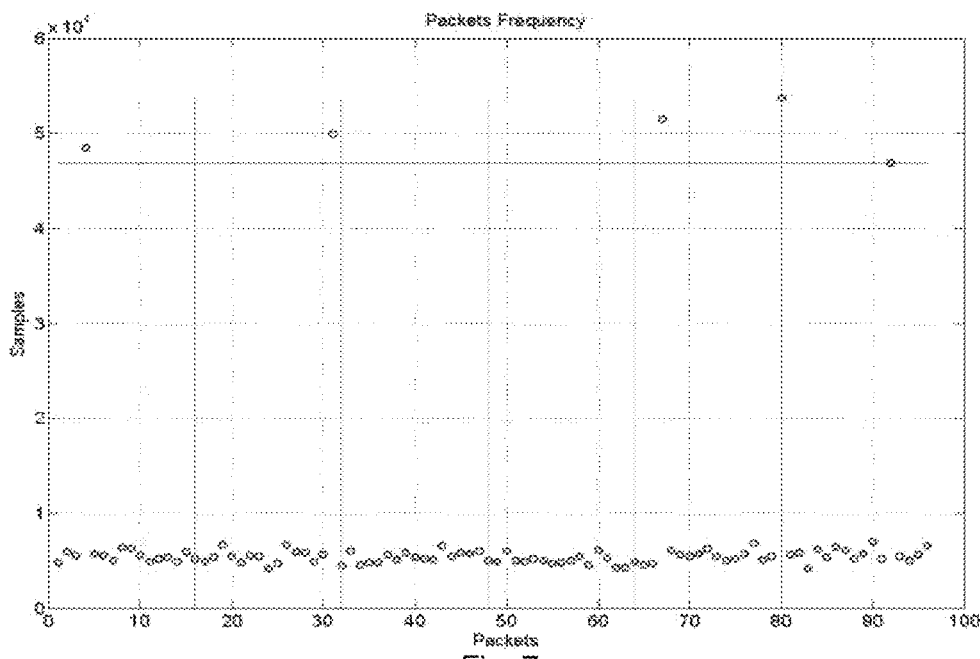
FIG. 7 shows characterization of experiment one. The X axis represents evolution time, either individual chromosome evaluation (upper panel) or generation (middle and lower panels). In the upper panel, the Y axis is the individual features and there is a point for each index that was present in the population. The middle panel shows the SSS gene of all chromosomes within the population of each generation. The bottom plot shows evaluation of the best, worst, and average chromosomes within the population of each generation.

The first experiment was directed toward achieving a maximum $R^2$ value, but showed little evidence of convergence. FIG. 7 presents several plots that characterize an experiment. All features appear to have been sampled throughout the run, but evolution was unable to eliminate many features so that a great many features remain in the population throughout the run (upper panel). In the middle panel, it can be seen that within a few generations the population SSS gene has converged to 32 (SSS max) indicating that no smaller value was competitive. In the lower panel, it can be seen that the population rapidly converging on an $R^2$ value at or near 0.988. Thus, the GA was unable to distinguish any features as any better than any others, and so used the maximum number of features it was permitted (32). The GA discovered many combinations of features that were able to predict SV nearly perfectly. In the example experiments shown FIG. 7 the soft restarts are clearly seen as the introduction of genetic diversity (upper two panels) and a drop in average and worst population fitness (lower panel). There are 10 soft restarts, as per the control parameter chosen.

FIG. 7 shows a characterization of experiment one. The X axis represents evolution time, either individual chromosome evaluation (upper panel) or generation (middle and lower panels). In the upper panel, the Y axis is the individual features and there is a point for each index that was present in the population. The middle panel shows the SSS gene of all chromosomes within the population of each generation. The bottom plot shows evaluation of the best, worst, and average chromosomes within the population of each generation.

Figure 8:
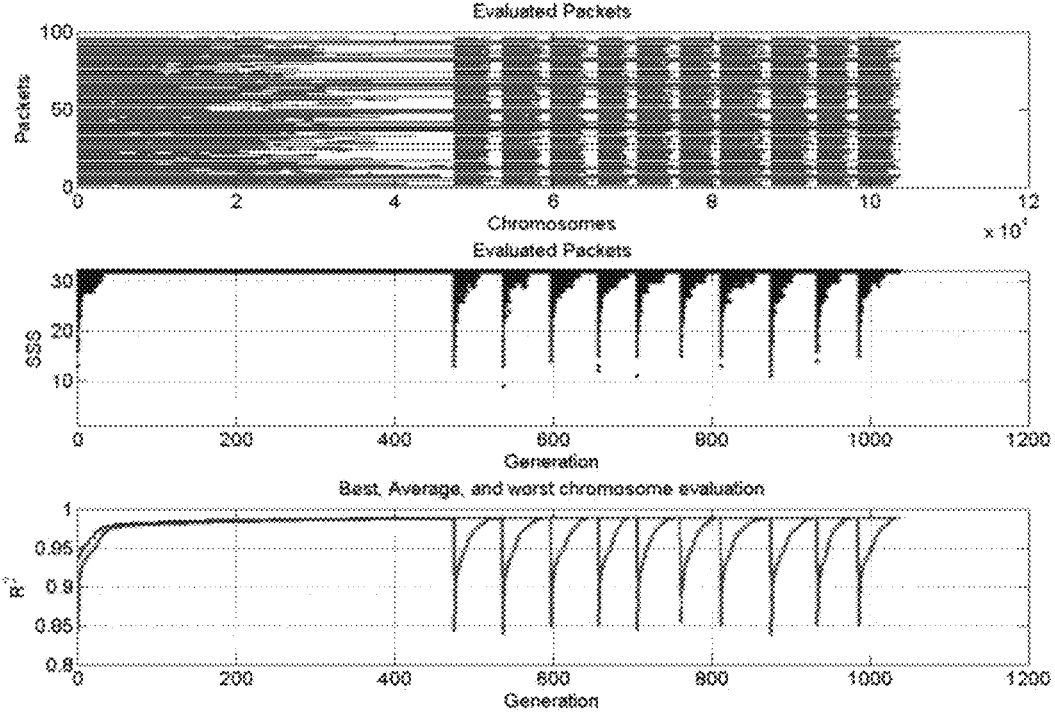
FIG. 8 shows results from the second experiment, where the perfect (seeded) solution was found. The GA successfully detects the five features. The upper panel shows that as the number of generation increases the seeded features are observed. As the number of generation increases the chromosome with the same fitness value but smaller SSS gene survives, as the middle panel shows. A good solution is found at the initialization stage as the lower panel shows.

Failure of convergence from experiment suggested verification of the algorithm. A perfect solution was embedded in the data, to test the algorithm's ability to discover it. A set of five features was selected and their values "doctored" so that together they have perfect SV correlation. These features had indexes of 4, 31, 67, 80, and 92. (i.e., widely distributed among the pool of features). The "doctored" features emerging as the only genes left in the population after about one hundred generations (FIG. 8). The SSS value (middle panel) first rises towards SSS-max as the combinations are sorted out, and then falls to the value of five as selection pressure eliminates chromosomes with more features than the five needed to achieve perfect performance.

FIG. 8 shows results from the second experiment, where the perfect (seeded) solution was found. The GA successfully detects the five features. The upper panel shows that as the number of generation increases the seeded features are observed. As the number of generation increases the chromosome with the same fitness value but smaller SSS gene survives, as the middle panel shows. A good solution is found at the initialization stage as the lower panel shows.

Figure 9:
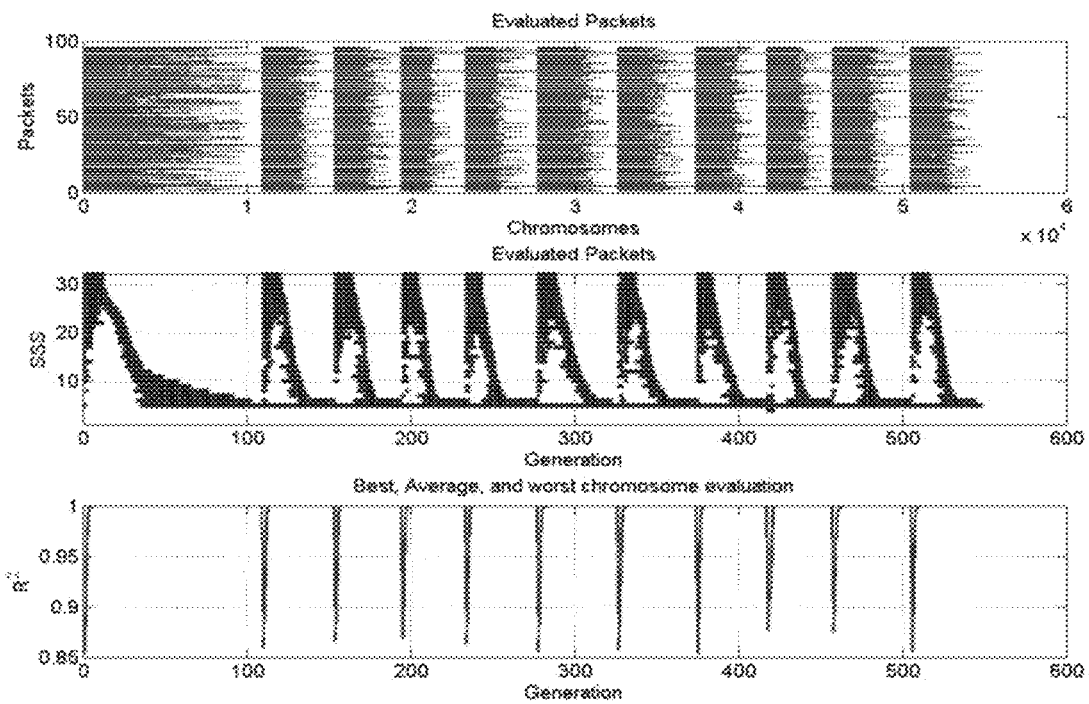
FIG. 9 shows the "seeded" features are sampled many more times than other features. Vertical lines separate the different mother wavelets.

FIG. 9 shows the number of times each feature was sampled over the entire run. The five doctored features were clearly preferred by evolution, but even the non-doctored features were each sampled several hundred times while the GA sorted through the combinations to locate the good one. Thus, the algorithm was observed to work as expected when there is one perfect solution among a sea of poor ones.

Figure 10:
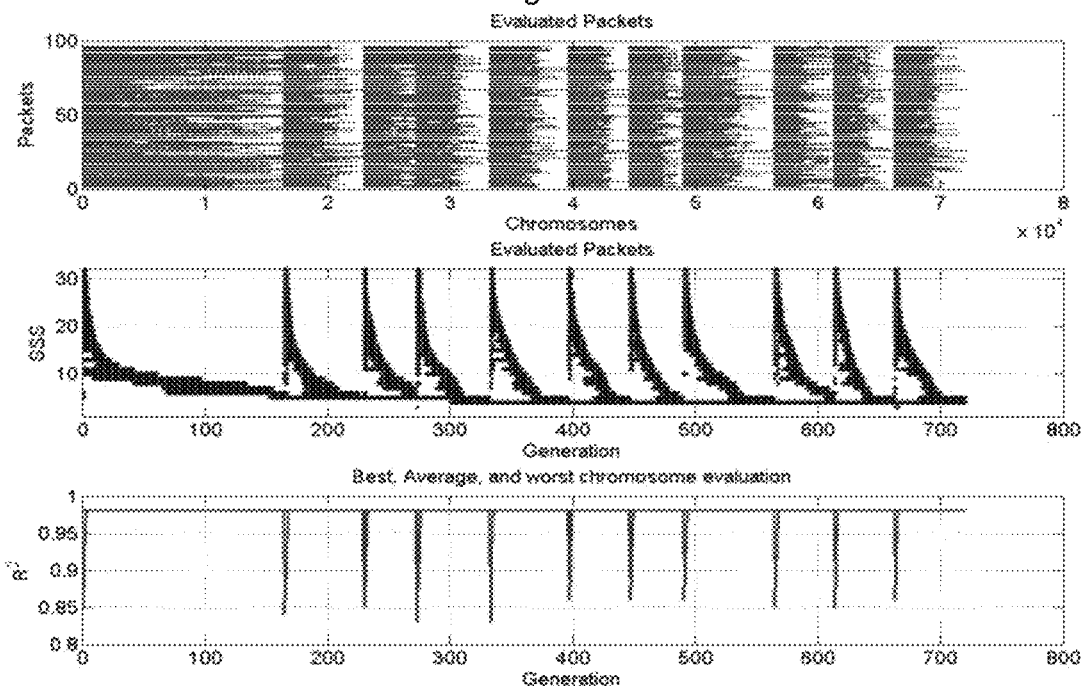
FIG. 10 shows a seeded solution is embedded in the dataset, and all data are perturbed with Gaussian noise. Similar to experiment one, the GA fails to converge.

The algorithm was then challenged by perturbing the data with Gaussian noise, where each feature is the original value plus twenty percent Gaussian noise. The characteristic pattern of convergence failure was observed (FIG. 10). Without an easy-to-find superior set of features, the algorithm could only promote the largest possible subset (SSS max) of just about any of the noisy features. Each feature adding a tiny increment to improve of $R^2$ value. It was hypothesized that the problem might be the sensitivity of the original algorithm's hierarchical selection scheme on any difference in the first dimension of fitness ($R^2$), no matter how small. Selection for small subset size was never triggered because ties on $R^2$ virtually never occurred. This feature of the problem makes it different from previous applications of this algorithm that were on classification tasks, where the fitness was usually to reduce classification errors or some similar metric. These errors being modest discrete integers often resulted in ties.

Figure 11:
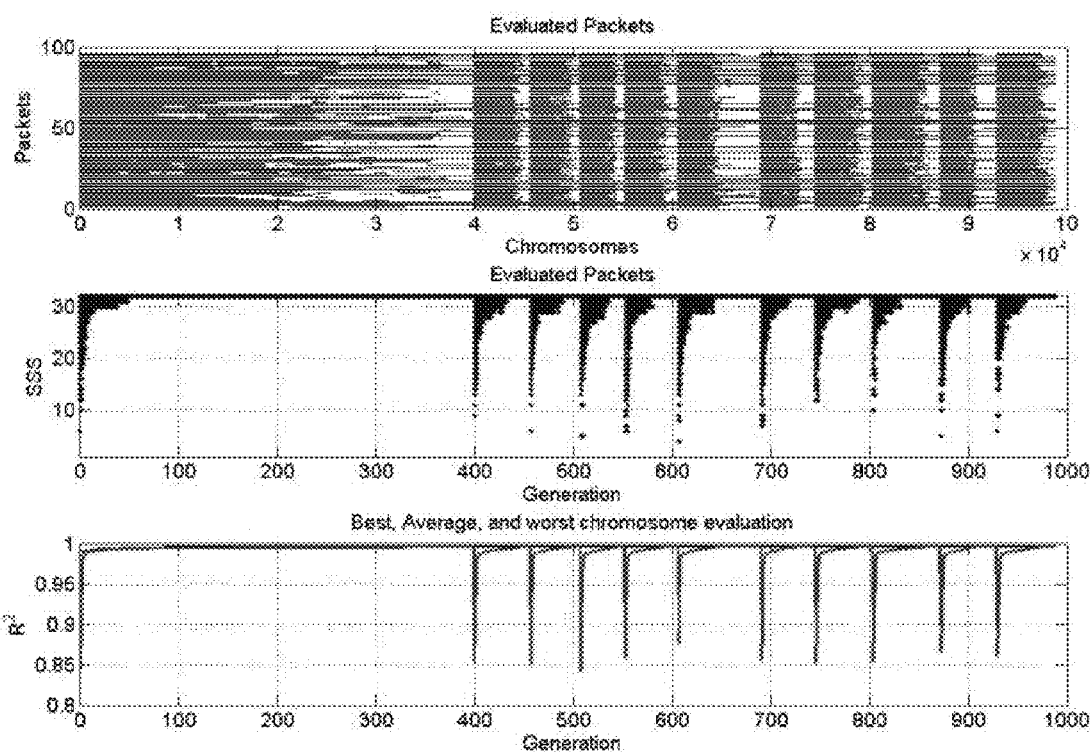
FIG. 11 shows a reduction of the precision of $R^2$ results in successful convergence. Smaller SSS is achieved since weak features are eliminated.
Figure 12:
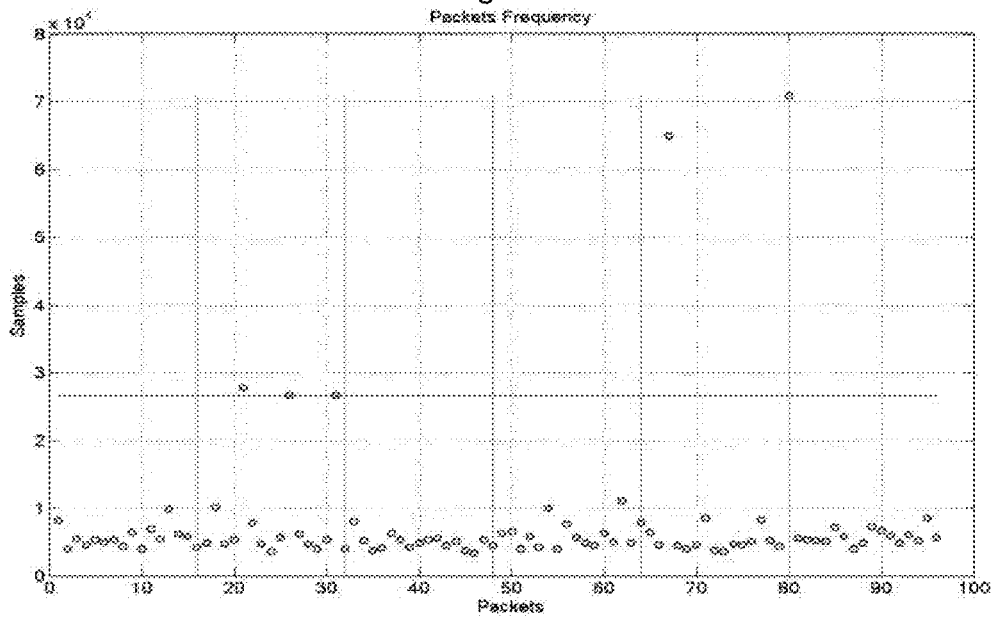
FIG. 12 shows the "seeded" features which are strongly connected are again preferred, but (compare to FIG. 9) weak connections are eliminated and new connections are observed.

To test the influence of $R^2$ on convergence, the number of significant digits in the value of $R^2$ reported by the regression to the GA was reduced. By setting this to two significant figures, it was declared that chromosomes that differ in $R^2$ by less than 0.01 should be considered equivalent, thereby allowing for ties and enabling the second level of the hierarchical fitness selection to kick in. One may also think of this as an admission that an $R^2$ estimated from a sample of cases must of necessity contain a certain amount of noise (sampling noise rather than measurement noise); allowing the GA to over-exploit noise provides no benefit. This strategy resulted in a return of effective performance even though the problem is now more difficult because of the noise perturbation (FIG. 11). Correspondingly, it now takes longer to locate the good feature set (FIG. 12). Perturbed features 67 and 80 correlate better with SV and so are located earlier in the course of evolution. The features with weaker connections, 4, 31, and 92 were not included in the final result by the GA. Feature 31 has been sampled more times since it still has decent connection to the residual of SV once features 67, and 80 are included in the regression. However, other features 21 and 26 (plus their noise) provided better results and were chosen by the GA. The end result provided four genes 21, 26, 67, and 80 with final $R^2$ of about 0.98.

Figure 13:
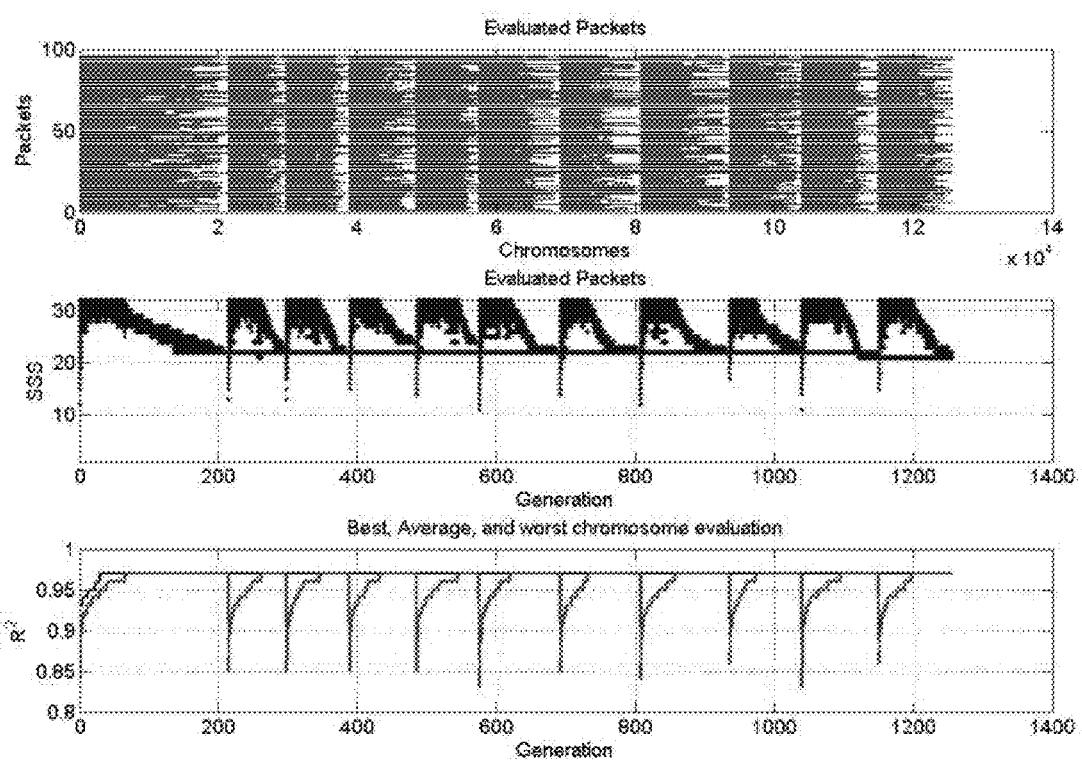
FIG. 13 shows convergence of original dataset with reduced precision on $R^2$. The SSS converted to twenty one (middle panel) and the best chromosome maintained good correlation (bottom panel).

Having an indication that over-precision was precluding convergence in the presence of noise, the original dataset was rerun with $R^2$ reduced to two significant digits. The patterns that indicate successful learning was observed, and this time without the presence of doctored data. Now SSS evolves, first to 22 packets (in the first convergence, and the next eight soft restarts) and finally to 21 and 22 in the last two soft restarts (FIG. 13 middle panel). The $R^2$ reached about 0.97 (FIG. 13 lower panel), and the best packets can be seen emerging from the chaos (FIG. 13 upper panel).

Figure 14A:
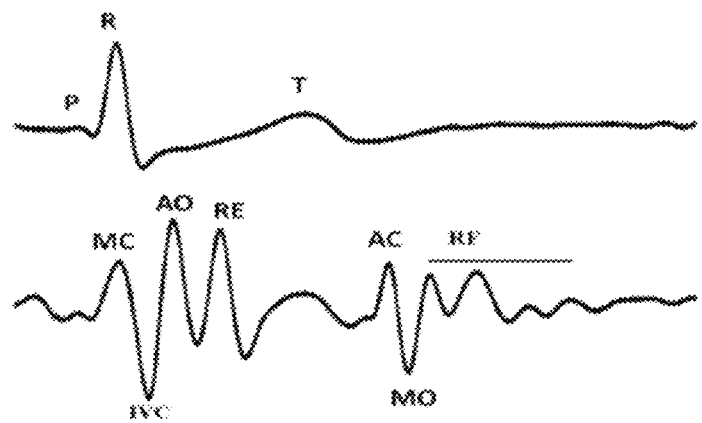
FIGS. 14A, 14B and 14C show chest acceleration recording reported by various investigators, illustrating that there is not a typical chest acceleration signal.
Figure 14B:
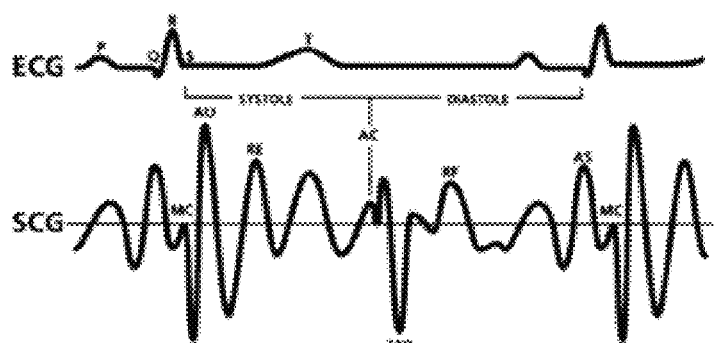
Figure 14C:
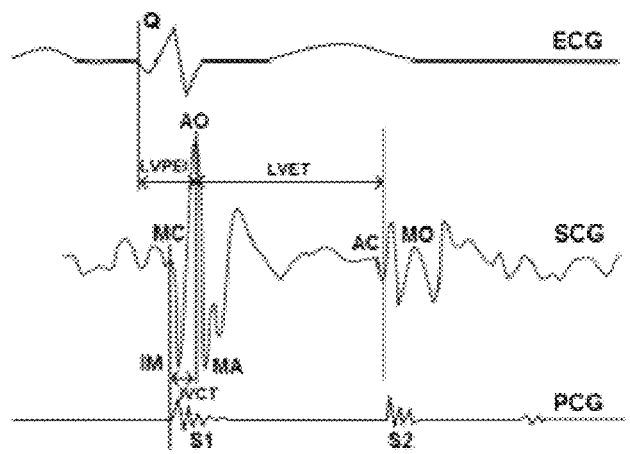
Figure 15:
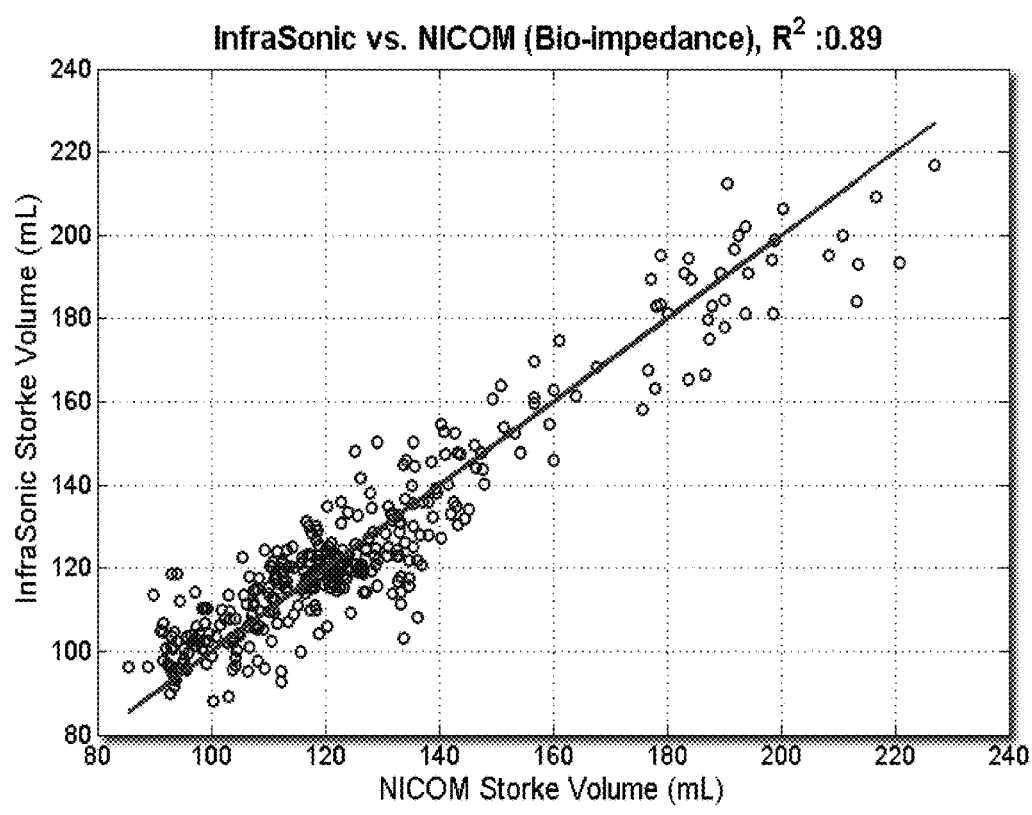
FIG. 15 illustrates stroke volume values obtained when this best filter set is applied to the recorded chest wall acceleration signals against NICOM estimates of stroke volume, where stroke volume estimates are averaged over thirty seconds to allow correlation to the NICOM data. An $R^2$ value of 0.89 for the four young adult men is obtained.
Figure 16A:
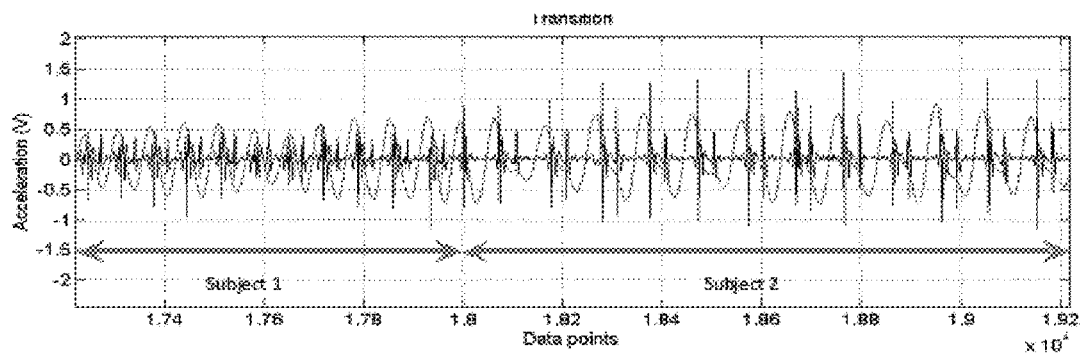
FIGS. 16A and 16B show an example of automatic scaling adjustment based on the previous acceleration data that estimates subjects' heart rate. The arrow points on the adjustment time location.
Figure 16B:
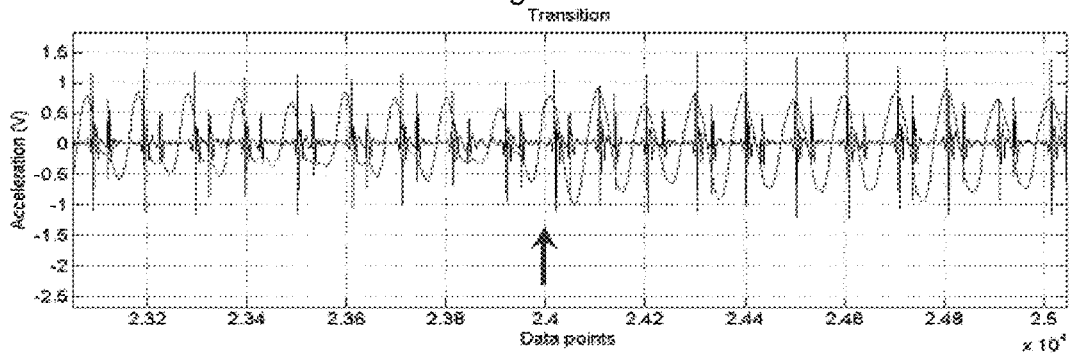
Figure 17:
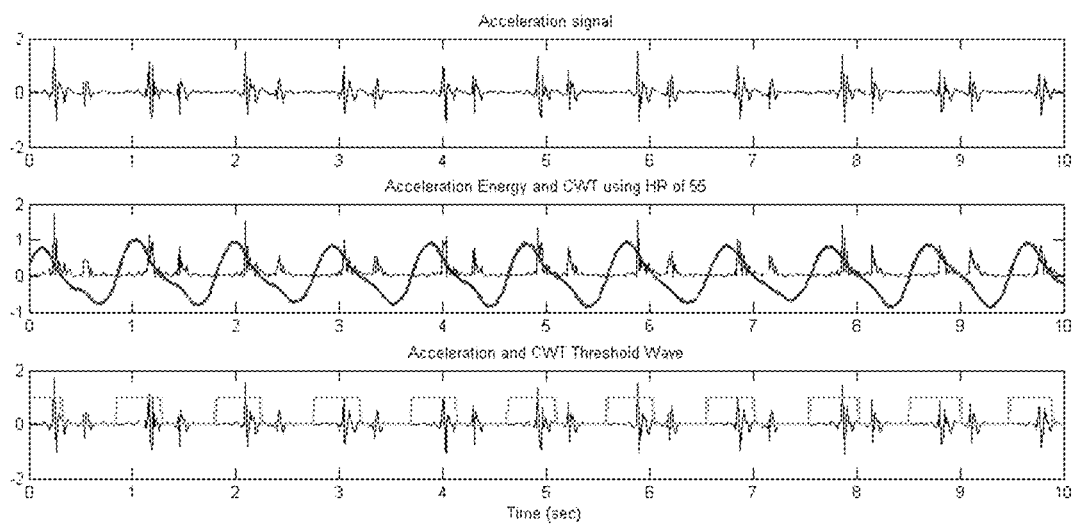
FIG. 17 shows a CWT approach to isolate the desired windows using chest acceleration.
Figure 18:
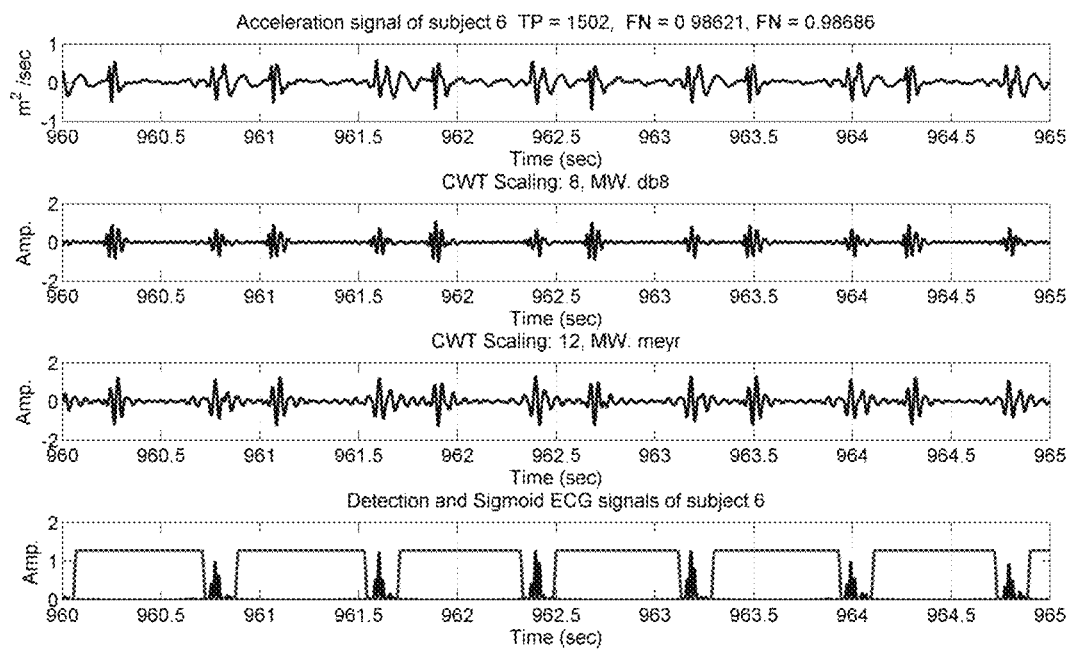
FIG. 18 shows detection of heart contraction time location for one subject.
Figure 19:
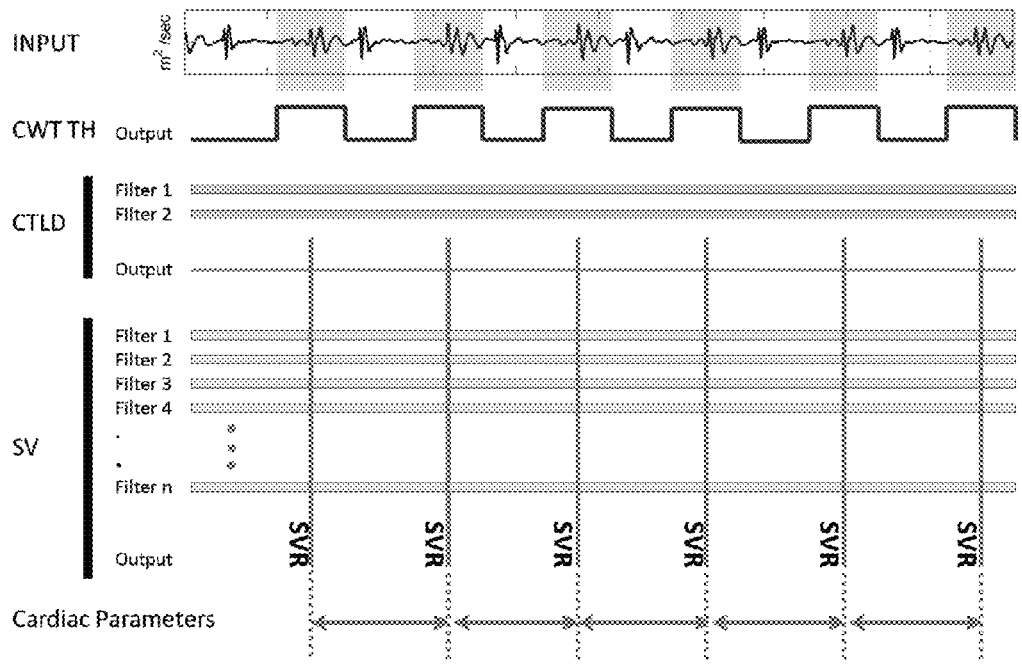
FIG. 19 shows the three algorithms combined to provide cardiac information
Figure 20:
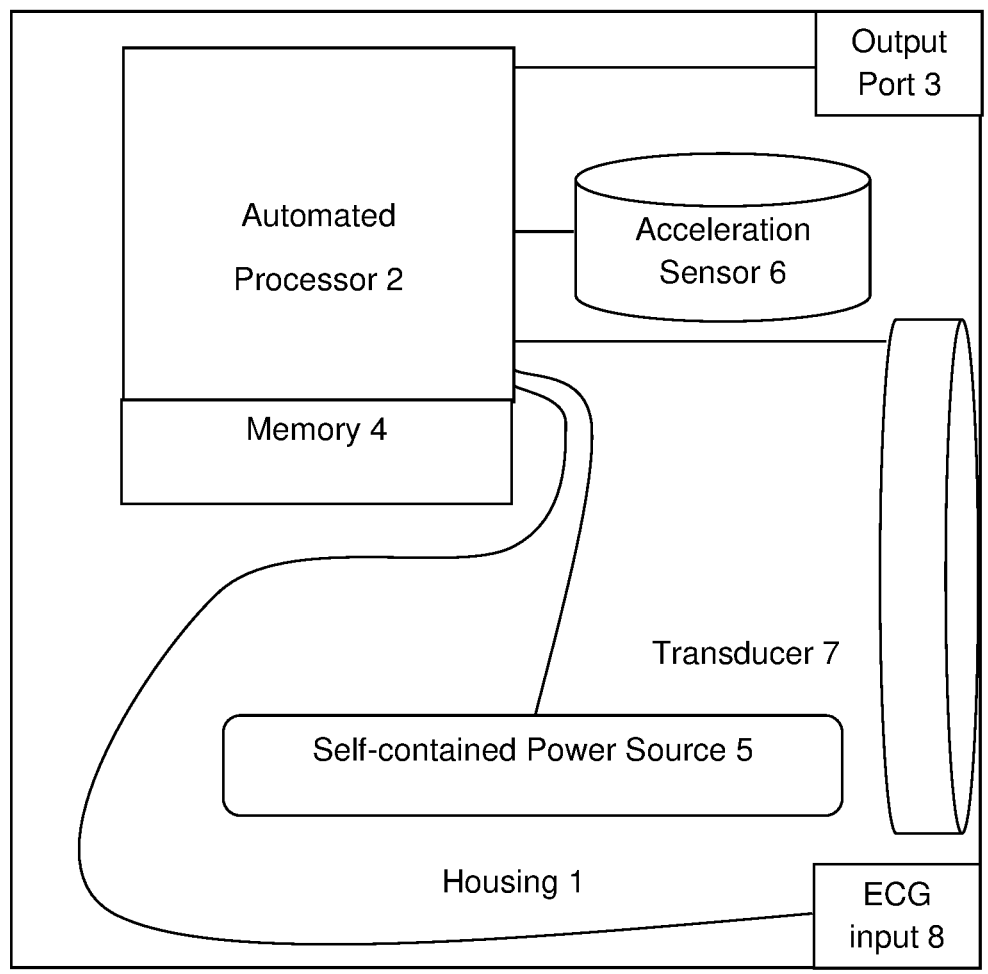
FIG. 20 shows a semi-schematic drawing of a device according to the present invention.

FIGS. 14A-14C show chest acceleration recordings reported by various investigators, illustrating that there is not a typical chest acceleration signal. MC: Mitral Valve Closure; IVC: Isovolumic contraction; AO: Aortic valve opening; RE: Rapid ejection; AC: Aortic valve closure; MO: Mitral valve opening; RF: Rapid filling; AS: Atrial systole.

The CHC genetic algorithm with the MMX_SSS crossover operator has previously been applied to the task of feature selection in bioinformatics classification tasks. This algorithm may also be applicable to feature subset selection tasks in time series data processing, but the use of a high-precision first fitness metric such as $R^2$, seems to require a judicious reduction in significant digits provided to the GA in order to induce ties so that the second metric (SSS) may become active. In classification tasks, ties are common since counts of classification errors have a limited dynamic range. This shows that a tradeoff between sensitivity to small improvements in accuracy and the desire for small subsets is appropriate.

This algorithm can be applied to selecting high performance, small set of signal features that can be combined to yield accurate metrics of some signal content. Finding specific mother wavelet packets that can be combined at the energy level without full waveform reconstruction can enable computationally inexpensive ways to extract information from time series data.

The CHC genetic algorithm with the MMX_SSS crossover operator has previously been applied to the task of feature selection in bioinformatics classification tasks. Evidence is provided that this algorithm may also be applicable to feature subset selection tasks in time series data processing, but the use of a high-precision first fitness metric such as $R^2$, seems to require a judicious reduction in significant digits provided to the GA in order to induce ties so that the second metric (SSS) may be-come active. In classification tasks, ties are common since counts of classification errors have a limited dynamic range. This work seems to show that a tradeoff may be needed between sensitivity to small improvements in accuracy and the desire for small subsets.

The last experiment yielded good correlation and as results the same algorithm and settings are used in this case to find a solution for four subjects. The filter bank was expanded to 640 features derived from different mother wavelets and another six features derived from subject physical measurements (Chest volume, Chest circumference, height, weight, BMI, BSA). The GA population size was increased to 200, allowing farther exploration of the landscape for the optimal solution. Similar to the previous experiment FIG. 8 shows the results from a run where 29 features (middle panel) are identified for a solution, $R^2$ of 0.89 (lower panel). FIG. 9, shows the features which are most occurring through the entire run.

Example 4

Finding the contraction time location using the acceleration signal is challenging compared to extraction from an ECG signal. As described above, the ECG R-wave was used to define the contraction time location to extract values from the filter set using a regression line to compute the SV. However, cardiac parameters including the contraction time, can also be estimated using only an accelerometer. GAs are also used to find a global solution. A computationally efficient method is provided.

Extracting the timing of heart contraction from acceleration data at the chest wall using a standardized algorithm for all subjects is challenging, because the chest acceleration signal is individual based on body characteristics, since each individual chest vibrates differently when the heart contracts. Moreover, the chest vibrations due to the heart contraction are affected by breathing motions, speech and other motions. The subject heart acceleration may also vary from one heart beat to another. The ECG R wave is clearly distinguished in all subjects where the first heart sound within the acceleration signal of each subject varies in amplitude.

The low pass filter was set to 50 Hertz and the high pass filter was set to 2 Hertz.

The ECG QRS complex function was used to extract packet information at the heart contraction time location, as the ground truth for heart contraction time location. Based on physiological assumptions, a time segment was chosen after the ECG contraction time location to serve as the window of opportunity for capturing the heart contraction time location via acceleration data. True Positive (TP) detection is considered as heart contraction detection based on the acceleration data in this window. Otherwise, if no heart contraction is detected a False Negative (FN) accrues. If a heart contraction is detected outside of the window, the detection is considered as False Positive (FP).

The heart mechanical activity follows the electrical activity. The time lag of the heart contraction and accelerometer electrical circuit after the ECG R-wave is about 50 milliseconds. The effective time lag is dependent on filter delay. Since the data was analyzed at 100 Hertz and four decomposition levels performed, the total time scaled energy observation of a packet per data point is 160 milliseconds. Therefore, the window in which a TP has occurred is equivalent to the same time scale window following the ECG R-wave. Optimal detection means that all heart contraction time locations from the acceleration signal are located in the TP windows, and there is no heart contraction detection elsewhere. The Sensitivity and the Positive predictive value were measured and calculated.

Two approaches were investigated to detect heart contraction from the acceleration signal; the Discreet Wavelet Transform (DWT), and the Continuous Wavelet Transform (CWT). The CWT calls for more redundancy and may provide more features which allows easier detection. The DWT calls for better noise elimination, where signal components can be eliminated. Both approaches use a detection function and evaluation function which compare the detected contraction time location to the ECG QRS time stamps. In general, the DWT convolves the input signal with specific filter coefficients and decimates the signal by half to eliminate redundancy. After one level of decomposition the approximated signal is half of the input signal length. The next decomposition will convolve the approximated signal against the same mother wavelet low pass filter coefficients. The second decomposition level investigates a narrower band of low frequencies than the first decomposition. Most likely, the best frequency detection occurs when the mother wavelet filter coefficients represent the input signal. In this case, that happens at higher a decomposition level, when the mother wavelet is similar in shape to the input signal.

The second approach is to use the CWT to capture information which the DWT may miss. The CWT calls for redundancy since the frequency component of the signal is redundant after performing convolution. The CWT uses the actual mother wavelet coefficients as opposed to the DWT that uses the Multi-Resolution Approximation (MRA) equation. As the scaling function increases the number of the mother wavelet coefficients increases. In general, to capture the desired signal information the mother wavelet shape should match the desired information shape (i.e. similar frequencies) and this is done by choosing the correct scaling.

Both CWT and DWT are good filtering tools. They are similar approaches, but have different advantages and disadvantages. Since, with the DWT multiple decomposition levels are available, the option of sharper filtering to capture specific frequency components is possible, noise is better reduced than with the CWT. The CWT does not compress the input signal for sharper filtering. Instead the mother wavelet "stretches", requiring more computations than the DWT, and so redundancy of the frequency components may provide better feature detection.

The output data from the DWT brute force and CWT brute force functions were processed via a detection function that detects the heart contraction time location. The contraction detection function output is then evaluated using the evaluation function discussed above, based on the ECG QRS heart contraction time location. In one embodiment, a function divided the processed signal to many segments or "windows". Each window was evaluated by its maximum energy peak which was compared to an average threshold number. The average threshold was set to half of the averaged last ten peaks. After the CWT threshold algorithm was tuned, each threshold window then consisted of the positive segments of the CWT threshold output.

The DWT brute force algorithm evaluates all the possibilities to compute a solution for heart contraction time stamp. Each Mother wavelet packet combination set is evaluated. In this case, there are two loops. The first one changes the mother wavelet selection and the second changes the packets combination selection. In each evaluation the input signal is decomposed to a three decomposition level, packets are selected for reconstruction, and the reconstructed signal is processed by a computational function before it is evaluated by the peak detection and evaluation functions. Each choice of MW and packet combination was stored in a chromosome structure. The selected MW is at the first position, the computational function is at the second position, and the last eight positions are occupied by packet reconstruction selection. Each MW was assigned a number which was parsed using a parsing function. The Computational Function (CF) was set prior to the run and was applied on each MW packet combination. The packet combination used eight characters of ones and zeroes to define the selected packets for reconstruction; one selects the packet and zero ignored the packet.

The maximum detection from the brute force run was about 97 percent, but the second heart sound was also sometimes counted as a contraction location. Therefore, the detection false positive rate was about 50 percent and the calculated heart rate was double the measured heart rate.

Good results were obtained using two subjects. However, when the analysis was run on a third subject it failed to detect the heart contraction time, because the threshold function eliminated the heart construction segment. Similar frequencies where associated with the third subject heart construction, first heart sound, and the second heart sound. Therefore, it was concluded that a Genetic Algorithm was needed to generalize an algorithm to fit all subjects.

Example 5

A Genetic Algorithm can be a useful tool to discover the global optima solution or a solution which is close to it in a large landscape. Since there are deviations among subjects, a large population of subjects is required to formulate a generalized algorithm, e.g., four females and eight males. Basic information was collected from each subject (like height, weight, age, and etc.), followed by collecting acceleration data for ten minutes while the subject was in a supine position, ten minutes while subject was in an upright position, four minutes while subject was in an upright position and talking. In the following GA detections, DWT and CWT, only three minutes of the male subjects' data was analyzed while in an upright position. Computing multiple filters and evaluating the solution was very computationally expensive. Therefore, selecting a portion of data from each subject that is sufficient to represent deviation within the full data spectrum (all subjects) is expedient. Three minutes were selected as a sampling duration, to record at least a hundred heart beats for each subject to have confidence in the solution. Since data of one subject were not collected correctly, it was discarded. A total of seven male subjects in an upright position and three minutes of recording while sitting quietly were analyzed where the ECG signal was clean of noise and the R wave was fully detected.

A chromosome structure was provided to evaluate the selected packets, MW, Computation Function (CF), and threshold function. Previously, the CF and threshold function were set to be constant. Here, the GA chooses the best threshold function and CF to maximize detection. Also, multiple wavelet transforms were combined to provide better detection by the GA. The CHC GA was used again because of its robustness. Here, the crossover operator and chromosome structure were modified. An example chromosome provides two MWs at two decomposition levels. MWa has a threshold function THa and corresponding packets aB0-aB3. MWb has a threshold function THb and corresponding packets bB0-bB3. The CF computes the output combination for the two.

The computation function combines and performs mathematical operations on each wavelet transform. Here, five functions were available to each chromosome. Those functions were chosen based on some assumptions and for being different from each other. Therefore, a function that provides a good result within the Evaluation Function will rise quickly and eliminate others. Each function does element operation on MW Signals (MWS) after decomposition, thresholding, and reconstruction.

The threshold function performs mathematical computations on the decomposed wavelet transform before reconstruction. The purpose of this function is to eliminate noise and focus on the features that are associated with the heart contraction. The packets to be reconstructed are equal to a function of the decomposed packets. In some cases, a threshold value is set at the beginning of the run to save searching time.

The CHC GA was used again to converge to a near-global optimum solution. However, a different crossover was used to generate offspring since chromosomes had a different structure. In the reproduction process a bit representation was used for the packet selection and a numerical representation for the MW, threshold, and CF representation. The HUX (Half Uniform crossover) was used for packet selection crossover, since it has general been observed to perform well when using bit-wise operations. The common genes transfer to the offspring and their location do not change oppose to SSS_MMX crossover, where the common genes moves one step towards the beginning of the chromosome. The rest of the genes are processed as follows, where half of the unique genes are chosen randomly, line under, to change their state (switch to the opposed binary state.)

The blend crossover (BLX) crossover was used on the MW, threshold, and CF genes. This crossover was used before with the SSS_MMX crossover on the subset size gene. The BLX crossover formula is given below where Gene Parent one (GP1) is smaller than Gene Parent two (GP2).

If the upper bound of the Interval is greater than the number of features, it is set to be equal to the number of features. If the Interval lower bound is smaller than one, it set to one. Gene Parent one (GP1) and Gene Parent Two (GP2) represent the rage which is extended by 50 percent to the direction of the more fit parent GP2, where a random gene can be selected.

The DWT GA evaluation function was similar to the brute force DWT and it included many function in it. The evaluation function reads the chromosome structure and sets the packet selection parameters using the parse function from the brute force DWT evaluation to define the MW function. DWT decomposition is computed, then the threshold function is computed on the selected packets, and the waveform is reconstructed. The cost to compute the DWT is calculated using the cost function. The computation function (CF) does element mathematical computation which provides better detection. The output from the CF is then multiplied by an initial CWT threshold function which determines a vague window of the first heart sound time segment. This window is used to eliminate the second heart sound. The processed waveform is then transferred to a peak detection function which determines the contraction time location. Those time locations are compared to the ground truth ECG signal and TP, FP, FN are calculated. A sigmoid evaluation function was computed which also has been used to evaluate each chromosome. Better results were found using the original evaluation function.

The main purpose of this algorithm is to isolate the first major acceleration deviation from the second one (in phonocardiogram, first heart sound S1 from the second heart sound S2). As a result, this algorithm is able also to detect subject heart rate, number of beats per minute. The chest acceleration signal is more challenging than the ECG for heartbeat detection, since each individual chest vibrates differently when the heart contracts. Moreover, the chest vibrations due to the heart contraction are affected by breathing motions, speech and other motions. This function is used after the brute force approaches had difficulty in isolating the heart contraction phase from the relaxation phase due to heart valves closing sounds.

The CWT threshold function defines the segments to be analyzed. It starts by initializing the HR to 60 beats per minute. The CWT scaling is calculated based on the HR and different scaling is selected based on the HR.

The selected scale is used to scale Daubechies five MW which selects a window where contraction occurs. Originally, the DWT GA detected twice as many heart contractions as were measured. The Evaluation function was modified many times to achieve better results but the DWT GA was not able to provide a good solution since HR is so different from one subject to another. The positive predictive values were around fifty percent. Since this function depended on the HR, it solved this issue. Heart rate is measured by counting the number of threshold windows per minute, and is used is scale the CWT function accordingly. The sigmoid evaluation function uses the ECG signal to generate a sigmoid like function around a small window after the heart contraction occurred.

A heart contraction time location at this window will result in no penalty. If the detection occurred at the edge of the window, a small penalty is added. If detection occurred outside of the window the full penalty is added. If no detection occurred, a no-detection penalty is added, which is greater than a bad detection penalty. The window consists of both the sigmoid equation and its flipped version where the variable X starts from −2 to HWS, (Half Window Size), for smoothing purposes, using the equation above. After the whole signal is analyzed, the penalties are added. The GA is minimizing the sigmoid function, where the most fit chromosome has the smallest penalty.

The solution which is provided here resulted from many iteration and modification of the DWT GA, evaluation function, chromosome structure, and more. On average a full run takes several days. Note that this optimization is not performed at the time of use in the target system, and therefore time for optimization is not a limiting factor.

In this case, the search was restricted to receive an answer in a week. The number of chromosomes in a population was set to fifty and the number of MWs functions was set to one at five levels of decompositions. Data of three minutes from each of the seven subjects was used to correlate the heart contraction time location. The DWT parse function was used again and was modified to a smaller number of MWs.

After the second soft restart, the GA was not able to converge to a final solution until it hit the maximum number of generations. The GA was able to identify a MW function that best suits the converged packet combination, evaluation type, and threshold function type. This run included four evaluation functions and seven threshold functions.

Note that, for any given subject, if calibration data is available, such as CO from a NICOM unit, then the algorithm may be tuned to that specific person.

The evaluation function is intended to maximize the detection; therefore, more weight was given to the detection of a heart contraction time location than to wrong time location detection. During the run the sigmoid function and the evaluation function were used. The evaluation function was modified to specifically weight sensitivity and positive predictive values.

The evaluation of the best chromosome from this run was detection (sensitivity) of 98.62%, and positive predictive value of 98.56%. That means that the detection was mostly at the right time and at the right location. This solution is sufficient to determine CO and average SV. Note that the "gold standard", thermo-dilution has ~80% accuracy and NICOM has ~65% correlation. Missing a heartbeat in a minute is at most 2% from 100% detection. Therefore, the provided solution is useful and sufficient for most purposes.

One of the key components is to eliminate the low frequencies from the collected data since they provide an offset noise. This solution eliminates the lowest packet which includes those frequencies, and provides a satisfactory solution. Moreover, this solution eliminates more than half of the packets and those packets are next to each other, reducing computational cost.

A final goal was to create a prototype that uses a low power microcontroller. The less computation required, the less power is required, the smaller the microcontroller can be, and longer monitoring is available. Therefore, the optimized solution provides a good solution to detect the heart time contraction.

Example 6

A second method to determine heart contraction time location is the Continuous Wavelet Transform (CWT). The CHC GA was used to determine the best filter set to extract the heart construction time location. Similar to the DWT GA, a computation function was used. However, the computation function was set to be constant and was changed manually, from one run to another. Two different types of Gas were performed. In the first GA, the evaluation function was a regression line based on the chromosome genes, and the second GA was a convolution-based approach for each of the chromosome genes. In the first CWT GA, the features were a result of the CWT output using multiple scaling and MWs. A GA as discussed above and its crossover were used to determine the best filter set that provided the optimal heart contraction time location from the acceleration data based on the ground truth, the ECG data. The same evaluation function as the DWT GA was used to evaluate each chromosome.

This GA was run on a server farm with 24 cores, to speed up the GA process. The run took three days to converge to a solution with multiple soft restarts. Matlab, CWT function was used to compute the data base (features) before the GA process. Then, the CWT GA searches for the optimal solution within the data base. Each of the CFs used in brute force approach where used.

This GA offered two appealing solutions. The first solution has better sensitivity where the second has better positive predictive value. The first solution used fewer filters than the second solution. The first solution had a sensitivity of 0.9862 and positive predictive values of 0.9869 and performed element multiplication of the selected filters. The solution consisted of two filters which is a reasonable solution for a microcontroller with limited computational power. In both cases, the maximum SSS was set to sixteen genes, which provided a good search base, where the GA was able to converge to a smaller SSS. The first solution was able to converge on the optimal solution five times.

In some cases, the GA is not able to converge. In this case, on the fifth soft restart the GA was not able to converge which resulted in reaching to the maximum number of generations (10,000).

This first solution provides two features (filters) which together provide the optimal solution. Those two features were sampled more often than the rest of the features, which indicates strong connections between them.

The second solution consisted of three filters and provided a better positive predictive value than the first solution. However, it has lower sensitivity. Here, summation of each of the filtered signals was performed, which used more filters by doubling the scaling of each MW. Also, in this solution, the filters (features) which contribute to the optimal solution were sampled frequently, but not all were sampled the most. The features with the strongest connection rose first, but the features that contribute to the global solution, which took generations to evolve, were not necessarily sampled more often. In this case, feature 686 was sampled more often than feature 6191 which was used in the global optima solution.

The two solutions provided satisfactory results, where sensitivity and positive predictive values were highly correlated to the ground truth ECG contraction time location. Both solutions used few features enabling the required computations on a small microcontroller.

In some cases, it is common to convolve two or more filters to observe specific frequencies and eliminate noise. Therefore, the same method was employed here, and a Convolution GA created. This GA convolves all the filters within a chromosome based on the subset size gene, allowing multiple convolutions to be performed and evaluated, using the same CWT filters. Chromosomes with many filters do not survive due to the convolution outcome.

The initial brute force approach did not result in a satisfactory solution. The DWT approach was not able to determine a good solution, but was not run with a large number of features due to computation time. The CWT approach provided a good solution for two subjects, but was not able to generalize the solution to more subjects. Also, like the DWT approach small numbers of features were tested due to computation time. It is important to notice that the run of each approach took more than a day to compute. Therefore, using a GA to search for a solution in a much larger landscape seems to be the right approach to continue.

Example 7

An Advanced RISC Machines (ARM) microcontroller operating using the mbed.org environment were selected for fast prototyping and performance.

The sensitive and low noise Silicon Design Model 1221 accelerometer was used throughout the early experiments, which allowed accurate recordings and identify desired features within the acceleration signal. The signal was processed using the Bio-pack M-150 data acquisition system, which has 24-bit precision analog to digital converter. It was found that lower precision would suffice, and therefore a 16 bit ADC could be used. At least a 32 bit word and 16 bit precision should be used in the calculations.

A microcontroller consists of a microprocessor, memory, clock oscillator, and input and output capabilities. Therefore, it is possible to use it without extra components comparing. As opposed to ASIC, MCUs are not customable, and have functionality limitations. MCUs perform only digital computations, and so an Analog to Digital Converter (ADC) is necessary as an input device to read analog signals. MCUs are out of the box working solutions which are provided with datasheet, drivers and code examples. They are good in implementing difficult algorithms. Their main advantage is low upfront cost, ease of programming (usually programmed in C/C++), and relative low power consumption. In the past few years ARM (Advanced RISC (reduced instruction set computer) Machines), has acquired big portion of the MCU market. This technology is wildly used in embedded devices such as smart phones, which may include Bluetooth, WI-FI, LCD or OLED display, variety of physical sensors, etc. A 32-bit (or higher) processor is preferred to compute the algorithm.

The Mbed HDK supports onboard components and off board components, allows flexible rapid prototyping. A wireless communication link between the device and a smart phone, computer, or other readout device is supported. It supports Wi-Fi, Bluetooth, and 3G communications, which are commonly available on both computers and smart phones.

The first assessment of the MCU was to check its potential to execute the required calculations in the time available between incoming samples. The most straightforward and quickest approach to test this was to measure how much time does it takes to perform a specific task. The main core of the computation is performing repetitive convolution on the input signal. The signal is filtered by multiple filters and specific features are weighted and combined to generate a SV value. Therefore, the first assessment was to measure the MCU time span required to compute the twelve different filters.

Acceleration data was collected from the MCU and the necessary filtering computed. 3.5 seconds of data were collected, and the MCU computation time span for the twelve filters obtained. The computation time for those filters took 285 milliseconds, which indicated that approximately 8% of the MCU is utilized. In this case the MCU will be in sleep mode ninety present 90% of the time when performing live computations, and will be able to compute all the required calculations on time. Alternately, the MCU program can be ten times more complicated and demanding before the MCU will have difficulty executing it in the time allotted.

The solution was tested using floating point calculations and with a filter set solution. Therefore, another GA run limiting the chromosome maximum SSS to 16 genes was conducted, resulting in 14 filters; where the longest filter consisted of 350 coefficients. Five seconds of data were collected and the convolution computed on the fly for each sampled data point. Each time the microcontroller sampled a new value (100 Hz sampling rate), it computed all 14 filters. As result, the convolution algorithm is computed on each new data point using previously collected data for calculations. The MCU was configured to zero pad to allow calculation on the initial data points. The MCU output calculations were compared to a Matlab convolution function, to test the accuracy of the computations. Since the convolution is performed every 10 milliseconds on each new data point, the computations are finished at 500 data points (i.e. 5 seconds) and the convolution was not continued on the padded section. The MCU was able to compute all calculations in 6.6 milliseconds, on average, which still permits performance of all necessary computations in the allotted time.

The maximum amount of time it takes MCU to complete the whole computation was evaluated. The wavelet computations are performed in real time on each new second data point. Therefore, at every sixteenth data point, all four decomposition levels are performed. The data is sampled at 100 Hz for five seconds, providing 31 output values. The average computation time was 3.3 milliseconds, providing a window of 6.7 milliseconds for further computations. The first decomposition is performed on six data points and the second decomposition is performed on six output values from the first decomposition. 60% of the MCU RAM and 20% of its flash, were consumed, which does not leave much room to perform any additional computations. Two algorithms (one for heart contraction timing and one for stroke volume) need to be performed on the MCU. Therefore, the second algorithm was separately programmed and tested for MCU performance on this additional algorithm before making any hardware decisions. Note that further optimization may reduce memory footprint, and the two algorithms may run sequentially, and therefore use the same physical memory space at different times.

After the filter computations were verified, the acceleration information values were verified following decimation. If the Low Pass (LP) filter is convolved with the High Pass (HP), a new filter is created and if the input signal is convolved with the new filter and decimated by four, in theory, this should result in the same value as if two wavelet decompositions were performed [174]. The first decomposition is on the input signal providing the approximations of the Low Pass (LP) filter and the second decomposition provides the details of the High Pass (HP) filter. This theory was tested but failed to provide satisfactory results, since the final values from the two approaches did not fully match.

Our second approach to compute an efficient algorithm was to perform the decomposition path for each filter. In this way there are fewer computations since a convolution is performed on every second data point from the input level since each result is decimated by two. For example, the LP filter is computed on every second data point which is equivalent to applying it on the input signal and then decimating the output by two. The same is done on the HP filter where convolution is performed on every second data point of the LP filter output. The wavelet computations are performed in real time on each new second data point.

Therefore, at every sixteenth data point, all four decomposition levels are performed. Samples are taken at 100 Hz for five seconds, providing 31 output values. The average computation time was 3.3 milliseconds, providing a window of 6.7 milliseconds for further computations. The data is zero padded at the initialization stage, and later convolution performed where the number of data points is equal to the filter length. The first decomposition is performed on six data points and the second decomposition is performed on six output values from the first decomposition.

The heat rate detection algorithm is computed by the Continuous Wavelet Transform (CWT). The computations are done using cyclic convolution with the "true" Mother wavelets coefficients. This algorithm has two stages. The first stage is adaptive threshold windowing. This program requires 60% of the flash memory and about 80% of the RAM and does not leave much room to add more computations. To test the full program for detecting heart rate, the calculation was performed for ten seconds and then recorded the input and output signal for four seconds, where the total computation time was fourteen seconds. The average calculation time for the four seconds data was about 4.5 milliseconds, so the program can be computed in the time available between each new data point when data collection is at 100 Hertz.

The SV algorithm was programmed first and modified it to provide the same readings as the Matlab algorithm. The final results showed that the algorithm require 3.5 milliseconds to compute and occupies 60% of the RAM and 20% of the flash memory. The HR algorithm occupies 80% of the RAM and 60% of the flash memory. Both algorithms, therefore, cannot run at the same time on the board since both together exceed the amount of memory available on the Freedom-KL25Z evaluation board. The sub program which merges the output of the SV and HR algorithms requires little computation, but will still increase the amount of memory required by 10% of the available memory. Therefore, a new evaluation board with greater RAM and flash memory would be required to implement the full algorithm.

The drive behind minimizing computation time and filter sets was to create a small device which was portable (i.e. battery operated) and so would have limited computation capabilities. Different hardware types were investigated, including ASIC, FPGA, DSP and MCU, the MCU approach was determined the best fit for this application based on power consumption, acceptable computation power, speed to market, development ease, and feature flexibility. Moreover, an ARM based MCU with high performance and low power consumption, and which offered upwards compatibility, was preferred. An open source development platform was employed since it was tested by name users and supported multiple components allowing for rapid prototyping.

The SV and HR algorithms were tested separately, and both were shown to compute in less than half of the available time on the target MCU. Therefore, both algorithms together could be computed in less than ten milliseconds, allowing a 100 Hz sampling rate. However, the code to implement both algorithms could not fit together on the target MCU, and an alternative target MCU is needed which includes more RAM to hold the entire program.

It has been shown that the FRDM-KL25Z evaluation board is sufficiently fast to make the necessary computations in less than 10 ms, however, it would not be possible to compute both HR and SV algorithms simultaneously due to insufficient memory resources on this board. FRDM-KL46Z is an upper level board in the same family as the FRDM-KL25Z, with a built in 16 bit ADC and draws just 6 mA at full working state. The NXP LPC1768 has a 12 bit, 1 Megasample per second ADC, and draws 42 mA, but it runs at 96 MHz which would allow it to compute the required calculations faster, and then go into sleep mode to save power. A 16+ bit ADC is preferred, but techniques, such as subranging, dithering, and the like, can be used to increase the effective number of bits, especially when the required data acquisition rate is well below the sampling rate.

During initial analysis, it was assumed that observation of respiration rate since would not be possible, due to high-pass analog filtering to decrease "noise" in the frequency range of respiration (i.e. below a few Hz). However, the first integration for finding chest velocity shows that the low respiration frequency was observed to contribute significantly to the signal in the SV analysis. Therefore, the system can readily determine and output respiratory motion parameters, including respiratory rate. Because CO is influenced by breathing, incorporating breathing rate into the CO calculation may significantly improve the accuracy of the CO estimates.

The invention may be used as a method, system or apparatus, as programming codes for performing the stated functions and their equivalents on programmable machines, and the like. The aspects of the invention are intended to be separable, and may be implemented in combination, sub-combination, and with various permutations of embodiments. Therefore, the various disclosure herein, including that which is represented by acknowledged prior art, may be combined, subcombined and permuted in accordance with the teachings hereof, without departing from the spirit and scope of the invention.

All references cited herein are expressly incorporated herein by reference in their entirety.

BIBLIOGRAPHY

1. "Measuring Vital Signs", Providing Residential Services in Community Settings: A Training Guide Michigan Department of Human Services, 2009.
2. Blood pressure History, www.bloodpressurehistory.com/dates.html, last verify June 2011.
3. R. G. Newton, "Galileo's Pendulum: From the Rhythm of Time to the Making of Matter", Harvard University Press, 2004, p. 51.
4. P. Older, "Some facts and some thoughts on the history of oxygen uptake and its measurement", June 2007.
5. Adapted and modified from: sites.google.com/site/uk-drebbel and en.wikipedia.org/wiki/Cornelius_Drebbel, Last checked March 2011
6. J. Gribbin, Science a history 1543-2001, McPherson's Printing Group, Maryborough, Victoria, 2002
7. P. Correia. The ovary of eve: egg and sperm in preformation. 1997 Pages 22-25.
8. Bolam, Jeanne. 'The botanical works of Nehemiah Grew', F. R. S. (1641-1712), Source: Notes and Records of the Royal Society of London, Vol. 27. No. 2 Feb. 1973, 219-231.
9. A. L. Lavoisier. "Traite elementary de Chimie", Paris, 1790
10. L. D. Vandam and J. A Fox, Adolf Fick (1829-1901) Physiologist: a heritage for anesthesiology and critical care medicine, Anesthesiology 1998, Vol 88, pp 514-518

11. R. K. Murray, D. K. Granner, P. A. Mayes, V. W. Rodwell, Harper's Illustrated Biochemistry, LANGE Basic Science, 26th ed, McGraw-Hill Medical, 2003, pp. 44-45
12. V. Donald, J. G. Voet, C. W. Pratt, Fundamentals of Biochemistry: Life at the Molecular Level, John Wiley & Sons 3rd ed, 2008, pp. 189-190.
13. C. M. Tipton, Exercise physiology: people and ideas, American physiology society, Oxford university press, New York, 2003 pp. 106
14. Y. Henderson, L. Prince, "The Oxygen Pulse and the Systolic Discharge". Am J Physiological 1914; 35: 106-116
15. J. F. Stover, R. Stocker, R. Lenherr, T. A. Neff, S. R. Cottini, B. Zoller, M. Béchir, "Noninvasive cardiac output and blood pressure monitoring cannot replace an invasive monitoring system in critically ill patients", BMC Anesthesiology, Zurich, October 2009.
16. Source: www.forbes.com/sites/danmunro/2014/02/02/annual-u-s-healthcare-spending-hits-3-8-trillion/, Last verified May 2014.
17. Deloitte Center for Health Solutions, Washington, D.C. and Deloitte Center for Financial Services, New York, N.Y.," The hidden costs of U.S. health care for consumers: A comprehensive analysis", Deloitte Development LLC, March 2011.
18. "Heart Disease and Stroke Statistics", 2010 Update, American Heart Association.
19. Health and Recovery Services Administration (HRSA), "Nondurable Medical Supplies and Equipment (MSE)", Washington State Department of Social and Health Services, January 2007.
20. C. A. Vella and R. A. Robergs, "A review of the stroke volume response to upright exercise in healthy subjects." Br J Sports Med. 2005 April; 39(4):190-5.
21. K. Brown, Emergency Dysrhythmias ECG Injury Patterns, Thomson Learning, Delmar Learning, 2003, pp. 1-12.
22. W. Kluwer, ECG Interpretation, Lippincott Williams and Wilkins, New York, 2008.
23. S. Browbrick, A. N. Borg, ECG Complete, Elsevier: Churchill Livingstone, London, 2006.
24. N. J. Talley and S O'Connor, Examination Medicine, Edinburgh: Churchill Livingstone, 6th ed. pp. 41, 2009.
25. The Heart and Cardiac Output, Nursecom Educational Technologies, 2004.
26. M. R. Kinney and D. R. Packa, Comprehensive Cardiac Care, Missouri, Mosby, 8th ed. 1996, pp. 1-9.
27. Adapted and modified from: 3Dscience.com
28. Y. Henderson, Volume changes of the heart, Physiological Reviews, Vol. 3, 1923, pp. 165-208.
29. Adapted and modified from: anatomyforme.blogspot.com/2008_04_06 archive, and headstartinbiology.com/headstart/four45, Last checked March 2011
30. M. R. Kinney and D. R. Packa, Comprehensive Cardiac Care, 8th Edition, Mosby, Mo. 1996. pp 1-6.
31. Adapted and modified from: faculty.etsu.edu/forsman/Histologyofmuscleforweb, and healthmad.com/conditions-and-diseases/heart-histology, Last checked March 2011
32. Adapted and modified from: Sarcomere, wiki.verkata.com/en/wiki/Sarcomere, Last checked: March 2011
33. Adapted and modified from: people.eku.edukitchisong/RITCHISO/301notes5.htm, Last checked: March 2011
34. Adapted and modified from: 3Dscience.com and bem.fi/book/06/06.htm, last checked March 2011
35. Adapted from: ecglibrary.com/ecghist.html and en.ecgpedia.org/wiki/A_Concise_History_of_the ECG, last checked March 2011
36. W. Einthoven, "The Different Forms of The Human Electrocardiogram and Their Signification", The Lancet, March 1912
37. Adapted and modified from: en.ecgpedia.org/images/b/bb/Einthoven_ECG.jpg and library.med.utah.edu/kw/ecg/ecg_outline/Lesson1/lead_dia.html, Last checked: March 2011
38. D. Amin B. Fethi, "Features for Heartbeat Sound Signal Normal and Pathological", Recent Patents on Computer Science, 2008, Vol. 1, No. 1
39. R. R. Seeley, T. D. Stephens, P. Tate, Essentials of Anatomy and Physiology, McGraw-Hill, 2007, 321-352.
40. Center for Disease Control and Prevention, www.cdc.gov/VitalSigns/HAI, Last verified June 2011
41. J. McMichael and E. P. Sharpey, "Cardiac Output in man by a direct Fick Method", London December 1943, pp. 33-38.
42. E. E. Frezza, H. Mezghebe, "Indications and complications of arterial catheter use in surgical or medical intensive care units: analysis of 4932 patients", Am Surg 1998; 64: 127-131.
43. G. Kac, E. Durain, C. Amrein, E. Herisson, A. Fiemeyer, A. Buuhoi, "Colonization and infection of pulmonary artery catheter in cardiac surgery patients: epidemiology and multivariate analysis of risk factors" Critical Care Med 2001; 29: 971-975.
44. J. E. Dalen, "The Pulmonary Artery Catheter—Friend, Foe, or Accomplice?", JAMA, July 2001
45. D. A. Reuter, C. Huang, T. Edrich, S. K. Shernan, and H. K. Eltzschig, "Cardiac Output Monitoring Using Indicator-Dilution Techniques: Basics, Limits, and Perspectives", International Anesthesia Research Society, March 2010.
46. Adapted and modified from: hugo-sachs.de/haemo/carou.htm, Last verified May 2011.
47. A. Gawlinski, "Measuring Cardiac Output: Intermittent Bolus Thermodilution Method", American Association of Critical-Care Nurses, October 2004.
48. W. Isakow and D. P. Schuster, "Extravascular lung water measurements and hemodynamic monitoring in the critically ill: bedside alternatives to the pulmonary artery catheter", Washington, American Physiological Society, 2006.
49. C. Garcia-Rodriguez, J. Pittman, C. H. Cassell, J. Sum-Ping, H. El-Moalem, C. Young, J. B. Mark, "Lithium dilution cardiac output measurement: A clinical assessment of central venous and peripheral venous indicator injection", Crit Care Med, Vol 30, 2002.
50. V. K. Dhingra, J. C. Fenwick, K. R. Walley, D. R. Chittock, and J. J. Ronco, "Lack of agreement between thermodilution and fick cardiac output in critically ill patients", Chest, September 2002.
51. N. E. Haites, F. M. McLennan, D. R. Mowat, and J. M. Rawles, "Assessment of cardiac output by the Doppler ultrasound technique alone", University of Aberdeen, Aberdeen, Vol. 53, 1985.
52. Department of Healthcare and Human services, "Technology Assessment: Esophageal Doppler Ultrasound-Based Cardiac Output Monitoring for Real-Time Therapeutic Management of Hospitalized Patients", Agency for Healthcare Research and Quality, January 2007 pp. 7-21.
53. Diploma in Fetal Medicine & ISUOG Educational Series, "Doppler ultrasound: principles and practice", centrus.com.br 54. Adapted and modified from: minyakgaz.blogspot.com/2011/03/heart-disease-detection-treatment-and.html, Last verified May 2011.
55. W. G. Hundley, H. F. Li, L. D. Hillis, B. M. Meshack, R. A. Lange, J. E. Willard, C. Landau, R. M. Peshock, "Quantitation of cardiac output with velocity-encoded, phase-difference magnetic resonance imaging", American Journal of Cardiology, June 1995.
56. P. D. Gatehouse, J. Keegan, L. A. Crowe, S. Masood, R. H. Mohiaddin, K. F. Kreitner, D. N. Firmin, "Applications of phase-contrast flow and velocity imaging in cardiovascular MRI", European Radiology, July 2005.
57. J. F. Schenck, "Safety of Strong, Static Magnetic Fields", Journal of Magnetic resonance Imaging, March 2000.
58. Adapted and modified from: diagnostic-imaging.bayer-scheringpharma.de, Last verified May 2011.
59. J. A. Staessen, R. Fagard, L. Thijs, and A. Amery, "A Consensus View on the Technique of Ambulatory Blood Pressure Monitoring", American Heart Association, Inc, volume 26, 1995.
60. B. E. Westerhofa, J. Gisolfb, W. J. Stokb, K. H. Wesselingc, and J. M. Karemakerb, "Time-domain cross-correlation baroreflex sensitivity: performance on the EUROBAVAR data set", Finapres Medical System, Journal of Hypertension, 2004.
61. D. J. Wang, and S. S. Gottlieb, "Impedance cardiography: More questions than answers". Current Heart Failure Reports, Vol. 3, 2006, pp 107-113.
62. D. P. Bernstein, "Impledance cardiography: Pulsatile blood flow and the biophysical and electrodynamic basis for the stroke volume equations", Journal of Electrical Bioimpedance, Vol. 11, 2010, pp. 2-17.
63. M. Engoren, and D. Barbee, "Comparison of Cardiac Output Determined by Bioimpedance, Thermodilution, and the Fick Method", American Journal of Critical Care. 2005; 14: 40-45
64. Adapted and modified from: hemosapiens.com/teb.html, last verified May 2011.
65. Definition from: Merriam-Webster's Medical Dictionary, © 2007 Merriam-Webster, Inc.
66. B. W. Foster, "On a New Method of increasing the Pressure on the Artery in the use of the Sphygmograph." J Anat Physiol. 1868; 2(1):62-5
67. T. R. Fraser, "Effects of Rowing on the Circulation, as shown by the Sphygmograph." J Anat Physiol. 1868 November, 127-130.
68. J. G. McKendrick, Outlines of Physiology In Its Relations to Man, Macmillan and CO. London, 1878.
69. A. H. Garrod, "The Construction and use of a Simple Cardio-Sphygmograph." J Anat Physiol. 1871 May, 265-270.
70. W. J. Fleming, "A Simple Form of Transmission Sphygmograph." J Anat Physiol. 1877 October, 144-146.
71. T. Lewis, "The Interpretation of the Primary and First Secondary Wave in Sphygmograph Tracings." J Anat Physiol. 1907 January, 137-140
72. A. H. Garrod, "On the Mutual Relations of the Apex Cardiograph and the Radial Sphygmograph Trace", St. John's College, Cambridge. 1871 January, 318-324
73. H. A. Snellan, Willen Einthoven (1860-1927) Father of Electocardiography, Life and Work, Ancestors and Contemporaries, Kluwer Academic Publishers, 1995.
74. N. Coulshed, E. J. Epstein. "The Apex Cardiogram: Its Normal Features Explained By Those Found In Heart Disease", Br Heart J. 1963 November, 697-708.
75. ETafur, L. S. Cohen, H. D. Levine, "The Normal Apex Cardiogram: Its Temporal Relationship To Electrical, Acoustic, And Mechanical Cardiac Events", Circulation. 1964 September 381-391
76. A. Benchimol, E. G. Dimond, "The apex cardiogram in ischaemic heart disease", Br Heart J. 1962 September 581-594.
77. J. F. Legler, A. Benchimol, E. G. Dimond. "The apex cardiogram in the study of the 2-OS interval", Br Heart J. 1963 March 246-250.
78. S R. Jain, J. Lindahl, "Apex cardiogram and systolic time intervals in acute myocardial infarction", Br Heart J. 1971 July, 578-584.
79. J. Manolas, W. Rutishauser, "Relation between apex cardiographic and internal indices of left ventricular relaxation in man", Br Heart J. 1977 December 1324-1332.
80. C. M. Agress, S. Wegner, D. J. Bleifer, A. Lindsey, J. Von Houten, K. Schroyer, H. M. Estrin, "The Common Origin of precordial Vibrations", Am J Cardiol. 1964 April
81. L. M. Rosa, "The displacement vibrocardiogram of the precordium in the low frequency range", Am J Cardiol. 1959 August 191-199
82. C. M. Agress, S. Wegner, R. P. Fremont, I. Mori, D. J. Day, "Measurement of stroke volume by the vibrocardiogram", Aerosp Med. 1967 December 1248-1252.
83. L. Hume, D. J. Ewing, I. W. Campbell, S. R. Reuben, B. F. Clarke, "Non-invasive assessment of left ventricular response to Valsalva manoeuvre in normal and diabetic subjects using praecordial accelerocardiography", Br Heart J. 1979 February 199-203.
84. L. Hume, J. B. Irving, A. H. Kitchin, S. R. Reuben, "Effects of sustained isometric handgrip on praecordial accelerocardiogram in normal subjects and in patients with heart disease", Br Heart J. 1975 August 873-881
85. J. S. Forrester, R. Vas, G. Diamond, R. Silverberg, D. Tzivoni, "Cardiokymography: a new method for assessing segmental wall motion in man", Adv Cardiol. 1978, 48-64.
86. U. Morbiducci, L. Scalise, M. De Melis, M. Grigioni, "Optical vibrocardiography: a novel tool for the optical monitoring of cardiac activity", Ann Biomed Eng. 2007 January 45-58.
87. L. Scalise, U. Morbiducci, "Non-contact cardiac monitoring from carotid artery using optical vibrocardiography", Med Eng Phys. 2008 May, 490-497.
88. V. M. Khaiutin, E. V. Lukoshkova, G. G. Sheroziia, "Computer cardiokymography. On its way to long-term noninvasive monitoring of cardiac performance in daily life", Ross Fiziol Zh Im I M Sechenova. 2004 May 609-624.
89. J. W. Gordon, "Certain Molar Movements of the Human Body produced by the Circulation of the Blood." J Anat Physiol. 1877 April 533-536.
90. I. Starr, H. A. Schroeder, Ballistocardiogram. II. "Normal Standards, Abnormalities Commonly Found In Diseases of The Heart And Circulation, And Their Significance." J Clin Invest. 1940 May, 437-450.
91. A. Cournand, H. A. Ranges, R. L. Riley, "Comparison of Results of The Normal Ballistocardiogram And A Direct Fick Method In Measuring The Cardiac Output In Man." J Clin Invest. 1942 May 287-294.
92. J. L. Nickerson and H. J. Curtis, "The design of the ballistocardiograph," Am. J. Physiol., vol. 142, pp. 1, 1944.

93. Y. Henderson, "The mass-movements of the circulation as shown by a recoil curve," Am. J. Physiol., vol. 14, pp. 287, 1905.
94. W. W. von Wittern, "Ballistocardiography with elimination of the influence of the vibration properties of the body," Am. Heart J., vol. 46, pp. 705, 1953.
95. S. A. Talbot, D. C. Deuchar, F. W. Davis Jr., and W. R. Scarborough, "The aperiodic ballistocardiograph," Bull. Johns Hopkins Hosp., vol. 94, pp. 27, 1954.
96. H. C. Burger, A. Noordergraaf, and M. W. Verhagen, "Physical basis of the low-frequency ballistocardiograph," Am. Heart J., vol. 46, pp. 71, 1953.
97. M. B. Rappaport, "Displacement, velocity and acceleration ballistocardiograms as registered with an undamped bed of ultralow natural frequency," Am Heart J., vol. 52, no. 5, pp. 643-652, November 1956.
98. W. Dock, H. Mandelbaum, R. Mandelbaum, "Ballistocardiography: The application of the direct ballistocardiograph to clinical medicine", St Louis: CV Mosby 1953.
99. K. Tavakolian, A. Vaseghi, B. Kaminska. Improvement of ballistocardiogram processing by inclusion of respiration information. Physiol Meas. 2008 July 771-781.
100. S. Junnila, A Akhbardeh, A. Varri, "An Electromechanical Film Sensor Based Wireless Ballistocardiographic Chair: Implementation and performance", J. Sign Process Syst 2009, 305-320.
101. L. Y. Gyu, H. K. Hwan, K. K. Keun, S. J. Hyeog. P. K. Suk, "Mechanocardiogram Measured at the Back of Subjects Sitting in a Chair as a Non-intrusive Pre-ejection Period Measurement", Pervasive Health Conference and Workshops, November 2006.
102. O. T. Inan, M, Etemadi, A. Paloma, L. Giovangrandi, G. T. Kovacs, "Non-invasive cardiac output trending during exercise recovery on a bathroom-scale-based ballistocardiograph, Physiol Meas. 2009 March, 261-274
103. E. Pinheiro, O. Postolache, P. Girão, "Theory and developments in an unobtrusive cardiovascular system representation: ballistocardiography", Open Biomed Eng J. 2010 October 201-216.
104. E. E. Eddleman Jr., K. Willis, T. J. Reeves, T. R. Harrison, "The kinetocardiogram. I. Method of recording precordial movements. Circulation", 1953 August 269-275.
105. E. E. Eddleman Jr., K. Willis, L. Christianson, J. R. Pierce, R. P. Walker, "The kinetocardiogram. II. The normal configuration and amplitude" Circulation. 1953 September 370-380.
106. E. E. Eddleman Jr., K. Willis, "The kinetocardiogram. III. The distribution of forces over the anterior chest. Circulation", 1953 October 569-577.
107. W. Schweizer, R. V. Bertrab, P. Reist, "Kinetocardiography In Coronary Artery Disease", Br Heart J. 1965 March 263-268
108. B. S. Bozhenko, "Seismocardiography—a new method in the study of functional conditions of the heart", Ter Arkh. 1961 September 55-64
109. D. M. Salerno, J. Zanetti, "Seismocardiography: A New Techniqe for Recording Cardiac Vibrations. Concept, Method, and Initial Observations", j Cardiovas. Tech. 1990, 111-118.
110. D. M. Salerno, J. Zanetti, "Seismocardiography for monitoring changes in left ventricular function during ischemia", Chest. 1991 October 991-993.
111. R. S. Crow, P. Hannan, D Jacobs, L. Headquist, D. M. Salerno, "Relationship Between Seismocardiography and Echocardiogram for Events in the Cardiac Cycle", Am J Noninvas Cardiol 1994, 39-46.
112. I. K. Kubacka, R. Piotrowicz. "Seismocardiography—a noninvasive technique for estimating left ventricular function. Preliminary results", Przegl Lek. 2002, 774-776.
113. I. K. Kubacka, M. Bilińska, R. Piotrowicz. "Usefulness of seismocardiography for the diagnosis of ischemia in patients with coronary artery disease", Ann Noninvasive Electrocardiol. 2005 July, 281-287
114. M. Stork, Z. Trefny, "New seismocardiographic measuring system with separate QRS detection", WSEAS, Stevens Point, Wis., 2010. 176-180.
115. W. Sandham, D. Hamilton, A. Fisher, W. Xu, M. Conway, "Multiresolution Wavelet Decomposition of the Seismocardiogram", ieee transactions on signal processing, vol. 46, no. 9, sep. 1998, 2541-2543
116. P. Castiglioni, A. Faini, G. Parati, M. Di Rienzo, "Wearable seismocardiography" Conf Proc IEEE Eng Med Biol Soc. 2007, 3954-3957.
117. A. Tura, M. Badanai, D. Longo, L. Quareni, "A Medical Wearable Device with Wireless Bluetooth-based Data Transmission", Measurement Science Review, Volume 3, Section 2, 2003 1-4.
118. S. H. Woodward, N. J. Arsenault, K. Voelker, T. Nguyen, J. Lynch, K. Skultety, E. Mozer, G. A. Leskin, J. I. Sheikh, "Autonomic activation during sleep in post-traumatic stress disorder and panic: a mattress actigraphic study", Biol Psychiatry. 2009 July, 41-46.
119. P. L. Walter, "The History of the Accelerometer", Sound and Vibration, Texas Christian University, Fort Worth, Tex., January, 2007.
120. P. K. Stein, "The Early Strain Gage Accelerometers: The Inventors and Their Times," The Shock and Vibration Bulletin—Part II, Shock and Vibration Information Analysis Center (SAVIAC), 67th Shock and Vibration Symposium, Monterrey, Calif., November 1996.
121. McCullom, Burton and Peters, Orville S., "A New Electric Telemeter," Technology Papers, National Bureau of Standards No. 247, Vol. 17, Jan. 4, 1924.
122. P. L. Walter, "A History Of The Origin And Evolution Of Modal Transducers", Texas Christian University, Fort Worth Tex., International Modal Analysis Conference (IMAC) XX, Session 18, Los Angeles, Calif., February 2002.
123. R. Yan and R. X. Gao, "Tutorial 21 Wavelet Transform: A Mathematical Tool for Non-Stationary Signal Processing in Measurement Science Part 2 in a Series of Tutorials in Instrumentation and Measurement", IEEE Instrumentation and Measurement Magazine, October 2009.
124. Adapted from: archive.cnmat.berkeley.edu/~alan/MS-html/MSv2.html
125. Graps, A. (1995) An Introduction to Wavelets IEEE Computational Science and Engineering, vol. 2, num. 2, June 1995. doi:10.1109/99.388960
126. K. Parashar, "Discrete Wavelet Transform", thepolygoners.com/tutorisld/dwavelet/dwttut.html
127. C. Valens, "A Really Friendly Guide to Wavelets", C. Valens 1999
128. S. Ehara, T. Okuyama, N. Shirai, H. Oe, Y. Matsumura, K. Sugioka, T. Itoh, K. Otani, T. Hozumi, M. Yoshiyama, J. Yoshikawa, "Comprehensive evaluation of the apex beat using 64-slice computed tomography: Impact of left ventricular mass and distance to chest wall". J Cardiol. 2010 March pp. 256-265.
129. Adapted from and modified from: www.nottingham.ac.uk
130. L. Mangin, C. Clerici, T. Similowski, C. S. Poon, "Chaotic dynamics of cardioventilatory coupling in humans: effects of ventilatory modes", Am J Physiol 131. S. T. Linsenbardt, T. R. Thomas, R. W. Madsen, "Effect of breathing techniques on blood pressure response to resistance exercise", Br J Sports Med, PubMed PMID: 1623367; PubMed Central PMCID: PMC1478931. 1992 Jun. 26(2) pp. 97-100.

132. S. Haykin, Communication Systems, 4th Ed. John Wiley and Sons, Inc. 2001. pp. 88-106.

133. N. Y. Raval, P. Squara, M. Cleman, K. Yalamanchili, M. Winklmaier, D. Burkhoff, "Multicenter Evaluation of Noninvasive Cardiac Output Measurement by Bioreactance Technique", Journal of Clinical Monitoring and Computing, February 2008.

134. Adapted from: cheetah-medical.com

135. H. Keren, D. Burkhoff, P. Aquara, "Evaluation of a noninvasive continuous cardiac output monitoring system based on thoracic bioreactance", The American Physiological Society, March 2007.

136. P. Squara, D. Denjean, P. Estagnasie, A. Brusset, J. C. Dib, C. Dubois, "Noninvasive cardiac output monitoring (NICOM): a clinical validation", Intensive Care Med, March 2007.

137. Health Plan of Nevada, Sierra Health and Life, United Health Care Company, "Electrical Bioimpedance for Cardiac Output Measurement", Protocol: CAR022, Effective June 2010.

138. D. H. Wolpert, W. G. Macready, "No Free Lunch Theorems for Optimization," IEEE Transactions on Evolutionary Computation. April 1997.

139. A. Marczyk, Genetic Algorithms and Evolutionary Computation, Apr. 23, 2004. Last visit: Jan. 11, 2013, www.talkorigins.org/faqs/genalg/genalg.html 140. D. E. Goldberg, Genetic Algorithms in Search, Optimization, and Machine Learning, Addison-Wesley Professional, January 1989.

141. J. H. Holland, Adaptation in Natural and Artificial Systems: An Introductory Analysis with Applications to Biology, Control and Artificial Intelligence, The University of Michigan Press, 1975

142. MathWorks, Peaks function, Example function of two variables, last visited: November 2013, www.mathworks.com/help/matlab/ref/peaks.html 143. Y. Zhang and A. M. Agogino, "Interactive Hybrid Evolutionary Computation for MEMS Design Synthesis", Adv. in Neural Network Research & Appli., LNEE 67, pp. 211-218, Springer-Verlag Berlin Heidelberg 2010.

144. M. Mitchell, J. H. Holland, and S Forrest, "When Will a Genetic Algorithm Outperform Hill Climbing?", Advances in Neural Information Processing Systems 6 (1993).

145. S. Kirkpatrick, C. D. Gelatt, and M. P. Vecchi, "Optimization by Simulated Annealing", Science, New Series, Vol. 220, No. 4598. (May 13, 1983), pp. 671-680.

146. E. C. Segura, "Evolutionary Computation with Simulated Annealing: Conditions for Optimal Equilibrium Distribution", JCS&T Vol. 5 No. 4, December 2005.

147. L. J. Eshelman (1991) The CHC Adaptive Search Algorithm: How to have Safe Search When Engaging in Nontraditional Genetic Recombination, Foundations of Genetic Algorithms, Publisher: Morgan Kaufmann, Editors: G. J. E. Rawlings, pp. 265-283

148. K. E. Mathias, L. J. Eshelman, J. D. Schaffer, L. Augusteijn, P. Hoogendijk and R van de Wiel. (2000) Code Compaction Using Genetic Algorithms, Proceedings of the Genetic and Evolutionary Computation Conference (GECCO2000), Morgan Kaufmann, San Francisco, Calif., 2000.

149. J. D. Schaffer, A. Janevski, and M. R. Simpson A Genetic Algorithm Approach for Discovering Diagnostic Patterns in Molecular Measurement Data, Philips Research—USA, Computational Intelligence in Bioinformatics and Computational Biology, 2005. CIBCB '05. Proceedings of the 2005 IEEE Symposium, doi:10.1109/CIBCB.2005.1594945

150. K. E. Mathias, L. J. Eshelman, and J. D. Schaffer, "Niches in NK-Landscape", In proceeding of: Proceedings of the Sixth Workshop on Foundations of Genetic Algorithms, Charlottesville, Va., USA, July 21-23, 2000.

151. S. Picek, and M. Golub, "Comparison of a Crossover Operator in Binary-coded Genetic Algorithms", WSEAS TRANSACTIONS on COMPUTERS, Issue 9, Volume 9, September 2010.

152. L. J. Eshelman, and J. D. Schaffer Real-Coded Genetic Algorithms and Interval Schemata, In Foundations of Genetic Algorithms 2, Darrell Whitley (editor), Morgan Kaufmann, San Mateo, C A, 1993, 187-202.

153. S. Kadambe, R. Murray, and G. F. Boudreaux-Bartels Wavelet Transform-Based QRS Complex Detector, IEEE Transactions on Biomedical Engineering, Vol. 46, no. 7, July 1999. 838-48.

154. W. Chen, Z. Mo, and W. Guo Detection of QRS Complexes Using Wavelet Transforms and Golden Section Search algorithm, International Journal of Engineering and Advanced Technology (IJEAT), Volume-1, Issue-6, August 2012, 2249-895

155. P. Mithun, P. C. Pandey, T. Sebastian, P. Mishra, and V. K. Pandey A wavelet based technique for suppression of EMG noise and motion artifact in ambulatory ECG, 33rd Annual International Conference of the IEEE EMBS. 2011:7087-90. doi: 10.1109/IEMBS.2011.6091791.

156. J. Frère, B. Göpfert, J. Slawinski, and C. Tourny-Chollet Shoulder muscles recruitment during a power backward giant swing on high bar: a wavelet-EMG-analysis, Hum Mov Sci. 2012 April doi: 10.1016/j.humov.2012.02.002.

157. T. W. Beck, T. J. Housh, A. C. Fry, J. T. Cramer, J. P. Weir, B. K. Schilling, M. J. Falvo, and C. A. Moore (2009) A wavelet-based analysis of surface mechanomyographic signals from the quadriceps femoris, Muscle Nerve. 2009 March; 39(3):355-63. PubMed PMID: 19208397.

158. S. Kannan, J. Dauwels, and R. Ramasubba Multichannel EEG compression: Wavelet-based image and volumetric coding approach IEEE Trans Inf Technol Biomed. 2012 Apr. 9. [Epub ahead of print] PubMed PMID: 22510952.

159. T. Nguyen-Ky, P. Wen, Y. Li, and M. Malan Measuring the hypnotic depth of anaesthesia based on the EEG signal using combined wavelet transform, eigenvector and normalisation techniques, Comput Biol Med. 2012 May 8. doi: 10.1016/j.compbiomed.2012.03.004. PubMed PMID: 22575174.

160. N. Heidari, R. Azmi, and B. Pishgoo Fabric Textile Defect Detection, By Selecting A Suitable Subset of Wavelet Coefficients, Through Genetic Algorithm, International Journal of Image Processing (IJIP), Volume (5): Issue (1): 2011

161. Ali S. Amjad, S. Vathsal, and K. Lal Kishore A GA-based Window Selection Methodology to enhance Window-based Multi-wavelet transformation and thresholding aided CT image denoising technique, (IJCSIS)

International Journal of Computer Science and Information Security, Vol. 7, No. 2, February 2010.
162. P. T. Hosseini, F. Almasganj, T. Emami, R. Behroozmand, S. Gharibzade, and F. Torabinezhad Local Discriminant Wavelet Packet Basis for Voice Pathology Classification, Bioinformatics and Biomedical Engineering, 2008. ICBBE 2008. The 2nd International Conference, 978-1-4244-1748-3/08, IEEE, 2008, doi:10.1109/ICBBE.2008.842
163. J. Mingyan, L. Changchun, Y. Dongfeng, and A. Miguel Multiuser Detection Based on Wavelet Packet Modulation and Artificial Fish Swarm Algorithm, Wireless, Mobile and Sensor Networks, 2007. (CCWMSN07). IET Conference.
164. J. Mingyan, Y. Dongfeng, J. Zheng, and W. Miaomiao Determination Of Wavelet Denoisingthreshold by PSO and GA, 2005 IEEE International Symposium on Microwave, Antenna, Propagation and EMC Technologies for Wireless Communications Proceedings, doi:10.1109/MAPE.2005.1618192
165. C. Punyadeera, E. M. Schneider, J. D. Schaffer, H. Hsin-Yun, T. O. Joos, F. Kriebel, M. Weiss, and W. F. J. Verhaegh A biomarker panel to discriminate between systemic inflammatory response syndrome and sepsis and sepsis severity, journal of Emergencies, Trauma & Shock; January 2010, Vol. 3 Issue 1, p 26, doi:10.4103/0974-2700.58666
166. L. Boroczky, L. Zhao, and K. P. Lee Feature Subset Selection for Improving the Performance of False Positive Reduction in Lung Nodule CAD, IEEE Transactions on Information Technology in Biomedicine—TITB, vol. 10, no. 3, pp. 504-511, 2006.
167. A. Janevski, S. Kamalakaran, N. Banerjee, V. Varadan, and N. Dimitrova, PAPAyA: a platform for breast cancer biomarker signature discovery, evaluation and assessment, BMC Bioinformatics, vol. 10, no. S-9, pp. 7-8, 2009. doi:10.1186/1471-2105-10-S9-S7
168. J. D. Schaffer, M. Mani, L. J. Eshelman, and K. Mathias The Effect of Incest Prevention on Genetic Drift, Foundations of Genetic Algorithms 5, Banzhaf, Reeves (editors), Morgan Kaufmann, San Mateo, C A, 1998, 235-243.
169. P. Bishop, A tradeoff between microcontroller, DSP, FPGA and ASIC technologies, 2/25/2009 04:00 PM EST, www.eetimes.com/document.asp?doc_id=1275272, last visited Dec. 22, 2013.
170. L. MacCleery, National Instruments, Reconfigurable Grid? FPGA Versus DSPs for Power Electronics 2012, ftp://ftp.ni.com/evaluation/powerdev/niweek2012/ETS-_Day1/Lin_MacCleery_Final_ETS_2012. p df, Last visited May 2014,
171. R. Chawla, FPGAs and Structured ASICs: New Solutions for Changing Market Dynamics, Chip Design Magazine, chipdesignmag.com/display.php?articleId=255 Last visited Dec. 22, 2013.
172. ARM, Cortex-M series, www.arm.com/products/processors/cortex-m/index.php, Last visited Dec. 22, 2013.
173. Livejournal.com, panchul.livejournal.com/184647.html, Last visited Dec. 22, 2013.
174. L. Adams, Choosing the Right Architecture for Real-Time Signal Processing Designs, Texas Instruments, White Paper, SPRA879, Strategic Marketing, Texas Instruments, November 2002.
175. B. Porat, A course in digital signal processing, John Wiley & Sons, Inc. 1997 P. 475
176. Varady, P., "Wavelet-based adaptive denoising of phonocardiographic records", Engineering in Medicine and Biology Society, 2001. Proceedings of the 23rd Annual International Conference of the IEEE.
177. Akhbardeh A, Tavakolian K, Gurev V, Lee T, New W, Kaminska B, Trayanova N, "Comparative analysis of three different modalities for characterization of the seismocardiogram", Conf Proc IEEE Eng Med Biol Soc. 2009; 2009:2899-903. doi: 10.1109/IEMBS.2009.5334444.
178. Dinh A., "Heart Activity Monitoring on Smartphone", 2011 International Conference on Biomedical Engineering and Technology, IPCBEE vol. 11 (2011) © (2011) IACSIT Press, Singapore
179. Tavakolian K., Dumont G. A., Blaber A. P., "Analysis of seismocardiogram capability for trending stroke volume changes: A lower body negative pressure study", Computing in Cardiology (CinC), September 2012.
180. Brüser C., Stadlthanner K., de Waele S., Leonhardt S., "Adaptive Beat-to-Beat Heart Rate Estimation in Ballistocardiograms", IEEE Trans Inf Technol Biomed. 2011 September; 15(5):778-86. doi: 10.1109/TITB.2011.2128337. Epub 2011 Mar. 17.
181. Tavakolian K., Blaber A. P., Ngai B., Kaminska B., "Estimation of hemodynamic parameters from Seismocardiogram", Computing in Cardiology (CinC), September 2012.
182. Tavakolian K., Ngai B., Akhbardeh, A., Kaminska B., Blaber A. P., "Comparative Analysis of Infrasonic Cardiac Signals", Computers in Cardiology, September 2009.
183. Wilson R. A., Bamrah V. S., Lindsay J. Jr., Schwaiger M., Morganroth J., "Diagnostic accuracy of seismocardiography compared with electrocardiography for the anatomic and physiologic diagnosis of coronary artery disease during exercise testing." Am J Cardiol. 1993 Mar. 1; 71(7):536-45.
184. McKay W. P., Gregson P. H., McKay B. W., Militzer J., "Sternal acceleration ballistocardiography and arterial pressure wave analysis to determine stroke volume", Clin Invest Med. 1999 February; 22(1):4-14.
185. Ngai B., Tavakolian K., Akhbardeh A., Blaber A. P., Kaminska B., Noordergraaf A., "Comparative analysis of seismocardiogram waves with the ultra-low frequency ballistocardiogram", Conf Proc IEEE Eng Med Biol Soc. 2009; 2009:2851-4. doi: 10.1109/IEMBS.2009.5333649.
186. Ramos-Castro J., Moreno J., Miranda-Vidal H., Garcia-Gonzalez M. A., Fernandez-Chimeno M., Rodas G., Capdevila Ll., "Heart Rate Variability analysis using a Seismocardiogram signal", 34th Annual International Conference of the IEEE EMBS, San Diego, Calif. USA, 28 August-1 Sep. 2012.
187. Laurin A., Blaber A., Tavakolian K., "Seismocardiograms return Valid Heart Rate Variability Indices", Computing in Cardiology 2013; 40:413-416.
188. Imtiaz M. S., Shrestha R., Dhillon T., Yousuf K. A., Saeed B., Dinh A., Wahid K., "Cardiac Cycle and Heart Rate Calculation Based on Seismocardiogram", 2013 26th IEEE Canadian Conference Of Electrical And Computer Engineering (CCECE).
189. Ruqiang Y. and Gao, R. X. (2009) Tutorial 21 Wavelet Transform: A Mathematical Tool for Non-Stationary Signal Processing in Measurement Science Part 2 in a Series of Tutorials in Instrumentation and Measurement. IEEE Instrumentation & Measurement Magazine, vol. 12, num. 5, October 2009 10.1109/MIM.2009.5270529.
190. Domingues M. O., Mendes O. Jr, da Costa A. M. (2005) On wavelet techniques in atmospheric sciences, Advances in Space Research, Volume 35, Issue 5, 2005, Pages 831-842, ISSN 0273-1177, Elsevier Ltd, 2005 COSPAR, doi:10.1016/j.asr.2005.02.097
191. Chourasia V. S., Mittra A. K. (2009) Selection of mother wavelet and denoising algorithm for analysis of foetal phonocardiographic signals, Journal of Medical Engineering & Technology, vol. 33, No. 6, August 2009, 442-448, doi: 10.1080/03091900902952618
192. Korzeniowska-Kubacka I., Piotrowicz R. (2002) Seismocardiography—a noninvasive technique for estimating left ventricular function. Preliminary results, Przegl Lek. 2002, 774-776.
193. Raval N. Y., Squara P., Cleman M., Yalamanchili K., Winklmaier M., Burkhoff D. (2008) Multicenter Evaluation of Noninvasive Cardiac Output Measurement by Bioreactance Technique, Journal of Clinical Monitoring and Computing, February 2008. doi:10.1007/s10877-008-9112-5
194. Keren H., Burkhoff D., Squara P. (2007) Evaluation of a noninvasive continuous cardiac output monitoring system based on thoracic bioreactance, Am J Physiol Heart Circ Physiol, March 2007.
195. Squara P., Denjean D., Estagnasie P., Brusset A., Dib J. C., Dubois C. (2007) Noninvasive cardiac output monitoring (NICOM): a clinical validation, Intensive Care Med, March 2007.
196. Kac G., Durain E., Amrein C., Hérisson E., Fiemeyer A., Buu-Hoï A. (2001) Colonization and infection of pulmonary artery catheter in cardiac surgery patients: epidemiology and multivariate analysis of risk factors, Critical Care Med 2001; 29: 971-975.
197. Dalen J. E. (2001) The Pulmonary Artery Catheter—Friend, Foe, or Accomplice, JAMA, July 2001, 18; 286 (3):348-50.
198. Eshelman L. J., and Schaffer J. D. (1993) Real-Coded Genetic Algorithms and Interval Schemata, In Foundations of Genetic Algorithms 2, Darrell Whitley (editor), Morgan Kaufmann, San Mateo, C A, 1993, 187-202.
199. Radcliffe N. (1994) The Algebra of Genetic Algorithms, Annals of Maths and Artificial Intelligence, vol 10, 1994, 339-384.
200. Radcliffe N. (1991) Forma Analysis of Random respectful Recombination, International Conference on Genetic Algorithms, 1991, 222-229.

| LIST OF ABBREVIATIONS | |
|---|---|
| ACG | Apex-CardioGram |
| AM | Amplitude Modulation |
| ARM | Advanced RISC Machines |
| ASIC | Application Specific Integrated Circuit |
| AV | AtrioVentricular |
| BCG | BallistoCardioGram |
| BLX | Blend Crossover |
| BMI | Body Mass Index |
| BP | Blood Pressure |
| BPM | Beats Per Minute |
| BSA | Body Surface Area |
| CAM | Complementary and Alternative Medical |
| CHC | Cross generation rank selection, HUX, Cataclysmic mutation |
| CI | Cardiac Index |
| CKG | CardioKymoGraphy |
| CO | Cardiac Output |
| CPU | Central Processing Unit |
| CT | Computed Tomography |
| CVD | CardioVascular Disease |
| CWT | Continuous Wavelet Transform |
| DFT | Discrete Fourier Transform |

-continued

| LIST OF ABBREVIATIONS | |
|---|---|
| DSP | Digital Signal Processor |
| DWT | Discreet Wavelet Transform |
| EC | Evolutionary Computations |
| ECG | ElectroCardioGram |
| EE | Exhaustive Enumeration |
| EEG | ElectroEncephaloGraphy |
| EMG | ElectroMyoGraphy |
| EP | Evolutionary Programing |
| ES | Evolution Strategies |
| ET | Ejection Time |
| FDA | Food and Drug Administration |
| FFT | Fast Fourier Transform |
| FIR | Finite Impulse Response |
| FN | False Negative |
| FP | False Positive |
| FPGA | Field Programmable Gate Array |
| GA | Genetic Algorithm |
| GP | Genetic Programing |
| HC | Hill Climber |
| HDK | Hardware Development Kit |
| HR | Heart Rate |
| HUX | Half Uniform crossover |
| IC | Integrated Circuit |
| ICT | Isometric Contraction Time |
| ICU | Intensive Care Unit |
| IDE | Integrated Developer environment |
| IHC | Iterated Hill Climbers |
| KCG | KinetoCardioGram |
| MCU | MicroController Unit |
| MEMS | MicroElectroMechanical systems |
| MIPS | Million Instructions Per-Second |
| MMG | MechanoMyoGraphy |
| MRI | Magnetic Resonance Imaging |
| MW | Mother Wavelet |
| NASA | National Aeronautics and Space Administration |
| NICOM | Non-Invasive Cardiac Output Monitoring |
| ODE | Office of Device Evaluation |
| OOP | Out Of Pocket |
| PAC | Pulmonary Artery Catheter |
| PCG | PhonoCardioGram |
| RAM | Random Access Memory |
| RISC | Reduced Instruction Set Computer |
| RRR | Random Respectful Recombination |
| RS | Random Search |
| SA | Simulated Annealing |
| SCG | SeismoCardioGram |
| SDK | Software Development Kit |
| SSS | SubSet Size |
| STFT | Short Time Fourier Transform |
| SV | Stroke Volume |
| TEB | Thoracic Electrical Bio-impedance |
| TP | True Positive |
| VbCG | VibroCardioGram |
| VET | Ventricle Ejection Time |

What is claimed is:

1. A method for computing cardiac stroke volume of a subject, comprising:
obtaining parameters of a wavelet packet function and basing the parameters on calibration data from a plurality of members of a population, the wavelet packet function relating information from a transducer representing chest wall movements associated with a respective heartbeat to cardiac stroke volume of the respective heartbeat;
measuring chest wall movements of the subject;
performing a wavelet transform on the measured chest wall movements of the subject to produce a set of wavelet transformed data;
determining, from the wavelet transformed data and the parameters of the wavelet packet function, at least a cardiac stroke volume of the respective heartbeat for the subject; and one of (a) displaying on a display device, and (b) controlling a therapeutic cardiac device, based on at least one of (i) the determined cardiac stroke volume, and (ii) a value calculated from the determined cardiac stroke volume.

2. A system for computing a cardiac performance, comprising:
a display device configured to present a display;
a transducer configured to sense chest wall movements of a subject and to produce a transducer output representing the sensed chest wall movements;
a memory storing parameters of a wavelet packet function, the stored parameters being based on calibration data from a plurality of members of a population, the wavelet packet function relating sensed chest wall movements associated with a respective heartbeat to cardiac stroke volume of the respective heartbeat
at least one automated processor, configured to:
retrieve, from the memory, stored parameters of the wavelet packet function;
perform a wavelet transform on the sensed chest wall movements; and
calculate at least a cardiac stroke volume estimate of the respective heartbeat from the wavelet transformed sensed chest wall movements and the parameters, using the retrieved parameters for the wavelet packet function; and
one of: (a) display information selectively dependent on the cardiac stroke volume estimate to the display device, for presentation to a user, and (b) control a therapeutic cardiac medical device selectively dependent on the cardiac stroke volume estimate.

3. The system according to claim 2, wherein the chest wall movements are sensed as vibrations comprising at least frequencies over the range of 5-25 Hz.

4. The system according to claim 2, wherein the transducer comprises an accelerometer.

5. The system according to claim 2, wherein the at least one automated processor is further configured to determine at least one of a heart contraction timing and a heart contraction timing variability, based on the sensed chest wall movements.

6. The system according to claim 2, wherein the at least one automated processor is further configured to determine a heart rate, and to determine a cardiac output, based on at least the determined heart rate and the calculated cardiac stroke volume.

7. The system according to claim 2, wherein the wavelet transform employs at least two different wavelet decomposition paths, each respective wavelet decomposition path employing a respectively different type of wavelet packet, and the wavelet packet function comprises a set of wavelet packet parameters applied to a subset of the different types of wavelet packets of the at least two different wavelet decomposition paths.

8. The system according to claim 7, wherein the wavelet packet function is a genetic algorithm optimized, low computational complexity wavelet packet function, employing parameter coefficients for terms of the at least two different wavelet decomposition paths, adapted to produce the calculated cardiac stroke volume having a high correspondence with a benchmark.

9. The system according to claim 2, wherein the at least one automated processor is further configured to employ at least one of an evolutionary algorithm and a genetic algorithm to define the parameters of an optimal wavelet packet function which optimizes both a correlation of the cardiac stroke volume with a benchmark, and a computational complexity of the wavelet packet function.

10. The system according to claim 2,
wherein the calibration data from the plurality of humans comprises sensed chest wall movements and measured cardiac output for the plurality of humans, and
wherein the wavelet packet function is an optimal wavelet packet function with respect to at least the calibration data,
and the at least one automated processor is further configured to determine:
a heart contraction timing based on the sensed chest wall movements, and
a cardiac output as a function of the determined the stroke volume and heart contraction timing.

11. The system according to claim 2, wherein the wavelet transform comprises a plurality of different mother wavelet types, in a plurality of decomposition paths, in a plurality of different filters at different frequencies.

12. The system according to claim 2, wherein the transducer comprises an accelerometer configured to be placed on the xiphoid process of the sternum.

13. The system according to claim 2, wherein at least one body characteristic of the subject is stored in the memory, and the at least one automated processor is further configured to:
calculate a non-normalized cardiac output value based on the sensed chest wall movements of the subject;
store the non-normalized cardiac output value in the memory;
communicate the non-normalized cardiac output value through a communication port; and
normalize the non-normalized cardiac output value according to the at least one body characteristic of the subject to produce a normalized cardiac output value.

14. The system according to claim 13, wherein the at least one automated processor is further configured to control a communication of the non-normalized cardiac output value over a wireless communication link,
further comprising a smartphone configured to receive the non-normalized cardiac output value through the wireless communication link, and to normalize the non-normalized cardiac output value to produce the cardiac output value normalized for the at least one body characteristic of the subject.

15. The system according to claim 2, wherein the at least one automated processor is further configured to determine at least one of: a variability of a cardiac stroke volume, and a variability of a cardiac output, based on at least the sensed chest wall movements.

16. The system according to claim 2, wherein the transducer is configured to sense the chest wall movements of the subject during breathing and physical exertion, and the at least one automated processor is further configured to receive as inputs a height and a weight of the subject, either calculate or receive as an input a heart rate of the subject, and to calculate a cardiac output based on at least the height, weight, the calculated cardiac stroke volume, and the heart rate.

17. The system according to claim 2, further comprising a housing configured to be wearable by a human, containing at least:
the transducer configured to sense chest wall movements;
a self-contained power source; and
the at least one automated processor, comprising a microcontroller powered by the self-contained power source, the at least one automated processor being further configured to process the sensed chest wall movements on a beat-by-beat basis, to store the cardiac stroke volume estimate in the memory, and to communicate the stored cardiac stroke volume estimate through a communication port;

wherein the communicated stored cardiac stroke volume estimate is adapted to be processed by a remote system to calculate a cardiac output.

18. The system according to claim 17, further comprising an acceleration sensor configured to determine an acceleration vector of the housing, the acceleration sensor being distinct from the transducer, the microcontroller being further configured to determine an artifact condition based on the acceleration vector.

19. The system according to claim 2, further comprising an electrocardiogram input configured to provide information for determining a heart contraction timing, the cardiac stroke volume estimate being further calculated dependent on the determined a heart contraction timing.

20. The system according to claim 2, wherein:
the wavelet transform comprises a plurality of different mother wavelet waveforms in a plurality of different decomposition paths, each respective decomposition path having a plurality of respective terms;
the wavelet packet function applies respective parameters to respective terms of the wavelet transform; and
the least one automated processor is further configured to:
perform an iterative genetic algorithm for optimizing the parameters of the wavelet packet function;
convolve the plurality of different mother wavelet waveforms in the plurality of different decomposition paths with at least a portion of the calibration data;
define at least one fitness criterion for the wavelet packet function dependent on the convolution;
optimize the respective parameters, based on at least the iterative genetic algorithm and the defined at least one fitness criterion; and
store the optimized respective parameters in the memory.

21. The system according to claim 20, wherein the at least one automated processor is further configured to together optimize the plurality of respective terms of the wavelet packet function and at least one respective parameter applied to a respective term, based on the at least an iterative genetic algorithm and the at least one fitness criterion.

22. The system according to claim 20, wherein:
the at least one automated processor is further configured to:
determine a correlation $R^2$ of the wavelet packet function with a reference at a respective stage of the iterative genetic algorithm; and
calculate the at least one respective parameter applied to each respective term of the wavelet packet function, based on at least the correlation $R^2$,
wherein a precision of the correlation $R^2$ is sufficiently limited in order to increase a rate of convergence of the iterative genetic algorithm.

23. The system according to claim 20, wherein the at least one automated processor is further configured to perform the wavelet transform on the sensed chest wall movements to produce a wavelet transform domain representation, and to apply the stored optimized at least one respective parameter to each respective term of the wavelet packet function in the wavelet transform domain representation.

24. The system according to claim 2, wherein the at least a cardiac stroke volume estimate is calculated further dependent on a chest circumference measurement of the subject.

25. A system for computing cardiac performance, comprising:
a memory configured to store parameters of a wavelet packet function, the stored parameters being based on calibration data from a plurality of members of a human population relating chest wall movement data to at least cardiac stroke volume;
a transducer configured to sense chest wall movement data from a respective human;
a wavelet transform processor, configured to produce a wavelet transform of the chest wall movement data of the respective human;
a cardiac stroke volume processor, configured to evaluate the wavelet packet function to at least estimate a cardiac stroke volume of the respective human based on the wavelet transform of the chest wall movement data and the stored parameters of the wavelet packet function; and
one of:
(a) a display device configured to display the estimated cardiac stroke volume; and
(b) a therapeutic cardiac device configured to deliver a therapy to the respective human selectively dependent on the estimated cardiac stroke volume.

\* \* \* \* \*